(12) United States Patent
Zarbis-Papastoitsis et al.

(10) Patent No.: US 12,048,746 B2
(45) Date of Patent: Jul. 30, 2024

(54) IL-6 ANTAGONIST FORMULATIONS AND USES THEREOF

(71) Applicant: SESEN BIO, Inc., Cambridge, MA (US)

(72) Inventors: Grigorios Zarbis-Papastoitsis, Watertown, MA (US); Patricia Lowden, Hudson, MA (US)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 0 days.

(21) Appl. No.: 17/462,654

(22) Filed: Aug. 31, 2021

(65) Prior Publication Data

US 2022/0241414 A1 Aug. 4, 2022

Related U.S. Application Data

(63) Continuation of application No. 16/078,671, filed as application No. PCT/US2017/019131 on Feb. 23, 2017, now abandoned.

(60) Provisional application No. 62/298,774, filed on Feb. 23, 2016.

(51) Int. Cl.
| | |
|---|---|
| *A61K 39/395* | (2006.01) |
| *A61K 9/00* | (2006.01) |
| *A61K 45/06* | (2006.01) |
| *A61K 47/02* | (2006.01) |
| *A61K 47/10* | (2017.01) |
| *A61K 47/18* | (2017.01) |
| *A61K 47/22* | (2006.01) |
| *A61K 47/26* | (2006.01) |
| *C07K 16/24* | (2006.01) |

(52) U.S. Cl.
CPC ...... *A61K 39/39591* (2013.01); *A61K 9/0019* (2013.01); *A61K 9/0048* (2013.01); *A61K 39/3955* (2013.01); *A61K 45/06* (2013.01); *A61K 47/02* (2013.01); *A61K 47/10* (2013.01); *A61K 47/183* (2013.01); *A61K 47/22* (2013.01); *A61K 47/26* (2013.01); *C07K 16/248* (2013.01); *C07K 2317/94* (2013.01)

(58) Field of Classification Search
CPC .......... A61K 39/39591; A61K 39/3955; C07K 16/248
See application file for complete search history.

(56) References Cited

U.S. PATENT DOCUMENTS

| | | | |
|---|---|---|---|
| 4,548,990 A | 10/1985 | Mueller et al. | |
| 4,816,567 A | 3/1989 | Cabilly et al. | |
| 5,223,409 A | 6/1993 | Ladner et al. | |
| 5,225,539 A | 7/1993 | Winter | |
| 5,476,996 A | 12/1995 | Wilson et al. | |
| 5,530,101 A | 6/1996 | Queen et al. | |
| 5,545,806 A | 8/1996 | Lonberg et al. | |
| 5,545,807 A | 8/1996 | Surani et al. | |
| 5,569,825 A | 10/1996 | Lonberg et al. | |
| 5,585,089 A | 12/1996 | Queen et al. | |
| 5,625,126 A | 4/1997 | Lonberg et al. | |
| 5,633,425 A | 5/1997 | Lonberg et al. | |
| 5,661,016 A | 8/1997 | Lonberg et al. | |
| 5,693,762 A | 12/1997 | Queen et al. | |
| 5,698,797 A | 12/1997 | Fontanille et al. | |
| 5,770,429 A | 6/1998 | Lonberg et al. | |
| 5,789,650 A | 8/1998 | Lonberg et al. | |
| 5,814,318 A | 9/1998 | Onberg et al. | |
| 5,839,430 A | 11/1998 | Cama et al. | |
| 5,870,926 A | 2/1999 | Saito et al. | |
| 5,874,299 A | 2/1999 | Lonberg et al. | |
| 5,877,397 A | 3/1999 | Lonberg et al. | |
| 5,939,598 A | 8/1999 | Kucherlapati et al. | |
| 6,075,181 A | 6/2000 | Kucherlapati et al. | |
| 6,114,598 A | 9/2000 | Kucherlapati et al. | |
| 6,150,584 A | 11/2000 | Kucherlapati et al. | |
| 6,162,963 A | 12/2000 | Kucherlapati et al. | |
| 6,165,745 A | 12/2000 | Ward et al. | |
| 6,180,370 B1 | 1/2001 | Queen et al. | |
| 6,277,375 B1 | 8/2001 | Ward | |
| 6,358,058 B1 | 3/2002 | Strupat et al. | |
| 7,820,155 B2 | 10/2010 | Way | |
| 8,536,308 B2 | 9/2013 | Way | |
| 8,657,211 B2 | 2/2014 | Ueda et al. | |

(Continued)

FOREIGN PATENT DOCUMENTS

| | | |
|---|---|---|
| CN | 101346395 | 1/2009 |
| CN | 102224169 | 10/2011 |

(Continued)

OTHER PUBLICATIONS

Wypych J. et al. Human IgG2 Antibodies Display Disulfide-mediated Structural Isoforms. Journal of Biological Chemistry. 2008, 283:16194-16205 (Year: 2008).*
Dillon et al. Structural and functional characterization of disulfide isoforms of the human IgG2 subclass. J Biol Chem. Jun. 6, 2008; 283(23): 16206-16215 (Year: 2008).*
Paul. Fundamental Immunology, 3rd Edition, Raven Press, New York, Chapter 8, pp. 292-295, 1993 (Year: 1993).*
MacCallum et al. Antibody-antigen interactions: contact analysis and binding site topography. Journal of Molecular Biology, 262:732-745, 1996 (Year: 1996).*

(Continued)

*Primary Examiner* — Vanessa L. Ford
*Assistant Examiner* — Sandra E Dillahunt
(74) *Attorney, Agent, or Firm* — McDonnell Boehnen Hulbert & Berghoff LLP

(57) ABSTRACT

Featured herein are pharmaceutical compositions and formulations containing an interleukin-6 (IL-6) antagonist, e.g., an IL-6 antibody molecule, designed for administration for a subject. The pharmaceutical compositions and formulations provided herein are suitable for use in manufacture of medicaments or methods of treating subjects with IL-6 associated diseases, e.g., ocular diseases associated with elevated levels of IL-6.

19 Claims, 24 Drawing Sheets

Specification includes a Sequence Listing.

(56) References Cited

U.S. PATENT DOCUMENTS

| | | |
|---|---|---|
| 8,802,820 B2 | 8/2014 | Chamberlain et al. |
| 2003/0082630 A1 | 5/2003 | Kolkman et al. |
| 2003/0138417 A1* | 7/2003 | Kaisheva ............. C07K 16/249 |
| | | 424/130.1 |
| 2003/0157561 A1 | 8/2003 | Kolkman et al. |
| 2004/0009222 A1 | 1/2004 | Chou et al. |
| 2004/0191243 A1 | 9/2004 | Chen |
| 2007/0269868 A1 | 11/2007 | Carvalho Jensen et al. |
| 2008/0200655 A1 | 8/2008 | Sek |
| 2009/0130114 A1 | 5/2009 | Qian et al. |
| 2009/0202526 A1 | 8/2009 | Pons |
| 2009/0226530 A1 | 9/2009 | Lassner et al. |
| 2010/0034809 A1 | 2/2010 | Diefenbach-Streiber et al. |
| 2010/0187601 A1 | 7/2010 | Masuoka et al. |
| 2011/0045025 A1 | 2/2011 | Middaugh et al. |
| 2011/0171241 A1 | 7/2011 | Dix et al. |
| 2012/0005773 A1 | 1/2012 | Aasen et al. |
| 2012/0034212 A1* | 2/2012 | Bowen .................... A61P 19/06 |
| | | 435/254.2 |
| 2012/0121594 A1* | 5/2012 | Smith ..................... A61P 29/00 |
| | | 424/153.1 |
| 2014/0017244 A1 | 1/2014 | Duerr et al. |
| 2015/0017163 A1 | 1/2015 | Patel et al. |
| 2015/0125468 A1 | 5/2015 | Schmidt et al. |
| 2015/0239970 A1 | 8/2015 | Bee et al. |

FOREIGN PATENT DOCUMENTS

| | | | |
|---|---|---|---|
| CN | 102387814 | | 3/2012 |
| JP | 2015502959 A | | 1/2015 |
| JP | 2015519373 | | 7/2015 |
| JP | 2015527402 | | 9/2015 |
| WO | 199117271 A1 | | 11/1991 |
| WO | 199201047 A1 | | 1/1992 |
| WO | 199203918 A1 | | 3/1992 |
| WO | 199209690 A2 | | 6/1992 |
| WO | 199215679 A1 | | 9/1992 |
| WO | 199218619 A1 | | 10/1992 |
| WO | 199220791 A1 | | 11/1992 |
| WO | 199301288 A1 | | 1/1993 |
| WO | 199306213 A1 | | 4/1993 |
| WO | 199312227 A1 | | 6/1993 |
| WO | 1993011161 A1 | | 6/1993 |
| WO | 199413804 A1 | | 6/1994 |
| WO | 199425585 A1 | | 11/1994 |
| WO | 199627011 A1 | | 9/1996 |
| WO | 19973461 A1 | | 1/1997 |
| WO | 199713852 A1 | | 4/1997 |
| WO | 199823289 A1 | | 6/1998 |
| WO | 199824884 A1 | | 6/1998 |
| WO | 199850431 A2 | | 11/1998 |
| WO | 199945962 A1 | | 9/1999 |
| WO | 200034784 A1 | | 6/2000 |
| WO | 200114424 A2 | | 3/2001 |
| WO | 200243478 A2 | | 6/2002 |
| WO | WO 03039485 | | 5/2003 |
| WO | 2004045507 A2 | | 6/2004 |
| WO | 2005062955 | | 7/2005 |
| WO | 2006020114 | | 2/2006 |
| WO | 2006028936 A2 | | 3/2006 |
| WO | 2007076927 A1 | | 7/2007 |
| WO | 2007104529 | | 9/2007 |
| WO | 2008144763 A2 | | 11/2008 |
| WO | 2010060768 | | 6/2010 |
| WO | WO 2010088444 | | 8/2010 |
| WO | 2012007896 | | 1/2012 |
| WO | 2013086448 A2 | | 6/2013 |
| WO | WO 2013181495 | | 12/2013 |
| WO | WO 2014039903 | | 3/2014 |
| WO | 2014074905 A1 | | 5/2014 |
| WO | WO 2014074905 | | 5/2014 |
| WO | WO-2014074905 A1 * | 5/2014 | ............ A61K 39/395 |
| WO | 2015110556 A1 | | 7/2015 |
| WO | WO-2016073890 A1 * | 5/2016 | ............ A61K 9/0048 |
| WO | WO 2016073894 | | 5/2016 |

OTHER PUBLICATIONS

Casset et al. A peptide mimetic of an anti-CD4 monoclonal antibody by rational design. Biochemical and Biophysical Research Communications, 307:198-205, 2003 (Year: 2003).*

Vajdos et al. Comprehensive Functional Maps of the Antigen-binding Site of an Anti-ErbB2 Antibody Obtained with Shotgun Scanning Mutagenesis. Journal of Molecular Biology, Jul. 5, 2002;320(2):415-28 (Year: 2002).*

Brown et al. Tolerance of single, but not multiple, amino acid replacements in antibody VH CDR 2: a means of minimizing B cell wastage from somatic hypermutation? Journal of Immunology. May 1996; 156(9):3285-91 (Year: 1996).*

Rudikoff et al. Single amino acid substitutoin altering antigen-binding specificity. Proc. Natl. Acad. Sci. USA, 79(6):1979-1983, Mar. 1982 (Year: 1982).*

Fischer et al. The Two Faces of IL-6 in the Tumor Microenvironment. Semin Immunol. Feb. 2014; 26(1): 38-47 (Year: 2014).*

Hume et al. A Protective Role for IL-6 in Staphylococcal Microbial Keratitis. Investigative Ophthalmology & Visual Science, Nov. 2006, vol. 47, No. 11 (Year: 2006).*

Song et al. Antitumor efficacy of the anti-interleukin-6 (IL-6) antibody siltuximab in mouse xenograft models of lung cancer. J Thorac Oncol. Jul. 2014 ; 9(7): 974-982 (Year: 2014).*

Dorff et al. Clinical and Correlative Results of SWOG S0354: A Phase II Trial of CNTO328 (Siltuximab), a Monoclonal Antibody against Interleukin-6, in Chemotherapy-Pretreated Patients with Castration-Resistant Prostate Cancer. Clin Cancer Res; 16(11); 3028-34 (Year: 2010).*

Choy et al. Translating IL-6 biology into effective treatments. Nat Rev Rheumatol 16, 335-345 (2020) (Year: 2020).*

Sieper et al. Assessment of short-term symptomatic efficacy of tocilizumab in ankylosing spondylitis: results of randomised, placebo-controlled trials.. Ann Rheum Dis 2014; 73:95-100 (Year: 2014).*

Rovin et al. A Multicenter, Randomized, Double-Blind, Placebo-Controlled Study to Evaluate the Efficacy and Safety of Treatment With Sirukumab (CNTO 136) in Patients With Active Lupus Nephritis. Arthritis Rheumatol. Sep. 2016; 68(9): 2174-2183 (Year: 2016).*

Mesquida et al. Interleukin-6 blockade in ocular inflammatory diseases. Clin Exp Immunol. Jun. 2014; 176(3): 301-309 (Year: 2014).*

Abaza et al., "Effects of amino acid substitutions outside an antigenic site on protein binding to monoclonal antibodies of predetermined specificity obtained by peptide immunization: demonstration with region 94-100 (antigenic site 3) of myoglobin," J. Prat. Chem., 11 :433-444 (1992).

Brown, et al, "Tolerance of single, but not multiple, amino acid replacements in antibody VH CDR 2: a means of minimizing B cell wastage from somatic hypermutation?" J Immunol., 156(9):3285-91 (1996).

Casset et al., "A peptide mimetic of an anti-CD4 monoclonal antibody by rational design," Biochemical and Biophysical Research Communications, 307: 198-205 (2003).

Colman, "Effects of amino acid sequence changes on antibody-antigen interactions," Research in Immunology, 145:33-36 (1994).

Dondelinger et al., "Understanding the Significance and Implications of Antibody Numbering and Antigen-Binding Surface/Residue Definition," Front. Immunol., Oct. 16, 2018, p. 1-15.

Maccallum et al., "Antibody-antigen interactions: contact analysis and binding site topography," Journal of Molecular Biology, 262:732-745, 1996 (1996).

Mcguinness et al., "Class 1 outer membrane protein of Neisseria meningitidis: epitope analysis of the antigenic diversity between strains, implications for subtype definition and molecular epidemiology," Mol. Microbiol., 7:505-514 (1993).

(56) References Cited

OTHER PUBLICATIONS

Moudallal et al., "Monoclonal antibodies as probes of the antigenic structure of tobacco mosaic virus," EMBO Journal, 1: 1005-1010 (1982).
Paul, Fundamental Immunology, 3rd Edition, Raven Press, New York, Chapter 8, pp. 292-295 (1993).
Rudikoff, S., et al., "Single amino acid substitution altering antigen-binding specificity", Proceedings of the National Academy of Sciences, 79:1979-1983 (1982).
Agarwal et al., "Rodent Models of Experimental Autoimmune Uveitis" Methods in Mol Biol, 900:443-469 (2012).
Altschul, et al "Basic Local Alignment Search Tool" J. Mol. Biol. (1990) 215:403-410.
Altschul, et al "Gapped BLAST and PSI-BLAST: a new generation of protein database search programs" Nucleic Acids Research (1997) 25(17):3389-3402.
Asquith et al., "Animal models of Rheumatiod Arthritis" Euro. J. Immunol (2009) 39:2040-2044.
Barbas, et al., "Assembly of combinatorial antibody libraries on phage surfaces: The gene III site." PNAS USA (1991) 88:7978-7982.
Boder et al., "Directed evolution of antibody fragments with monovalent femtomolar antigen-binding affinity" PNAS USA (2000) 97:10701-10705.
Caspi et al., "Understanding Autoimmune Uveitis through Animal Models." Investigative Opthamology Visual Science (2011) 52(3):1873-1879.
Chao et al., "Isolating and engineering human antibodies using yeast surface display" Nature Protocols (2006) 1:755-768.
Chothia et al, "Canonical Structures for the Hypervariable Regions of Immunoglobulins" J. Mol. Biol (1987) 196:901-917.
Chothia et al, "Conformations of immunoglobulin hypervariable regions" Nature (1989) 342:878-883.
Einmahl et al., "Therapeutic applications of viscous and injectable poly(ortho esters)" Advanced Drug Delivery Reviews (2001) 53:45-73.
Finch et al., "Whole-Molecule Antibody Engineering: Generation of a High-Affinity Anti-IL-6 Antibody with Extended Pharmacokinetics," Journal of Molecular Biology (2011) 411:791-807.
Funatsu, et al "Vitreous levels of interleukin-6 and vascular endothelial growth factor are related to diabetic macular edema" Ophthalmology (2003) 110(9):1690-1696.
Ghelardi et al., "A Mucoadhesive Polymer Extracted from Tamarind Seed Improves the Intraocular Penetration and Efficacy of Rufloxacin in Topical Treatment of Experimental Bacterial Keratitis" Antimicrobial Agents and Chermotherapy (2004) 48(9):3396-3401.
Gram et al., "In vitro selection and affinity maturation of antibodies from a naive combinatorial immunoglobulin library." PNAS USA (1992) 89:3576-3580.
Griffiths et al., "Human anti-self antibodies with high specificity from phage display libraries." The EMBO Journal (1993) 12(2):725-734.
Haruta et al., "Blockade of Interleukin-6 Signaling Suppresses Not Only Th17 but Also Interphotoreceptor Retinoid Binding Protein-Specific Th1 by Promoting Regulatory T Cells in Experimental Autoimmune Uveoretinitis." Invest. Opthal. Vis. Sci. (2011) 52(6):3264-3271.
Hawkins et al., "Selection of phage antibodies by binding affinity: Mimicking affinity maturation." Journal of Molecular Biology (1992) 226(3):889-896.
Hoogenboom et al. "Multi-subunit proteins on the surface of filamentour phage: methodologies for displaying antibody (Fab) heavy and light chains" Nucl. Acids. Res. (1991) 19(15):4133-4137.
Huse, et al., "Generation of a Large Combinatorial Library of the Immunoglobulin Repertoire in Phage Lambda." Science (1989) 246:1275-1281.
Chang and Hershenson (2002). "Practical approaches to protein formulation development." In "Rational Design of Stable Protein Formulations—Theory and Practice" (J.F. Carpenter and M.C. Manning, eds.) Kluwer Academic/Plenum Publishers, New York, pp. 11-25.
Brown, et al, "Tolerance of single, but not multiple, amino acid replacements in antibody VH CDR 2: a means of minimizing B cell wastage from somatic hypermutation?" J Immunol., 156(9):3285-91 (1998).
Chien, N., et al., "Significant structural and functional change of an antigen-binding site by a distant amino acid substitution: Proposal of a structural mechanism", Proceedings of the National Academy of Sciences, 86:5532-5536 (1989).
Dillon et al., "Structural and functional characterization of disulfide isoforms of the human IgG2 subclass," J Biol Chem. 283(23):16206-15 (2008).
Fisher et al., "The two faces of IL-6 in the tumor microenvironment," Semin Immunol., 26(1):38-47 (2014).
Hume et al., "A protective role for IL-6 in staphylococcal microbial keratitis," Invest Ophthalmol Vis Sci. 47(11):4926-30 (2006).
International Search Report for PCT/US2013/069279, date of mailing Mar. 7, 2014.
Zumi-Nagai et al., "Interleukin-6 Receptor-Mediated Activation of Signal Transducer and Activator of Transcription-3 (STAT3) Promotes Choroidal Neovascularization" American Journal of Pathology (2007) 170(6):2149-2158.
Kalai et al., "Analysis of the mechanism of action of anti-human interleukin-6 and anti-human interleukin-6 receptor-neutralising monoclonal antibodies" Eur. J. Biochem. (1997) 249:690-700.
Kauffman et al., "Cytokines in Vitreous Humor: Interleukin-6 is Elevated in Proliferative Vitreoretinopathy" Invest Opthalmol Vis Sci (1994) 35(3):900-906.
Kohler et al, "Continuous cultures of fused cells secreting antibody of predefined specificity" Nature, 256:495-497 (1975).
Krzystolik et al., "Prevention of Experimental Choroidal Neovascularization with Intravitreal Anti-Vascular Endothelial Growth Factor Antibody Fragment" Arch Ophthalmol (2002) 120:338-346.
Lacroix, Marine et al. "Novel Insights into Interleukin 6 (IL-6) Cis- and Transsignaling Pathways by Differentially Manipulating the Assembly of the IL-6 Signaling Complex*", J. Bioi. Chern., Nov. 6, 2015; 290{45}:26943-53.
Lissilaa, Rami et al. "Although IL-6 Trans-Signaling Is Sufficient To Drive Local Immune Responses, Classical IL-6 Signaling Is Obligate for the Induction of T Cell-Mediated Autoimmunity", J. Immunol., 2010, 185 (9) 5512-5521.
Magdelaine-Beuzelin, et al., "Therapeutic antibodies in ophthalmology: Old is new again", mAbs, 2:176-180 (2010).
Martin et al., "Crystal Structure at 2.8 A of an FcRn/Heterodimeric Fc Complex: Mechanism of pH-Dependent Binding" Molecular Cell (2001) 7:867-877.
Miao et al., "Inflammatory cytokines in aqueous humor of patients with choroidal neovascularization" Molecular Vision (2012) 18:574-580.
Murray et al., Biokhimiya cheloveka, «Mir», LANGE Medical book 1993, v. 1, p. 34.
Noma et al., "Aqueous humour levels of cytokines are correlated to vitreous levels and severity of macular oedema in branch retinal vein occlusion" Eye (2008) 22:42-48.
Padlan et al., "Identification of specificity-determining residues in antibodies," FASEB J, 9:133-139 (1995).
Panka, David J et al. "Defining the structural correlates responsible for loss of arsonate affinity in an IDCR antibody isolated from an autoimmune mouse" Mol Immunol. Aug. 1993; 30(11):1013-20.
Pearson, "Effective protein sequence comparison" Methods of Enzymology (1996) 266:227-268.
Pearson, "Empirical statistical estimates for sequence similarity searches" Journal of Molecular Biology (1998) 276 (1):71-84.
Pearson, W., "Rapid and Sensitive Sequence Comparison with FASTP and FASTA" Methods Enzymol (1990) 183:63-98.
Rose-John, Stefan et al. "IL-6 Trans-Signaling via the Soluble IL-6 Receptor: Importance for the Pro-Inflammatory Activities of IL-6", International Journal of Biological Sciences, 2012;8(9):1237-1247.
Rudikoff et al., "Single amino acid substitution altering antigen-binding specificity,", Proceedings of the National Academy of Sciences, 1982, pp. 1979-1983, vol. 79.

(56) References Cited

OTHER PUBLICATIONS

Tamura et al., "Structural correlates of an anticarcinoma antibody: identification of specificity-determining residues (SDRs) and development of a minimally immunogenic antibody variant by retention of SDRs only," J Immunol., 164:1432-1441 (2000).

Tenhumberg, et al. "Structure-guided Optimization of the Interleukin-6 Trans-signaling Antagonist," Journal of Biological Chemistry, 283:27200-27207 (2008).

Tomizuka et al., "Double trans-chromosomic mice: Maintenance of two individual human chromosome fragments containing Ig heavy and k loci and expression of fully human antibodies." PNAS USA (2000) 97:722-727.

Tultseva S.N. et al., The role of inflammation in the pathogenesis of post-thrombotic macular edema. Modern directions of drug treatment, Ophthalmological statements, 2012, vol. 5 (see pp. 37-40).

Vajdos, et al., "Comprehensive Functional Maps of the Antigen-binding Site of an Anti-ErbB2 Antibody Obtained with Shotgun Scanning Mutagenesis", J. Mol. Biol, 320:415-428 (2002).

Wilson et al., "Assessing annotation transfer for genomics: quantifying the relations between protein sequence, structure and function through traditional and probabilistic scores," J Mol Biol. (2000) 297, 233-249.

Winkler, K., et al., "Changing the antigen binding specificity by single point mutations of an anti-p24 (HIV-1) antibody", The journal of Immunology, 165:4505-4514 (2000).

Yoshimura et al., "Involvement of Th17 cells and the effect of anti-IL-6 therapy in autoimmune uveitis." Rheum. (2009) 48:347-354.

Yuuki et al, "Inflammatory cytokines in vitreous fluid and serum of patients with diabetic vitreoretinopathy" Journal of Diabetes and its Complications (2001) 15(5):257-259.

\* cited by examiner

```
                    FR1              CDR1       FR1        CDR2      FR3
          ◄─────────────────►  ◄─────►  ◄──────────►  ◄─────►  ◄─────►
               10        20        30        40        50        60        70
          ....|....|....|....|....|....|....|....|....|....|....|....|....|....|
EBI-029   QVQLVQSGAEVKKPGSSVKVSCKASGYALSNYLIEWVRQAPGQGLEWMGVITPGSTINYAQKFQGRVTI
EBI-030   QVQLVQSGAEVKKPGSSVKVSCKASGYALSNYLIEWVRQAPGQGLEWMGVITPGSTINYAQKFQGRVTI
EBI-031   QVQLVQSGAEVKKPGSSVKVSCKASGYALSNYLIEWVRQAPGQGLEWMGVITPGSTINYAQKFQGRVTI
                    FR3                 CDR3      FR4         CH1
          ◄─────────────────────►  ◄──────►  ◄────►  ◄──────────────►
               80        90       100       110       120       130       140
          ....|....|....|....|....|....|....|....|....|....|....|....|....|....|
EBI-029   TADESTSTAYMELSSLRSEDTAVYYCARSRWDPLYYYALEWGQGTTVTVSSASTKGPSVFPLAPCSRST
EBI-030   TADESTSTAYMELSSLRSEDTAVYYCARSRWDPLYYYALEWGQGTTVTVSSASTKGPSVFPLAPCSRST
EBI-031   TADESTSTAYMELSSLRSEDTAVYYCARSRWDPLYYYALEWGQGTTVTVSSASTKGPSVFPLAPCSRST
                                           CH1
          ◄──────────────────────────────────────────────────────────────────►
               150       160       170       180       190       200       210
          ....|....|....|....|....|....|....|....|....|....|....|....|....|....|
EBI-029   SESTAALGCLVKDYFPEPVTVSWNSGALTSGVHTFPAVLQSSGLYSLSSVVTVPSSNFGTQTYTCNVDHK
EBI-030   SESTAALGCLVKDYFPEPVTVSWNSGALTSGVHTFPAVLQSSGLYSLSSVVTVPSSNFGTQTYTCNVDHK
EBI-031   SESTAALGCLVKDYFPEPVTVSWNSGALTSGVHTFPAVLQSSGLYSLSSVVTVPSSNFGTQTYTCNVDHK
            CH1      Hinge                     CH2
          ◄────►  ◄────────►  ◄──────────────────────────────────────►
               220       230       240       250       260       270       280
          ....|....|....|....|....|....|....|....|....|....|....|....|....|....|
EBI-029   PSNTKVDKTVERKCCVECPPCPAPPVAGPSVFLFPPKPKDTLMISRTPEVTCVVVDVSHEDPEVQFNWYV
EBI-030   PSNTKVDKTVERKCCVECPPCPAPPVAGPSVFLFPPKPKDTLMISRTPEVTCVVVDVSHEDPEVQFNWYV
EBI-031   PSNTKVDKTVERKCCVECPPCPAPPVAGPSVFLFPPKPKDTLMISRTPEVTCVVVDVSHEDPEVQFNWYV
                                    CH2                                  CH1
          ◄────────────────────────────────────────────────────────►  ◄─────►
               290       300       310       320       330       340       350
          ....|....|....|....|....|....|....|....|....|....|....|....|....|....|
EBI-029   DGVEVHNAKTKPREEQFNSTFRVVSVLTVVHQDWLNGKEYKCKVSNKGLPAPIEKTISKTKGQPREPQVY
EBI-030   DGVEVHNAKTKPREEQFNSTFRVVSVLTVVHQDWLNGKEYKCKVSNKGLPAPIEKTISKTKGQPREPQVY
EBI-031   DGVEVHNAKTKPREEQFNSTFRVVSVLTVVHQDWLNGKEYKCKVSNKGLPAPIEKTISKTKGQPREPQVY
                                           CH3
          ◄──────────────────────────────────────────────────────────────────►
               360       370       380       390       400       410       420
          ....|....|....|....|....|....|....|....|....|....|....|....|....|....|
EBI-029   TLPPSREEMTKNQVSLTCLVKGFYPSDIAVEWESNGPENNYKTTPPLDSDGSFFLYSKLTVDKSRWQQ
EBI-030   TLPPSREEMTKNQVSLTCLVKGFYPSDIAVEWESNGPENNYKTTPPLDSDGSFFLYSKLTVDKSRWQQ
EBI-031   TLPPSREEMTKNQVSLTCLVKGFYPSDIAVEWESNGPENNYKTTPPLDSDGSFFLYSKLTVDKSRWQQ
                     CH3
          ◄──────────────────►
               430       440
          ....|....|....|....|....|....
EBI-029   GNVFSCSVMHEALHNHYTQKSLSLSPGK    (SEQ ID NO: 1)
EBI-030   GNVFSCSVMHEALHNHYTQKSLSLSPGK    (SEQ ID NO: 13)
EBI-031   GNVFSCSVMHEALHNHYTQKSLSLSPGK    (SEQ ID NO: 25)
```

FIG. 1A

| Sample | Description | Main Peak RT | Main Peak Area | Total Area | Main Peak % | % HMW Peak-1 | % HMW Peak-2 | % LMW |
|---|---|---|---|---|---|---|---|---|
| 1 | | 3.510 | 14905140 | 15147546 | 98.40 | 0.29 | 1.31 | |
| 2 | | 3.513 | 14971391 | 15214949 | 98.40 | 0.29 | 1.31 | |
| 3 | | 3.512 | 14946006 | 15188518 | 98.40 | 0.29 | 1.31 | |
| 4 | | 3.504 | 14964479 | 15209234 | 98.39 | 0.30 | 1.31 | |
| 5 | Ref Std Protein A | 3.508 | 14882671 | 15124080 | 98.40 | 0.29 | 1.31 | |
| 6 | Eluate 03/10/15 BL | 3.509 | 14832215 | 15072272 | 98.41 | 0.29 | 1.30 | |
| 7 | | 3.505 | 14841949 | 15083433 | 98.40 | 0.29 | 1.31 | |
| 8 | | 3.507 | 15143545 | 15386739 | 98.42 | 0.29 | 1.29 | |
| 9 | | 3.511 | 15132747 | 15374408 | 98.43 | 0.28 | 1.29 | |
| 10 | | 3.511 | 15093372 | 15335630 | 98.42 | 0.29 | 1.29 | |
| | Mean | 3.509 | 14971352 | 15213681 | 98.407 | 0.290 | 1.303 | |
| | St Dev | 0.003 | 115291.85 | 115792.72 | 0.013 | 0.005 | 0.009 | |
| | % RSD | 0.085 | 0.770 | 0.761 | 0.013 | 1.626 | 0.728 | |

| Sample | Description | Main Peak RT | Main Peak Area | Total Area | Main Peak % | % HMW Peak-1 | % HMW Peak-2 | % LMW |
|---|---|---|---|---|---|---|---|---|
| | Start Material (T = 7) | 3.505 | 16489595 | 17288111 | 95.38 | 0.48 | 4.13 | 0.01 |
| | Start Material (T = 0) | 3.497 | 15148333 | 15574736 | 97.26 | 0.31 | 2.43 | |

| |
|---|
| > 96.5% |
| 96.0-96.5% |
| 95.0-96.0% |
| 94.0-95.0% |
| < 94% |

FIG. 3A

| Buffer | NaCl (mM) | Sample | Description | Main Peak RT | Main Peak Area | Total Area | Main Peak % | % HMW Peak-1 | % HMW Peak-2 | % LMW |
|---|---|---|---|---|---|---|---|---|---|---|
| Acetate pH 5.5 | 20 | 1A | 10% Sucrose | | | | | | | |
| | | 2A | 5% Sorbitol | | | | | | | |
| | | 3A | 0.1% Tween-20 | 3.507 | 14706159 | 15394670 | 95.53 | 0.65 | 3.82 | |
| | | 4A | 0.1% Tween-80 | 3.511 | 15681600 | 16426135 | 95.47 | 0.52 | 4.01 | |
| | | 5A | 0.1% Poloxamer | 3.505 | 16821147 | 17639887 | 95.36 | 0.53 | 4.11 | |
| | | 6A | 0.2 M Arginine | 3.505 | 16898623 | 17531035 | 96.39 | 0.47 | 3.14 | |
| | 150 | 7A | 10% Sucrose | | | | | | | |
| | | 8A | 5% Sorbitol | 3.506 | 14823339 | 15430440 | 96.07 | 0.44 | 3.5 | |
| | | 9A | 0.1% Tween-20 | 3.506 | 17853169 | 18665711 | 95.65 | 0.63 | 3.72 | |
| | | 10A | 0.1% Tween-80 | 3.512 | 17566935 | 18409347 | 95.42 | 0.57 | 4.01 | |
| | | 11A | 0.1% Poloxamer | 3.505 | 24871971 | 26237695 | 94.79 | 0.62 | 4.58 | |
| | | 12A | 0.2 M Arginine | 3.509 | 27302271 | 28370857 | 96.23 | 0.56 | 3.2 | |
| Citrate pH 6.0 | 20 | 1B | 10% Sucrose | | | | | | | |
| | | 2B | 5% Sorbitol | 3.510 | 19381619 | 20159528 | 96.14 | 0.46 | 3.4 | |
| | | 3B | 0.1% Tween-20 | 3.511 | 15520799 | 16310068 | 95.16 | 0.84 | 4 | |
| | | 4B | 0.1% Tween-80 | 3.506 | 15572895 | 16376141 | 95.10 | 0.57 | 4.33 | |
| | | 5B | 0.1% Poloxamer | 3.509 | 15987344 | 16773618 | 95.31 | 0.57 | 4.12 | |
| | | 6B | 0.2 M Arginine | 3.511 | 5105525 | 5248789 | 97.27 | 0.36 | 2.37 | |
| | 150 | 7B | 10% Sucrose | 3.506 | 19786285 | 20659187 | 95.77 | 0.48 | 3.74 | |
| | | 8B | 5% Sorbitol | 3.504 | 17038291 | 17762072 | 95.93 | 0.45 | 3.63 | |
| | | 9B | 0.1% Tween-20 | 3.504 | 15433181 | 16119065 | 95.74 | 0.74 | 3.52 | |
| | | 10B | 0.1% Tween-80 | 3.503 | 14854514 | 15523432 | 95.69 | 0.57 | 3.74 | 0.01 |
| | | 11B | 0.1% Poloxamer | 3.505 | 16574534 | 17469187 | 94.88 | 0.62 | 4.5 | 0.01 |
| | | 12B | 0.2 M Arginine | 3.506 | 15079590 | 15596914 | 96.68 | 0.51 | 2.81 | |

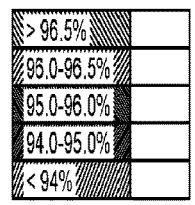

FIG. 3B

| Buffer | NaCl (mM) | Sample | Description | Main Peak RT | Main Peak Area | Total Area | Main Peak % | % HMW Peak-1 | % HMW Peak-2 | % LMW |
|---|---|---|---|---|---|---|---|---|---|---|
| Citrate pH 6.5 | 20 | 1C | 10% Sucrose | 3.504 | 23627570 | 24867026 | 95.02 | 0.53 | 4.46 | |
| | | 2C | 5% Sorbitol | 3.505 | 17199208 | 17893285 | 96.12 | 0.45 | 3.43 | |
| | | 3C | 0.1% Tween-20 | 3.507 | 16178040 | 17021882 | 95.04 | 0.86 | 4.09 | |
| | | 4C | 0.1% Tween-80 | 3.506 | 15203735 | 15988834 | 95.09 | 0.64 | 4.27 | |
| | | 5C | 0.1% Poloxamer | 3.506 | 15198141 | 15914225 | 95.50 | 0.57 | 3.92 | |
| | | 6C | 0.2 M Arginine | 3.508 | 17143243 | 17789348 | 96.37 | 0.48 | 3.15 | |
| | 150 | 7C | 10% Sucrose | 3.506 | 22185601 | 23247871 | 95.43 | 0.52 | 4.05 | |
| | | 8C | 5% Sorbitol | 3.509 | 17230610 | 17982214 | 95.82 | 0.46 | 3.72 | |
| | | 9C | 0.1% Tween-20 | 3.510 | 15520952 | 16267220 | 95.41 | 0.85 | 3.73 | |
| | | 10C | 0.1% Tween-80 | 3.512 | 16187173 | 16918281 | 95.68 | 0.6 | 3.72 | |
| | | 11C | 0.1% Poloxamer | 3.511 | 15135325 | 15942423 | 94.94 | 0.63 | 4.43 | 0.01 |
| | | 12C | 0.2 M Arginine | 3.507 | 16440347 | 17009347 | 96.65 | 0.52 | 2.82 | |
| Histidine pH 6.5 | 20 | 1D | 10% Sucrose | 3.509 | 22062138 | 22926723 | 96.23 | 0.44 | 3.33 | |
| | | 2D | 5% Sorbitol | 3.511 | 17752953 | 18362375 | 96.68 | 0.42 | 2.9 | |
| | | 3D | 0.1% Tween-20 | 3.505 | 15781814 | 16391826 | 96.28 | 0.71 | 3.01 | |
| | | 4D | 0.1% Tween-80 | 3.509 | 15191034 | 15792254 | 96.19 | 0.52 | 3.29 | |
| | | 5D | 0.1% Poloxamer | 3.505 | 15939466 | 16561375 | 96.24 | 0.48 | 3.27 | |
| | | 6D | 0.2 M Arginine | 3.503 | 14586628 | 15064037 | 96.83 | 0.47 | 2.7 | |
| | 150 | 7D | 10% Sucrose | 3.511 | 21546739 | 22371936 | 96.31 | 0.46 | 3.23 | |
| | | 8D | 5% Sorbitol | 3.508 | 18847453 | 19500640 | 96.65 | 0.45 | 2.9 | |
| | | 9D | 0.1% Tween-20 | 3.510 | 16176394 | 16806543 | 96.25 | 0.79 | 2.96 | |
| | | 10D | 0.1% Tween-80 | 3.509 | 15285723 | 15835859 | 96.53 | 0.53 | 2.94 | |
| | | 11D | 0.1% Poloxamer | 3.510 | 15575637 | 16166640 | 96.34 | 0.52 | 3.13 | |
| | | 12D | 0.2 M Arginine | 3.509 | 15174625 | 15602254 | 96.96 | 0.46 | 2.56 | 0.02 |

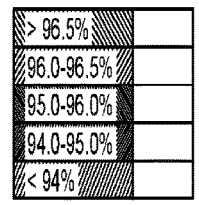

| | |
|---|---|
| > 96.5% | |
| 96.0-96.5% | |
| 95.0-96.0% | |
| 94.0-95.0% | |
| < 94% | |

FIG. 3C

| Buffer | NaCl (mM) | Sample | Description | Main Peak RT | Main Peak Area | Total Area | Main Peak % | % HMW Peak-1 | % HMW Peak-2 | % LMW |
|---|---|---|---|---|---|---|---|---|---|---|
| Phosphate pH 6.5 | 20 | 1E | 10% Sucrose | 3.509 | 24786067 | 26060277 | 95.11 | 0.55 | 4.34 | |
| | | 2E | 5% Sorbitol | 3.507 | 20643089 | 21482455 | 96.09 | 0.52 | 3.39 | |
| | | 3E | 0.1% Tween-20 | 3.505 | 16567257 | 17349249 | 95.49 | 0.79 | 3.72 | |
| | | 4E | 0.1% Tween-80 | 3.503 | 15384149 | 16159512 | 95.20 | 0.59 | 4.21 | |
| | | 5E | 0.1% Poloxamer | 3.506 | 15479597 | 16218724 | 95.44 | 0.58 | 3.98 | |
| | | 6E | 0.2 M Arginine | 3.510 | 16395417 | 16974469 | 96.59 | 0.51 | 2.9 | |
| | 150 | 7E | 10% Sucrose | 3.505 | 23276612 | 24412587 | 95.35 | 0.49 | 4.16 | |
| | | 8E | 5% Sorbitol | 3.510 | 17682485 | 18387091 | 96.17 | 0.46 | 3.37 | |
| | | 9E | 0.1% Tween-20 | 3.511 | 16553413 | 17302875 | 95.67 | 0.8 | 3.53 | |
| | | 10E | 0.1% Tween-80 | 3.504 | 15985452 | 16681659 | 95.83 | 0.55 | 3.62 | |
| | | 11E | 0.1% Poloxamer | 3.504 | 16149140 | 16924843 | 95.42 | 0.56 | 4.03 | |
| | | 12E | 0.2 M Arginine | 3.506 | 16482818 | 17037944 | 96.74 | 0.48 | 2.77 | 0.01 |
| Phosphate pH 7.0 | 20 | 1F | 10% Sucrose | 3.508 | 22602568 | 24026757 | 94.07 | 0.59 | 5.34 | |
| | | 2F | 5% Sorbitol | 3.504 | 16256199 | 16995750 | 95.65 | 0.51 | 3.84 | |
| | | 3F | 0.1% Tween-20 | 3.503 | 15753173 | 16563389 | 95.11 | 0.78 | 4.11 | |
| | | 4F | 0.1% Tween-80 | 3.510 | 3882230 | 4042427 | 96.04 | 0.61 | 3.35 | |
| | | 5F | 0.1% Poloxamer | 3.509 | 15357444 | 16178532 | 94.92 | 0.62 | 4.46 | |
| | | 6F | 0.2 M Arginine | 3.503 | 17290129 | 17922622 | 96.47 | 0.53 | 3 | |
| | 150 | 7F | 10% Sucrose | 3.508 | 22504892 | 23744386 | 94.78 | 0.55 | 4.67 | |
| | | 8F | 5% Sorbitol | 3.504 | 16365064 | 17085925 | 95.78 | 0.51 | 3.71 | |
| | | 9F | 0.1% Tween-20 | 3.511 | 16242026 | 17055496 | 95.23 | 0.84 | 3.93 | |
| | | 10F | 0.1% Tween-80 | 3.507 | 15216524 | 15984898 | 95.19 | 0.76 | 4.04 | 0.01 |
| | | 11F | 0.1% Poloxamer | 3.506 | 15832045 | 16711604 | 94.74 | 0.68 | 4.58 | 0.01 |
| | | 12F | 0.2 M Arginine | 3.507 | 16912591 | 17527959 | 96.49 | 0.55 | 2.95 | 0.02 |

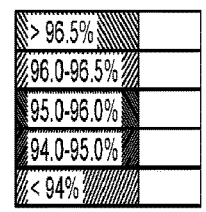

| | |
|---|---|
| > 96.5% | |
| 96.0-96.5% | |
| 95.0-96.0% | |
| 94.0-95.0% | |
| < 94% | |

FIG. 3D

| Buffer | NaCl (mM) | Sample | Description | Main Peak RT | Main Peak Area | Total Area | Main Peak % | % HMW Peak-1 | % HMW Peak-2 | % LMW |
|---|---|---|---|---|---|---|---|---|---|---|
| Phosphate pH 7.5 | 20 | 1G | 10% Sucrose | 3.507 | 23523005 | 25329834 | 92.87 | 0.75 | 6.37 | 0.01 |
| | | 2G | 5% Sorbitol | 3.507 | 16549100 | 17455194 | 94.81 | 0.6 | 4.59 | 0.01 |
| | | 3G | 0.1% Tween-20 | 3.510 | 15599945 | 16547210 | 94.28 | 0.92 | 4.8 | 0.01 |
| | | 4G | 0.1% Tween-80 | 3.507 | 15278318 | 16393285 | 93.20 | 1.21 | 5.58 | 0.01 |
| | | 5G | 0.1% Poloxamer | 3.508 | 15436235 | 16404358 | 94.10 | 0.83 | 5.06 | 0.01 |
| | | 6G | 0.2 M Arginine | 3.511 | 16709661 | 17370550 | 96.20 | 0.66 | 3.1 | 0.04 |
| | 150 | 7G | 10% Sucrose | 3.503 | 21622400 | 22977557 | 94.10 | 0.67 | 5.22 | 0.01 |
| | | 8G | 5% Sorbitol | 3.509 | 26806029 | 28341426 | 94.58 | 0.69 | 4.72 | 0.01 |
| | | 9G | 0.1% Tween-20 | 3.504 | 16012437 | 16899885 | 94.75 | 0.91 | 4.33 | 0.01 |
| | | 10G | 0.1% Tween-80 | 3.505 | 14719780 | 15675158 | 93.91 | 1.35 | 4.72 | 0.02 |
| | | 11G | 0.1% Poloxamer | 3.509 | 15392052 | 16363883 | 94.06 | 0.83 | 5.09 | 0.02 |
| | | 12G | 0.2 M Arginine | 3.504 | 16145328 | 16844413 | 95.85 | 0.71 | 3.38 | 0.06 |
| Tricine pH 8.5 | 20 | 1H | 10% Sucrose | 3.509 | 7752112 | 8095023 | 95.77 | 0.53 | 3.59 | 0.11 |
| | | 2H | 5% Sorbitol | 3.505 | 16530261 | 17591589 | 93.97 | 0.81 | 5.16 | 0.06 |
| | | 3H | 0.1% Tween-20 | 3.502 | 12918526 | 13866910 | 93.16 | 1.1 | 5.58 | 0.16 |
| | | 4H | 0.1% Tween-80 | 3.509 | 14002677 | 15013742 | 93.27 | 1.11 | 5.55 | 0.08 |
| | | 5H | 0.1% Poloxamer | 3.509 | 15868675 | 17163583 | 92.46 | 1.11 | 6.23 | 0.2 |
| | | 6H | 0.2 M Arginine | 3.500 | 17124452 | 18008651 | 95.09 | 1.08 | 3.4 | 0.43 |
| | 150 | 7H | 10% Sucrose | 3.508 | 20187627 | 21605706 | 93.44 | 0.85 | 5.6 | 0.12 |
| | | 8H | 5% Sorbitol | 3.509 | 11240167 | 11799099 | 95.26 | 0.73 | 3.97 | 0.04 |
| | | 9H | 0.1% Tween-20 | 3.504 | 14654274 | 15617007 | 93.84 | 1.23 | 4.83 | 0.1 |
| | | 10H | 0.1% Tween-80 | 3.507 | 13898969 | 14846054 | 93.62 | 1.12 | 5.1 | 0.16 |
| | | 11H | 0.1% Poloxamer | 3.510 | 14397923 | 15462067 | 93.12 | 1.08 | 5.68 | 0.12 |
| | | 12H | 0.2 M Arginine | 3.506 | 15924785 | 16702360 | 95.34 | 1.12 | 3.23 | 0.31 |

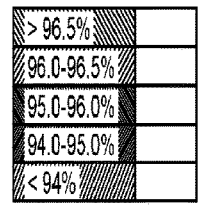

| | |
|---|---|
| > 96.5% | |
| 96.0-96.5% | |
| 95.0-96.0% | |
| 94.0-95.0% | |
| < 94% | |

FIG. 3E

|  | SAMPLE DESCRIPTION | SAMPLE REFERANCE | MAIN PEAK RT | MAIN PEAK AREA | MAIN PEAK % | HMW1 % | HMW2 % | LMW |
|---|---|---|---|---|---|---|---|---|
| 280 nm* | 50MG/ML NO DET NO AGITATION | A-01 | 3.496 | 12703420 | 98.27 | 0.06 | 1.65 | 0.02 |
|  | 50MG/ML PS20 NO AGITATION | B-01 | 3.488 | 9272152 | 98.35 | 0.05 | 1.58 | 0.02 |
|  | 50MG/ML PS80 NO AGITATION | C-01 | 3.498 | 15193303 | 98.25 | 0.05 | 1.69 | 0.01 |
|  | 50MG/ML POLOX NO AGITATION | D-01 | 3.494 | 15837329 | 98.20 | 0.06 | 1.72 | 0.01 |
|  | 50MG/ML NO DET AGITATION | A-02 | 3.491 | 12973236 | 91.08 | 4.32 | 4.54 | 0.07 |
|  | 50MG/ML PS20 AGITATION | B-02 | 3.495 | 14438378 | 98.25 | 0.06 | 1.67 | 0.02 |
|  | 50MG/ML PS80 AGITATION | C-02 | 3.491 | 12802958 | 98.26 | 0.06 | 1.66 | 0.02 |
|  | 50MG/ML POLOX AGITATION | D-02 | 3.492 | 15156953 | 98.15 | 0.11 | 1.72 | 0.01 |

|  | SAMPLE DESCRIPTION | SAMPLE REFERANCE | MAIN PEAK RT | MAIN PEAK AREA | MAIN PEAK % | HMW1 % | HMW2 % | LMW |
|---|---|---|---|---|---|---|---|---|
| 214 nm* | 5MG/ML NO DET NO AGITATION | A2-01 | 3.496 | 25617278 | 97.93 | 0.10 | 1.94 | 0.03 |
|  | 5MG/ML PS20 NO AGITATION | B2-01 | 3.494 | 16714215 | 98.36 | 0.07 | 1.54 | 0.03 |
|  | 5MG/ML PS80 NO AGITATION | C2-01 | 3.493 | 14643654 | 98.36 | 0.07 | 1.54 | 0.03 |
|  | 5MG/ML POLOX NO AGITATION | D2-01 | 3.490 | 21103145 | 98.21 | 0.08 | 1.69 | 0.02 |
|  | 5MG/ML NO DET AGITATION | A2-02 | 3.495 | 1131624 | 40.61 | 41.20 | 15.25 | 2.94 |
|  | 5MG/ML PS20 AGITATION | B2-02 | 3.494 | 16671290 | 98.32 | 0.08 | 1.56 | 0.03 |
|  | 5MG/ML PS80 AGITATION | C2-02 | 3.489 | 15265066 | 98.35 | 0.06 | 1.56 | 0.03 |
|  | 5MG/ML POLOX AGITATION | D2-02 | 3.494 | 19822197 | 98.25 | 0.10 | 1.62 | 0.02 |

* 50 MG/ML SAMPLES: 280 NM DATA USED AS 214 NM DATA SATURATED DETECTOR

FIG. 7

SAMPLE SET 1

| TREATMENT | SAMPLE CONCENTRATION | SAMPLE | HMW1 | HMW2 | TOTAL HMW | IgG MAIN PEAK | LMW | TOTAL PEAK AREA |
|---|---|---|---|---|---|---|---|---|
| | | REFERENCE STANDARD | 0.08 | 1.59 | 1.67 | 98.30 | 0.03 | 14119038 |
| | | | 0.09 | 1.62 | 1.61 | 98.26 | 0.03 | 14126552 |
| | | REFERENCE STANDARD START | 0.07 | 1.60 | 1.67 | 98.30 | 0.03 | 14093637 |
| | | | 0.07 | 1.59 | 1.66 | 98.30 | 0.03 | 14101032 |
| TREATMENT | SAMPLE CONCENTRATION | | 0.07 | 1.57 | 1.64 | 98.32 | 0.03 | 14098369 |
| PRE-AGITATION | 5 MG/ML | NO DETERGENT | 0.06 | 1.53 | 1.59 | 98.38 | 0.03 | 13942168 |
| | | 0.1% TWEEN 20 | 0.07 | 1.61 | 1.68 | 98.29 | 0.03 | 14319775 |
| | | 0.1% TWEEN 80 | 0.07 | 1.62 | 1.69 | 98.28 | 0.03 | 14335625 |
| | | 0.03% TWEEN 20 | 0.08 | 1.63 | 1.71 | 98.27 | 0.03 | 14387214 |
| | | 0.03% TWEEN 80 | 0.07 | 1.63 | 1.70 | 98.26 | 0.03 | 14394490 |
| | 50 MG/ML | NO DETERGENT | 0.07 | 1.58 | 1.65 | 98.33 | 0.03 | 14304806 |
| | | 0.1% TWEEN 20 | 0.06 | 1.63 | 1.69 | 98.27 | 0.03 | 14647786 |
| | | 0.1% TWEEN 80 | 0.07 | 1.64 | 1.71 | 98.26 | 0.03 | 14611923 |
| | | 0.03% TWEEN 20 | 0.07 | 1.63 | 1.70 | 98.27 | 0.03 | 14494508 |
| | | 0.03% TWEEN 80 | 0.07 | 1.64 | 1.71 | 98.25 | 0.03 | 14404627 |
| TREATMENT | SAMPLE CONCENTRATION | CHECK STANDARD | 0.08 | 1.56 | 1.64 | 98.33 | 0.03 | 14115736 |
| 4 HOURS, 400RPM, 7C | 5 MG/ML | NO DETERGENT | 0.07 | 1.57 | 1.64 | 98.33 | 0.03 | 14158097 |
| | | 0.1% TWEEN 20 | 0.08 | 1.63 | 1.71 | 98.26 | 0.03 | 14285857 |
| | | 0.1% TWEEN 80 | 0.08 | 1.63 | 1.71 | 98.25 | 0.04 | 14386120 |
| | | 0.03% TWEEN 20 | 0.08 | 1.64 | 1.72 | 98.25 | 0.03 | 14590191 |
| | | 0.03% TWEEN 80 | 0.07 | 1.66 | 1.73 | 98.23 | 0.03 | 14554723 |
| | 50 MG/ML | NO DETERGENT | 0.07 | 1.59 | 1.66 | 98.31 | 0.03 | 14459012 |
| | | 0.1% TWEEN 20 | 0.07 | 1.65 | 1.72 | 98.24 | 0.03 | 15993395 |
| | | 0.1% TWEEN 80 | 0.08 | 1.66 | 1.74 | 98.23 | 0.03 | 16399973 |
| | | 0.03% TWEEN 20 | 0.07 | 1.66 | 1.73 | 98.23 | 0.03 | 16610604 |
| | | 0.03% TWEEN 80 | 0.07 | 1.64 | 1.71 | 98.25 | 0.03 | 15515599 |
| | | REFERENCE STANDARD END | 0.08 | 1.55 | 1.63 | 98.34 | 0.03 | 14126133 |
| | | | 0.08 | 1.56 | 1.64 | 98.32 | 0.03 | 14115326 |
| | | | 0.09 | 1.56 | 1.65 | 98.32 | 0.03 | 14122380 |

FIG. 8A

SAMPLE SET 2

| TREATMENT | SAMPLE CONCENTRATION | SAMPLE | HMW1 | HMW2 | TOTAL HMW | IgG MAIN PEAK | LMW | TOTAL PEAK AREA |
|---|---|---|---|---|---|---|---|---|
| | | REFERENCE STANDARD START | 0.07 | 1.56 | 1.63 | 98.34 | 0.03 | 14143250 |
| | | | 0.08 | 1.55 | 1.63 | 98.34 | 0.03 | 14146577 |
| | | | 0.09 | 1.55 | 1.64 | 98.33 | 0.03 | 14153899 |
| +4 HOURS, 1000RPM, 7C | 5 MG/ML | NO DETERGENT | 0.11 | 1.43 | 1.54 | 98.43 | 0.03 | 13955881 |
| | | 0.1% TWEEN 20 | 0.08 | 1.64 | 1.72 | 98.25 | 0.03 | 14676944 |
| | | 0.1% TWEEN 80 | 0.07 | 1.66 | 1.73 | 98.24 | 0.03 | 14932977 |
| | | 0.03% TWEEN 20 | 0.07 | 1.65 | 1.72 | 98.25 | 0.03 | 14902081 |
| | | 0.03% TWEEN 80 | 0.07 | 1.63 | 1.70 | 98.27 | 0.03 | 14522490 |
| | 50 MG/ML | NO DETERGENT | 0.08 | 1.65 | 1.73 | 98.24 | 0.03 | 13857467 |
| | | 0.1% TWEEN 20 | 0.07 | 1.71 | 1.78 | 98.19 | 0.03 | 15261335 |
| | | 0.1% TWEEN 80 | 0.07 | 1.69 | 1.76 | 98.20 | 0.03 | 14957013 |
| | | 0.03% TWEEN 20 | 0.08 | 1.67 | 1.75 | 98.22 | 0.03 | 14911663 |
| | | 0.03% TWEEN 80 | 0.07 | 1.68 | 1.75 | 98.22 | 0.03 | 14022612 |
| TREATMENT | SAMPLE CONCENTRATION | CHECK STANDARD | 0.08 | 1.55 | 1.63 | 98.34 | 0.03 | 14138092 |
| | | | 0.07 | 1.55 | 1.62 | 98.34 | 0.03 | 14127095 |
| | | | 0.07 | 1.55 | 1.62 | 98.34 | 0.03 | 14167687 |
| +3 HOURS, 1200RPM, 29C | 5 MG/ML | NO DETERGENT | 0.11 | 1.50 | 1.61 | 98.32 | 0.06 | 13860398 |
| | | 0.1% TWEEN 20 | 0.08 | 1.62 | 1.70 | 98.27 | 0.03 | 14254367 |
| | | 0.1% TWEEN 80 | 0.08 | 1.62 | 1.70 | 98.27 | 0.03 | 13983444 |
| | | 0.03% TWEEN 20 | 0.07 | 1.63 | 1.70 | 98.26 | 0.03 | 14030597 |
| | | 0.03% TWEEN 80 | 0.08 | 1.62 | 1.70 | 98.27 | 0.03 | 14564434 |
| | 50 MG/ML | NO DETERGENT | 0.09 | 1.66 | 1.75 | 98.21 | 0.04 | 14133039 |
| | | 0.1% TWEEN 20 | 0.08 | 1.70 | 1.78 | 98.18 | 0.04 | 15171565 |
| | | 0.1% TWEEN 80 | 0.08 | 1.70 | 1.78 | 98.19 | 0.04 | 15186380 |
| | | 0.03% TWEEN 20 | 0.08 | 1.71 | 1.79 | 98.17 | 0.04 | 16068396 |
| | | 0.03% TWEEN 80 | 0.08 | 1.68 | 1.76 | 98.20 | 0.03 | 14899569 |
| | | REFERENCE STANDARD END | | | | | | 122248 |
| | | | 0.08 | 1.54 | 1.62 | 98.35 | 0.03 | 14218052 |
| | | | 0.08 | 1.55 | 1.63 | 98.33 | 0.03 | 14217590 |

FIG. 8B

SAMPLE SET 3

| TREATMENT | SAMPLE CONCENTRATION | SAMPLE | HMW1 | HMW2 | TOTAL HMW | IgG MAIN PEAK | LMW | TOTAL PEAK AREA |
|---|---|---|---|---|---|---|---|---|
| | | REFERENCE STANDARD START | | | | | | 50337 |
| | | | 0.06 | 1.52 | 1.58 | 98.38 | 0.03 | 14346262 |
| | | | 0.07 | 1.54 | 1.61 | 98.36 | 0.03 | 14344745 |
| +O/N, 1200RPM, 29C | 5 MG/ML | NO DETERGENT | 0.09 | 1.47 | 1.56 | 98.27 | 0.17 | 13850409 |
| | | 0.1% TWEEN 20 | 0.07 | 1.58 | 1.65 | 98.32 | 0.03 | 14805142 |
| | | 0.1% TWEEN 80 | 0.07 | 1.58 | 1.65 | 98.31 | 0.03 | 14771162 |
| | | 0.03% TWEEN 20 | 0.07 | 1.59 | 1.66 | 98.31 | 0.03 | 15044679 |
| | | 0.03% TWEEN 80 | 0.07 | 1.58 | 1.65 | 98.32 | 0.03 | 14915839 |
| | 50 MG/ML | NO DETERGENT | 0.09 | 1.70 | 1.79 | 98.16 | 0.05 | 14737823 |
| | | 0.1% TWEEN 20 | 0.08 | 1.75 | 1.83 | 98.14 | 0.04 | 16533374 |
| | | 0.1% TWEEN 80 | 0.08 | 1.77 | 1.85 | 98.11 | 0.04 | 15635031 |
| | | 0.03% TWEEN 20 | 0.08 | 1.74 | 1.82 | 98.14 | 0.04 | 16147070 |
| | | 0.03% TWEEN 80 | 0.08 | 1.75 | 1.83 | 98.13 | 0.04 | 15541837 |
| | | REFERENCE STANDARD END | | | | | | |

FIG. 8C

IL-6 ANTAGONIST FORMULATIONS AND USES THEREOF

RELATED APPLICATION

This application is a continuation of U.S. application Ser. No. 16/078,671, filed Aug. 22, 2018, now abandoned, which is a U.S. national-phase application of International Application Serial No. PCT/US2017/019131, filed Feb. 22, 2017, which claims the benefit of U.S. Provisional Patent Application Ser. No. 62/298,774, filed Feb. 23, 2016, which is incorporated by reference herein.

FIELD OF THE INVENTION

The present invention relates to therapeutic compositions formulations, e.g., for interleukin-6 (IL-6) antagonists.

BACKGROUND

IL-6 is a pleiotropic cytokine with reported roles in inflammation, hematopoiesis, angiogenesis, cell differentiation, and neuronal survival.

SUMMARY

Featured herein are formulations (e.g., pharmaceutical compositions, e.g., stable aqueous formulations) containing IL-6 antagonists (e.g., IL-6 antibody molecules, e.g., IL-6 antibodies or fragments thereof, as described in WO2014/074905) that can be used, inter alia, to modulate IL-6 family cytokines and protein complexes thereof, and/or their respective receptors (e.g., IL-6 receptors), to treat disorders, and to detect and/or bind to IL-6. Described herein is a pharmaceutical formulation that includes 1 mg/ml to 100 mg/ml of an IL-6 antagonist, e.g., an anti-IL-6 antibody or fragment thereof. In embodiments, the pharmaceutical formulation comprises 5 mg/ml to 50 mg/ml of an IL-6 antagonist, e.g., an IL-6 antibody or fragment thereof; and one or more, or all, of, a buffer (e.g., a buffering agent), a surfactant, and/or a tonicity agent. In one embodiment, the pharmaceutical formulation comprises 5 mg/ml to 50 mg/ml of an IL-6 antibody or fragment thereof, a buffering agent, a surfactant, and two tonicity agents (e.g., a sugar and a salt).

Formulations

In one aspect, the present disclosure features a formulation, e.g., a pharmaceutical formulation, comprising 1-100 mg/mL of an IL-6 antagonist. In one embodiment, the formulation comprises 5-50 mg/mL of an IL-6 antagonist. In one embodiment, the formulation comprises about 5 mg/mL of an IL-6 antagonist. In one embodiment, the formulation comprises about 50 mg/mL of an IL-6 antagonist thereof. In any of the formulations described herein, the IL-6 antagonist is an IL-6 antibody molecule, e.g., an IL-6 antibody or fragment thereof.

In one aspect, the present disclosure features a formulation, e.g., a pharmaceutical formulation, comprising 1-100 mg/mL of an IL-6 antibody or fragment thereof. In one embodiment, the formulation comprises 5-50 mg/mL of an IL-6 antibody or fragment thereof. In one embodiment, the formulation comprises 1-10 mg/mL of an IL-6 antibody or fragment thereof. In one embodiment, the formulation comprises 2-3 mg/mL of an IL-6 antibody or fragment thereof. In one embodiment, the formulation comprises 3-4 mg/mL of an IL-6 antibody or fragment thereof. In one embodiment, the formulation comprises 4-5 mg/mL of an IL-6 antibody or fragment thereof. In one embodiment, the formulation comprises 5-6 mg/mL of an IL-6 antibody or fragment thereof. In one embodiment, the formulation comprises 6-7 mg/mL of an IL-6 antibody or fragment thereof. In one embodiment, the formulation comprises 7-8 mg/mL of an IL-6 antibody or fragment thereof. In one embodiment, the formulation comprises 8-9 mg/mL of an IL-6 antibody or fragment thereof. In one embodiment, the formulation comprises 9-10 mg/mL of an IL-6 antibody or fragment thereof. In one embodiment, the formulation comprises 5 mg/mL, +/−10% of an IL-6 antibody or fragment thereof. In one embodiment, the formulation comprises 5 mg/mL, +/−20% of an IL-6 antibody or fragment thereof. In one embodiment, the formulation comprises 5 mg/mL, +/−30% of an IL-6 antibody or fragment thereof. In one embodiment, the formulation comprises 5 mg/mL of an IL-6 antibody or fragment thereof. In one embodiment, the formulation comprises 10-100 mg/mL of an IL-6 antibody or fragment thereof. In one embodiment, the formulation comprises 20-80 mg/mL of an IL-6 antibody or fragment thereof. In one embodiment, the formulation comprises 40-60 mg/mL of an IL-6 antibody or fragment thereof. In one embodiment, the formulation comprises 20-30 mg/mL of an IL-6 antibody or fragment thereof. In one embodiment, the formulation comprises 30-40 mg/mL of an IL-6 antibody or fragment thereof. In one embodiment, the formulation comprises 40-50 mg/mL of an IL-6 antibody or fragment thereof. In one embodiment, the formulation comprises 50-60 mg/mL of an IL-6 antibody or fragment thereof. In one embodiment, the formulation comprises 60-70 mg/mL of an IL-6 antibody or fragment thereof. In one embodiment, the formulation comprises 70-80 mg/mL of an IL-6 antibody or fragment thereof. In one embodiment, the formulation comprises 80-90 mg/mL of an IL-6 antibody or fragment thereof. In one embodiment, the formulation comprises 90-100 mg/mL of an IL-6 antibody or fragment thereof. In one embodiment, the formulation comprises 50 mg/mL of an IL-6 antibody or fragment thereof. Exemplary IL-6 antibody molecules, e.g., IL-6 antibodies and fragments thereof, are provided herein. In one embodiment, the formulation comprises a concentration of an IL-6 antibody molecule, e.g., IL-6 antibody or fragment thereof, which is between at least 10% less than and at least 10% greater than a concentration of IL-6 antibody molecule disclosed herein. By way of example, in one embodiment the formulation comprises 50 mg/mL+/−10% of an IL-6 molecule, e.g., an IL-6 antibody or fragment thereof. In one embodiment, the formulation comprises 50 mg/mL, +/−20% of an IL-6 antibody or fragment thereof. In one embodiment, the formulation comprises 50 mg/mL, +/−30% of an IL-6 antibody or fragment thereof.

In one embodiment, the formulation further comprises 1-50 mM histidine buffer, e.g., 5-40 mM histidine buffer, 10-30 mM histidine buffer, or 15-25 mM histidine buffer. In one embodiment, the formulation further comprises 1-10 mM histidine buffer, 10-20 mM histidine buffer, 20-30 mM histidine buffer, 30-40 mM histidine buffer, 40-50 mM histidine buffer, 5-10 mM histidine buffer, 10-15 mM histidine buffer, 15-20 mM histidine buffer, 20-25 mM histidine buffer, 25-30 mM histidine buffer, 30-35 mM histidine buffer, 35-40 mM histidine buffer, 40-45 mM histidine buffer, or 45-50 mM histidine buffer. In one embodiment, the formulation further comprises 1 mM, 5 mM, 10 mM, 15 mM, 20 mM, 25 mM, 30 mM, 35 mM, 40 mM, 45 mM, or 50 mM histidine buffer. In one embodiment, the formulation comprises concentration of a buffer, e.g., a histidine buffer, which is between at least 10% less than and at least 10% greater than a concentration of a buffer disclosed herein. By way of example, in one embodiment the formulation comprises 20 mM+/−10% of histidine buffer. In one embodiment, the formulation further comprises 20 mM+/−20% histidine buffer. In one embodiment, the formulation further comprises 20 mM+/−30% histidine buffer.

In one embodiment, the formulation further comprises 0.01% to 1% w/v polysorbate-20 (Tween-20), polysorbate-80 (Tween-80), or poloxamer 188, e.g., 0.01% to 0.5%, 0.01% to 0.1%, 0.01% to 0.05%, 0.02% to 0.04% w/v polysorbate-20 (Tween-20), polysorbate-80 (Tween-80), or poloxamer 188. In one embodiment, the formulation further comprises 0.01 to 0.02%, 0.02% to 0.03%, 0.03 to 0.04%, 0.04% to 0.05%, 0.05% to 0.06%, 0.07% to 0.08%, 0.08% to 0.09%, or 0.09% to 0.1% w/v polysorbate-20 (Tween-20), polysorbate-80 (Tween-80), or poloxamer 188. In one embodiment, the formulation further comprises 0.01%, 0.02%, 0.03%, 0.04%, 0.05%, 0.1%, 0.15%, 0.2%, 0.5%, or 1% w/v polysorbate-20 (Tween-20), polysorbate-80 (Tween-80), or poloxamer 188. In one embodiment, the formulation comprises concentration of a surfactant, e.g., polysorbate-20 (Tween-20), polysorbate-80 (Tween-80), or poloxamer 188, which is between at least 10% less than and at least 10% greater than a concentration of a surfactant disclosed herein. By way of example, in one embodiment the formulation comprises 0.03%+/−0.003% of polysorbate-20 (Tween-20), polysorbate-80 (Tween-80), or poloxamer 188. In one embodiment, the formulation further comprises 0.03%+/−0.006% of polysorbate-20 (Tween-20), polysorbate-80 (Tween-80), or poloxamer 188. In one embodiment, the formulation further comprises 0.03%+/−0.01% of polysorbate-20 (Tween-20), polysorbate-80 (Tween-80), or poloxamer 188. In any of the formulations described herein, polysorbate-20 (Tween-20), polysorbate-80 (Tween-80), and poloxamer 188 are interchangeable.

In one embodiment, the formulation further comprises 1-150 mM sodium chloride, e.g., 1-50 mM, 1-25 mM, 5-100 mM, 10-75 mM, 10-50 mM, 10-30 mM, or 15-25 mM sodium chloride. In one embodiment, the formulation further comprises 1-10 mM, 1-20 mM, 5-15 mM, 5-25 mM, 10-20 mM, 10-30 mM, 15-25 mM, 15-35 mM, 20-30 mM, 30-40 mM, 40-50 mM, 50-60 mM, 70-80 mM, 80-90 mM, 90-100 mM, 100-110 mM, 110-120 mM, 120-130 mM, 130-140 mM, or 140-150 mM sodium chloride. In one embodiment, the formulation further comprises about 1 mM, 5 mM, 10 mM, 15 mM, 20 mM, 25 mM, 30 mM, 50 mM, 100 mM, or 150 mM sodium chloride. In one embodiment, the formulation comprises concentration of sodium chloride, which is between at least 10% less than and at least 10% greater than a concentration of sodium chloride disclosed herein. By way of example, in one embodiment the formulation comprises 20 mM+/−10% of sodium chloride. In one embodiment, the formulation further comprises 20 mM+/−20% sodium chloride. In one embodiment, the formulation further comprises 20 mM+/−30% sodium chloride.

In one embodiment, the formulation further comprises 1 to 10% sorbitol, e.g., 1 to 8%, 1 to 6%, 2 to 5%, or 3 to 5% sorbitol. In one embodiment, the formulation further comprises 1 to 10% sorbitol, 2% to 12%, 3% to 13%, 4% to 14%, 5% to 15%, 1% to 2%, 2%, to 3%, 3% to 4%, 4% to 5%, 5% to 6%, 6%, to 7%, 7% to 8%, 8% to 9%, or 9% to 10% sorbitol. In one embodiment, the formulation further comprises about 1%, 2%, 3%, 4%, 5%, 6%, 7%, 8%, 9%, or 10% sorbitol. In one embodiment, the formulation comprises concentration of sorbitol, which is between at least 10% less than and at least 10% greater than a concentration of sorbitol disclosed herein. By way of example, in one embodiment the formulation comprises 4%+/−0.4% sorbitol. In one embodiment, the formulation further comprises 4%+/−0.8% sorbitol. In one embodiment, the formulation further comprises 4%+/−1.2% sorbitol.

In embodiments, the pH of the formulation is between about 5.5 and about 7.5, e.g., between about 5.5 and about 7.0, between about 6.0 and about 7.0, between about 6.2 and about 6.8. In one embodiment, the pH of the formulation is about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, or about 7.0. In one embodiment, the pH of the formulation is about 6.5.

In one aspect, the present disclosure features a formulation, e.g., a pharmaceutical formulation, comprising 1-100 mg/ml or 5-50 mg/ml of an IL-6 antibody or fragment thereof as described herein, 10-50 mM histidine buffer; 0.01%-0.1% polysorbate-20 (Tween-20), polysorbate-80 (Tween-80), or poloxamer 188; 1-150 mM sodium chloride; and 1-10% sorbitol; at a pH between 5.5 and 7.5, e.g., at a pH of 6.5. In another aspect, the present disclosure features a formulation, e.g., a pharmaceutical formulation, comprising 5-50 mg/ml of an IL-6 antibody or fragment thereof as described herein; 10-30 mM histidine buffer; 0.01%-0.05% polysorbate-20 (Tween-20), polysorbate-80 (Tween-80), or poloxamer 188; 10-30 mM sodium chloride; and 1-6% sorbitol; at pH between 6 and 7, e.g., at pH of 6.5. In yet another aspect, the present disclosure features a formulation, e.g., a pharmaceutical formulation, comprising 5-50 mg/ml of an IL-6 antibody or fragment thereof as described herein; 15-25 mM histidine buffer; 0.02%-0.04% polysorbate-20 (Tween-20), polysorbate-80 (Tween-80), or poloxamer 188; 15-25 mM sodium chloride; and 3-5% sorbitol; at pH between 6.2 and 6.8, e.g., at pH of 6.5.

In another aspect, the present disclosure features a formulation, e.g., a pharmaceutical formulation, comprising about 5-50 mg/mL of an anti-IL-6 antibody or fragment thereof as described herein; 20 mM histidine buffer, e.g., histidine HCl; 0.03% polysorbate-20 (Tween-20); 20 mM sodium chloride; and 4% sorbitol; at pH of 5.5. In one embodiment, the formulation comprises about 5 mg/mL of an anti-IL-6 antibody or fragment thereof; 20 mM histidine buffer, e.g., histidine HCl; 0.03% polysorbate-20 (Tween-20), polysorbate-80 (Tween-80), or poloxamer 188; 20 mM sodium chloride; and 4% sorbitol, at a pH of 5.5. In one embodiment, the formulation comprises about 50 mg/mL of an anti-IL-6 antibody or fragment thereof; 20 mM histidine buffer, e.g., histidine HCl; 0.03% polysorbate-20 (Tween-20), polysorbate-80 (Tween-80), or poloxamer 188; 20 mM sodium chloride; and 4% sorbitol, at pH of 5.5.

In another aspect, the present disclosure features a formulation, e.g., a pharmaceutical formulation, comprising about 5-50 mg/mL of an anti-IL-6 antibody or fragment thereof as described herein; 20 mM histidine buffer, e.g., histidine HCl; 0.03% polysorbate-20 (Tween-20), polysorbate-80 (Tween-80), or poloxamer 188; 20 mM sodium chloride; and 4% sorbitol; at pH of 5.5. In one embodiment, the formulation comprises about 5 mg/mL of an anti-IL-6 antibody or fragment thereof; 20 mM histidine buffer, e.g., histidine HCl; 0.03% polysorbate-20 (Tween-20), polysorbate-80 (Tween-80), or poloxamer 188; 20 mM sodium chloride; and 4% sorbitol, at a pH of 5.5. In one embodiment, the formulation comprises about 50 mg/mL of an anti-IL-6 antibody or fragment thereof; 20 mM histidine buffer, e.g., histidine HCl; 0.03% polysorbate-20 (Tween-20), polysorbate-80 (Tween-80), or poloxamer 188; 20 mM sodium chloride; and 4% sorbitol, at pH of 5.5.

In any of the formulations described herein, the formulation may further comprise one or more, or all, of a chelating agent, a preserving agent, a viscosity agent, a penetration enhancer or bioadhesive, a stabilizer, and/or an antioxidant.

In any of the formulations described herein, the formulation further comprises a second therapeutic agent. In one embodiment, the second therapeutic agent is an anti-VEGF agent, an anti-PGDF agent, or a steroid, e.g., a corticosteroid. As used herein an the anti-VEGF agent or the anti-PDGF agent can be a small molecule, a peptide, an antibody, or a nucleic acid that inhibits or decreases the activity of the VEGF pathway. In one embodiment, the anti-VEGF agent is an antibody that inhibits or decreases the activity of a component of the VEGF pathway, e.g., VEGF or a the VEGF receptor. In one embodiment, the anti-PDGF agent is an antibody that inhibits or decreases the activity of a component of the PDGF pathway, e.g., PDGF or the PDGF receptor.

In any of the formulations described herein, the formulation is stable at room temperature or less, e.g., at a temperature of about 20° C. or less. In one embodiment, the formulation is stable at 20° C. or less, 10° C. or less, 8° C. or less, 4° C. or less, 2° C. or less, −20° C. or less, −65° C. or less, −80° C. or less, −100° C. or less. In one embodiment, the formulation is stable between 2 and 20° C., e.g., 2-8° C. In one embodiment, the formulation is stable for at least 1 week, at least 2 weeks, at least 1 month, at least 2 months, at least 4 months, at least 6 months, at least 12 months, at least 16 months, at least 20 months, at least 24 months, or at least 36 months. In one embodiment, the formulation is stable at a temperature of −65° C. or less for at least 1 or 2 years. In one embodiment, the formulation is stable at a temperature between 2 to 8° C. for at least 6 months.

IL-6 Antibodies

In any of the formulations described herein, the IL-6 antibody molecule, e.g., antibody or fragment thereof, comprises a sequence, or portions thereof, provided in Table 1 or FIG. 1A or 1B. In one embodiment, the IL-6 antibody molecule, e.g., antibody or fragment thereof, comprises a VH CDR1 comprising the sequence of SEQ ID NO:19, a VH CDR2 comprising the sequence of SEQ ID NO:20, and a VH CDR3 comprising the sequence of SEQ ID NO:21. In one embodiment, the IL-6 antibody or fragment thereof further comprises a VL CDR1 comprising the sequence of SEQ ID NO:22, a VL CDR2 comprising the sequence of SEQ ID NO:23, and a VL CDR3 comprising the sequence of SEQ ID NO:24. In another embodiment, the IL-6 antibody or fragment thereof comprises a VH CDR1 comprising the sequence of SEQ ID NO:19, a VH CDR2 comprising the sequence of SEQ ID NO:20, and a VH CDR3 comprising the sequence of SEQ ID NO:21; and a VL CDR1 comprising the sequence of SEQ ID NO:22, a VL CDR2 comprising the sequence of SEQ ID NO:23, and a VL CDR3 comprising the sequence of SEQ ID NO:24.

In one embodiment, the IL-6 antibody or fragment thereof comprises (e.g., consists of) a constant region sequence that is at least 90%, 91%, 92%, 93%, 94%, 95%, 96%, 97%, 98%, or 99% identical to SEQ ID NO: 28 or SEQ ID NO: 29. In one embodiment, the IL-6 antibody or fragment thereof comprises (e.g., consists of) a constant region sequence comprising SEQ ID NO: 28 or SEQ ID NO: 29.

In one embodiment, the IL-6 antibody or fragment thereof comprises (e.g., consists of) a heavy chain variable region sequence that is at least 90%, 91%, 92%, 93%, 94%, 95%, 96%, 97%, 98%, or 99% identical to SEQ ID NO:17. In one embodiment, the IL-6 antibody or fragment thereof comprises (e.g., consists of) a heavy chain variable region sequence comprising SEQ ID NO:17.

In one embodiment, the IL-6 antibody or fragment thereof comprises (e.g., consists of) a heavy chain sequence that is at least 90%, 91%, 92%, 93%, 94%, 95%, 96%, 97%, 98%, or 99% identical to SEQ ID NO:13. In one embodiment, the IL-6 antibody or fragment thereof comprises (e.g., consists of) a heavy chain sequence comprising SEQ ID NO:13.

In one embodiment, the IL-6 antibody or fragment thereof comprises (e.g., consists of) a light chain variable region sequence that is at least 90%, 91%, 92%, 93%, 94%, 95%, 96%, 97%, 98%, or 99% identical to SEQ ID NO:18. In one embodiment, the IL-6 antibody or fragment thereof comprises (e.g., consists of) a light chain variable region sequence comprising SEQ ID NO:18, or In one embodiment, the IL-6 antibody or fragment thereof comprises (e.g., consists of) a light chain sequence that is at least 90%, 91%, 92%, 93%, 94%, 95%, 96%, 97%, 98%, or 99% identical to SEQ ID NO:14. In one embodiment, the IL-6 antibody or fragment thereof comprises (e.g., consists of) a light chain sequence comprising SEQ ID NO:14.

In one embodiment, the IL-6 antibody or fragment thereof comprises (e.g., consists of) a heavy chain variable region comprising SEQ ID NO:17 and a light chain variable region comprising SEQ ID NO:18. In one embodiment, the IL-6 antibody or fragment thereof comprises (e.g., consists of) comprises a heavy chain sequence comprising SEQ ID NO:13 and a light chain sequence comprising SEQ ID NO:14.

In one embodiment, the anti-IL-6 antibody is an IgG2 antibody. In one embodiment, the IL-6 antibody is a full-length antibody. As described further herein, IgG2 antibodies can exist in different structural isoforms due to alternative disulfide bonding between the heavy and light chains of the antibody, e.g., isoform IgG2-A, isoform IgG2-A/B, and isoform IgG2-B, also referred to herein as isoform A, isoform A/B, or isoform B. The structures of the isoforms are also shown in FIG. 11.

In one embodiment, at least 85%, 86%, 87%, 88%, 89%, 90%, 91%, 92%, 93%, 94%, 95%, 96%, 97%, 98%, or 99%, of the antibody present in the formulation is in isoform A or A/B, collectively. In one embodiment, at least 70%, 75%, 80%, 81%, 82%, 83%, 84%, 85%, 86%, 87%, 88%, 89%, or 90%, of the antibody present in the formulation is in isoform A. In one embodiment, less than 5%, 4%, 3%, 2%, 1%, 0.9%, 0.8%, 0.7%, 0.6%, 0.5%, 0.4%, 0.3%, 0.2%, or 0.1%, of the antibody present in the formulation is in isoform B. In one embodiment, the formulation is substantially free of the antibody present in isoform B, e.g., less than 5%, less than 4%, less than 3%, less than 2%, less than 1%, or less than 0.5% of the antibody present is in isoform B. The percentage, amount, or quantity of antibody present in the formulation in isoform A, A/B, and/or B can be determined by HPLC, e.g., reverse phase HPLC (RP-HPLC), or peptide mapping under non-reducing conditions, followed by mass spectrometry (MS) analysis.

Therapeutic Application

Also provided herein are compositions and methods for treating a subject having an IL-6-associated disease or disorder. The method includes administering to the subject a therapeutically effective amount of a composition comprising a formulation described herein. In embodiments, the method includes identifying a subject having an IL-6 associated disease or disorder described herein; and administering to the subject a therapeutically effective amount of a composition comprising a formulation as described herein.

Also described herein is a method of inhibiting IL-6 activity in a subject. The method includes administering to the subject a formulation as described herein. In embodiments, the subject has an IL-6-associated disease or disorder described herein.

Also disclosed herein is the use of a composition as described herein in the manufacture of a medicament for treating or preventing an IL-6 associated disease or disorder in a subject, e.g., in the manufacture of a medicament for suitable for administration to a subject for treating or preventing an IL-6 associated disease or disorder in the subject. In embodiments, the medicament is for administration to the eye, e.g., ocular administration.

IL-6 associated diseases or disorders, e.g., for treating by administering the compositions or formulations described herein, can be associated with increased or elevated IL-6 expression or activity. In an embodiment, one or more symptoms of the IL-6 associated disease or disorder is associated with increased or elevated IL-6 expression or activity. Increased or elevated IL-6 expression can be determined in a subject as compared to the level of IL-6 expression prior to onset of the disease or a symptom of the disease. Increased or elevated IL-6 expression can be determined in a subject as compared to another subject that does not have an IL-6 associated disease or disorder. Examples of IL-6 associated diseases include, but are not limited to, diabetic macular edema (DME), diabetic retinopathy, dry eye (e.g., dry eye disease or dry eye syndrome), allergic conjunctivitis, uveitis, age-related macular degeneration (AMD) (e.g., wet (exudative) or dry (atrophic) AMD), proliferative diabetic retinopathy (PDR), Rhegmatogenous retinal detachment (RRD), retinal vein occlusion (RVO), neuromyelitis optica (NMO), corneal transplant, corneal abrasion, myopic choroidal neovascularization, ocular cancers (e.g., cancers affecting the eye or area around the eye, e.g., the eye socket and/or eyelids), or physical injury to the eye.

In some embodiments, a second therapeutic agent is administered to the subject in combination with a formulation as described herein. In an embodiment, the second therapeutic agent is administered in a separate composition than the formulation described herein. In an embodiment, the formulation described herein includes the second therapeutic agent. Suitable second therapeutic agents include any therapeutic agent commercially available or known for treating an IL-6 associated disease or disorder described herein. In one embodiment, the second therapeutic agent is an anti-VEGF agent, an anti-PDGF agent, or a steroid.

In general, the subject treated as described herein is a human or other mammal such as a dog or cat. In some embodiments, the subject has previously been treated with an anti-VEGF agent or a steroid. In some embodiments, the subject is resistant or refractory to anti-VEGF agent or steroid treatment, e.g., the subject did not respond to treatment with an anti-VEGF agent or steroid. In embodiments, subjects that do not respond to a given treatment are those in which one or more symptoms of a disease or disorder, e.g., an IL-6 related disease, is not ameliorated or reduced after administration of the given treatment.

In another aspect, the present disclosure features a device, e.g., a drug delivery device, comprising a formulation as described herein.

In another aspect, the present disclosure features a container or device comprising a formulation as described herein. In one embodiment, the container is a multidose container. In one embodiment, the container holds a volume of 0.1 ml, 0.2 ml, 0.3 ml, 0.4 ml, 0.5 ml, 0.6 ml, 0.7 ml, 0.8 ml, 0.9 ml, or 1.0 ml.

In another aspect, the present disclosure features a kit comprising a formulation as described herein, and optionally, instructions for use. In one embodiment, the kit comprises one or more containers or devices comprising a formulation as described herein, and optionally, instructions for use.

Unless defined otherwise, all technical and scientific terms used herein have the same meaning as commonly understood by one of ordinary skill in the art to which the invention pertains.

The term "a" and "an" refers to one or to more than one (i.e., to at least one) of the grammatical object of the article. By way of example, "an element" means one element or more than one element.

The term "about" when referring to a measurable value such as an amount, a temporal duration, and the like, is meant to encompass variations of ±20% or in some instances ±10%, or in some instances ±5%, or in some instances ±1%, or in some instances ±0.1% from the specified value, as such variations are appropriate to perform the disclosed methods.

All patents, published patent applications, and published references cited herein are incorporated by reference for all purposes.

BRIEF DESCRIPTION OF THE DRAWINGS

FIG. 1A depicts the locations of FR1, CDR1, FR2, CDR2, FR3, CDR3, FR4, CH1, hinge, CH2, and CH3 in the heavy chain sequences of EBI-029 (SEQ ID NO: 1), EBI-030 (SEQ ID NO: 13), and EBI-031 (EBI-031 is also referred to herein as EBI-030-H311A) (SEQ ID NO: 25).

FIGS. 3A, 3B, 3C, 3D, and 3E show the results from the SE-UPLC analysis performed at day 7, and as described in Example 3.

FIG. 7 summarizes the results from the first agitation study described in Example 4, and as determined by SE-UPLC analysis.

FIGS. 8A, 8B, and 8C summarizes the results from the second agitation study described in Example 4, and as determined by SE-UPLC analysis.

DETAILED DESCRIPTION

Figure 1B:
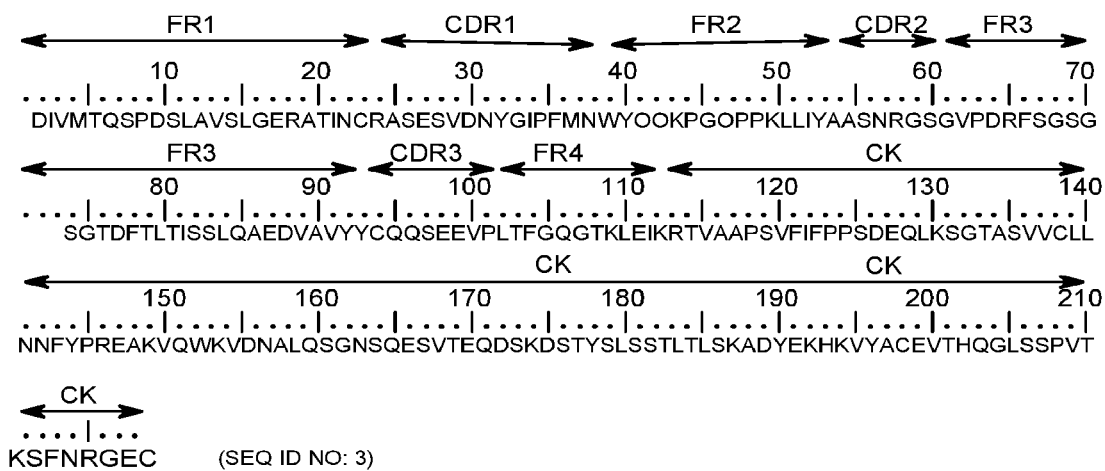
FIG. 1B depicts the locations of FR1, CDR1, FR2, CDR2, FR3, CDR3, FR4, and CK in light chain sequence (EBI-029, EBI-030 and EBI-031 have the same light chain sequence) (SEQ ID NO: 3).

Provided herein are formulations useful for providing an IL-6 antagonist, e.g., an IL-6 antibody or fragment thereof, to a subject in need of treatment with such a formulation. In embodiments, the subject has, or is at risk of having, an IL-6 associated disease or disorder, e.g., a disease associated with elevated or increased IL-6 expression and/or activity. Also disclosed herein are methods of preparing and administering such formulations.

The formulations described herein have been formulated and optimized to be suitable for administration to a patient and to provide improved stability at varying temperatures and prolonged periods of time.

Notably, in the formulations described herein comprising an IL-6 antibody comprising a constant region derived from an IgG2 antibody, e.g., an IgG2 constant region described herein, the formulations comprise an optimal distribution of the different IgG2 structural isoforms, e.g., primarily isoform A and isoform A/B, and very little or negligible amounts of isoform B. The structural isoform B may be associated with aggregation, decreased function, and decreased stability of the antibody. Thus, compositions and formulations comprising the antibody of the invention are less heterogeneous than other compositions or formulations comprising IgG2 antibodies known in the art.

IL-6 Antagonists

The present disclosure provides formulations for delivery of an IL-6 antagonist, also referred to herein as IL-6a. In general, an IL-6 antagonist (IL-6a) described herein can bind to IL-6, and inhibits or reduces at least one IL-6 activity. IL-6 activity can include one or more of the following: binding to gp130; activation of the IL-6 signaling pathway; activation of a JAK kinase, e.g., phosphorylation of a target of a JAK kinase; activation of a STAT protein, e.g., phosphorylation of a STAT protein; and/or expression of a STAT-target gene.

In one embodiment, an IL-6a described herein specifically binds to site II (site 2) of an IL-6 and is useful for treatment of IL-6 related diseases, e.g., IL-6 related eye diseases and certain other diseases as described herein.

In some embodiments, the IL-6a features one or more of the following properties: has high affinity for either free IL-6 (e.g., soluble IL-6) or bound IL-6 (e.g., IL-6 bound to an IL-6 receptor) or both free and bound IL-6; is relatively stable in an organism; can inhibit binding to gp130 of an IL-6 bound to an IL-6R (termed herein an IL-6/IL-6R complex or IL-6/IL-6R); and/or can have a therapeutic effect.

In one embodiment, the IL-6a is an antibody or is a fragment derived from an antibody. For example, an IL-6a is a high affinity, humanized Fab that can specifically bind to site II of an IL-6 and potently blocks both cis- and trans-IL-6 signaling. In another example, the IL-6a is a full length antibody, e.g., an IgG1 or IgG2 antibody.

In one embodiment, the IL-6a selectively binds to site II of IL-6 and provides broad inhibition of IL-6 signaling because such molecules can inhibit the binding of gp130 to IL-6, regardless of whether the IL-6 is free or bound to membrane IL-6R or sIL-6R. Furthermore, targeting the ligand (IL-6) as opposed to the IL-6 receptor can avoid receptor mediated clearance and toxicity due to ADCC (antibody-dependent cell-mediated cytotoxicity).

Because IL-6 plays both pathologic and protective roles in disease, use of an IL-6 antagonist (IL-6a) to treat a disease associated with increased IL-6 can improve certain aspects of a condition, but may also cause significant adverse effects, e.g., systemic effects. This duality of IL-6 pathways (i.e., the ability to have desirable and/or undesirable effects) can make it undesirable to treat an IL-6 associated disorder with a systemic inhibitor. Accordingly, the compositions and methods provided herein can be useful for treatments that inhibit at least one IL-6 activity, but do not have an undue effect on positive activities of IL-6, in part because the compositions can be formulated for local delivery, e.g., for local delivery to the eye. For example, in certain aspects, the IL-6a is designed to be of a size suitable for delivery to a particular site. In some embodiments, the IL-6a is a full-length antibody. In some embodiments, the IL-6a is derived from an antibody and is in a format that may have longer residency in a particular compartment of the eye, e.g., the vitreous of the eye, and limited systemic leakage. In some embodiments, the IL-6a is a modified antibody (e.g., an antibody with a modified Fc domain) that has longer residency in the vitreous of the eye and/or more limited systemic leakage compared with a corresponding unmodified antibody. In some embodiments, the IL-6a is an IgG2 antibody.

In some aspects, the IL-6a is a relatively small IL-6a such as a fragment of an IL-6 antibody or other derivative of an antibody that is less than a full length antibody, e.g., a Fab that is derived from an IL-6 antibody. In some cases, an IL-6a is in a format that can pass from one part of a tissue to another with increased kinetics compared to a corresponding full-length IL-6 antibody. In some embodiments, the IL-6a is a Fab that has been engineered to be a larger molecule, which is more likely to have increased residence in the location to which it was delivered compared to the Fab alone, e.g., the IL-6a is dimerized through Fc domain. In certain embodiments, the Fc domain has been engineered such that the Fc moiety has ablated or reduced FcRn binding that can reduce systemic accumulation compared to the same IL-6 binding entity that includes a wild-type Fc. The engineered Fc domain can be, e.g., an IgG1 domain or an IgG2 domain.

Typically, the IL-6 antagonists described herein have a sufficiently high affinity for their target, IL-6, to be effective in ameliorating at least one undesirable effect of IL-6 and are sufficiently stable to be useful as therapeutics.

In general, the PK of an IL-6a, e.g., an IL-6a suitable for use in the eye has a sufficiently long half life in the site of delivery, e.g., the vitreous, to provide a therapeutic effect. In non-limiting examples, the PK can be a half-life of at least 8 days, 10 days, 14 days, 21 days, 28 days, or 30 days.

Identification of IL-6 Antagonists Binding to Site II

In general, any method known in the art can be used to generate a molecule that can bind to an IL-6, for example, polypeptide libraries or molecular libraries can be screened for candidate compounds in an assay for the ability of a polypeptide or compound to bind to IL-6. Once such a candidate compound is identified, the binding site of the compound can be determined using methods known in the art. For example, a molecule can be tested for the ability to bind to wild type IL-6 and the binding compared to the ability of the compound to bind to an IL-6 mutated in site I, site II, or site III. In embodiments, an IL-6a as described herein retains the ability to bind to an IL-6/IL-6Ra complex and to IL-6, and prevents binding of IL-6/IL-6Ra to gp130. In embodiments, an IL-6a as described herein can compete with gp130 for binding to IL-6/IL-6Ra complex, e.g., by binding to site II of IL-6. Such binding activities can be assayed using methods known in the art.

IL-6a candidates can be tested, for example, using an HEK-Blue™ IL-6 assay system (InvivoGen, San Diego). HEK-Blue™ IL-6 cells are HEK293 cells that are stably transfected with human IL-6R and a STAT3-inducible SEAP reporter gene. In the presence of IL-6, STAT3 is activated and SEAP is secreted. SEAP is assessed using, for example, QUANTI-Blue™ (InvivoGen, San Diego). Addition of an IL-6 antagonist to the cells prevents secretion or decreases the level of SEAP as a result of inhibiting both free and soluble receptor bound IL-6.

$K_D$ refers to the binding affinity equilibrium constant of a particular antibody-antigen interaction or antibody fragment-antigen interaction. In embodiments, an antibody or antigen binding fragment described herein binds to an antigen (e.g., IL-6) with a $K_D$ that is less than or equal to 250 pM, e.g., less than or equal to 225 pM, 220 pM, 210 pM, 205 pM, 150 pM, 100 pM, 50 pM, 20 pM, 10 pM, or 1 pM. $K_D$ can be determined using methods known in the art, for example using surface plasmon resonance, for example, using the BiaCore™ system.

$K_{off}$ refers to the dissociation rate constant of a particular antibody-antigen interaction or antibody fragment-antigen complex. The dissociation rate constant can be determined using surface plasmon resonance, for example using the BiaCore™ system. A relatively slow $K_{off}$ can contribute to desirable features of a therapeutic, e.g., permitting less frequent administration of the inhibitor to a subject in need of such treatment.

Specificity

In some embodiments, an IL-6a described herein binds specifically to a target, e.g., an IL-6. In general, "specific binding" as used herein indicates that a molecule preferentially binds to a selected molecule and displays much lower binding affinity for one or more other molecules. In embodiments, the binding affinity for another molecule is 1, 2, 3 or more orders of magnitude lower than the binding affinity for the target.

As discussed supra, IL-6 can be present as free IL-6 and as IL-6 bound to soluble IL-6Ra. Applicants have identified site II of IL-6 as an optimal target for an IL-6 antagonist compared to an inhibitor that that binds to site I of an IL-6. A site I inhibitor may inhibit binding of free IL-6 to IL-6Ra. However, such an inhibitor cannot prevent activity initiated by pre-existing IL-6/IL-6R complexes except by replacement limited by the $k_{off}$ of the complex. Another alternative, an inhibitor that binds to an IL-6Ra, is less suitable because it may have limited ability to prevent IL-6 activity unless it is present in saturating concentrations. Because the amount of IL-6 receptor is generally quite high compared to the amount of IL-6, this approach may require the administration of an undesirably large amount of a composition that inhibits IL-6 activity by binding to the receptor. In embodiments, the IL-6 antagonists described herein (e.g., the antibodies and fragments and derivatives thereof described herein) can block the activity of IL-6 even when IL-6 is bound to IL-6R. Accordingly, an advantage of an IL-6a as described herein is that relatively less of the composition may need to be administered to achieve a therapeutic effect compared to an inhibitor targeting an IL-6 receptor. Anti-receptor antibodies have been reported to be cleared rapidly by receptor mediated clearance significantly limiting their PK, therefore requiring larger doses, more frequent dosing, or both. Additionally, both anti-receptor and anti-site I IL-6 antibodies pose a problem in that they significantly increase the tissue concentration of IL-6 by disrupting the normal receptor mediated clearance pathway of the ligand, thereby exposing the subject to potentially undesirable levels of IL-6 in a tissue. Furthermore, use of an inhibitor targeting IL-6Ra may necessitate the presence of the inhibitor near both sites at which inhibition is sought and a site at which it is not desirable, e.g., systemic treatment. Use of an IL-6a that binds site II, the site to which gp130 binds, permits inhibition via free IL-6 as well as IL-6 that is bound to an IL-6R, but has not yet activated an IL-6 pathway via gp130. Accordingly, without wishing to be bound by theory, the IL-6 antagonists described herein are designed to bind to both forms of IL-6 (soluble and receptor bound), specifically the IL-6 antagonists bind to site II of IL-6, which is accessible in both forms. Compositions containing an IL-6a as described herein can inhibit both cis and trans signaling by IL-6.

In some cases compounds and methods provided herein are designed to provide an effective IL-6 blockade sufficient to treat at least one sign or symptom of an IL-6 associated disorder, for example, inhibiting angiogenesis and/or inflammation.

Compounds described herein are useful for treating eye diseases characterized by an undesirably high level of IL-6, e.g., in the vitreous (see Yuuki et al., J Diabetes Compl 15:257 (2001); Funatsu et al., Ophthalmology 110: 1690, (2003); Oh et al., Curr Eye Res 35:1116 (2010); Noma et al., Eye 22:42 (2008); Kawashima et al., Jpn J Ophthalmol 51:100 (2007); Kauffman et al., Invest Ophthalmol Vis Sci 35:900 (1994); Miao et al., Molec Vis 18:574 (2012)).

In general, an IL-6a as described herein is a potent antagonist of IL-6 signaling. In some embodiments, an IL-6a described herein has a high affinity for IL-6, for example, an IC50 less than or equal to 100 pM in an HEK-Blue IL-6 assay using 10 pM IL-6. High affinity of an IL-6a can be determined based on the $K_D$ of the IL-6a, for example, a $K_D$ of less than or equal to 1 nM, less than or equal to 500 pM, less than or equal to 400 pM, less than or equal to 300 pM, less than or equal to 240 pM, or less than or equal to 200 pM.

To produce a biologic IL-6a (e.g., a protein or polypeptide such as an antibody, fragment, or derivative thereof) that is useful for treating a disorder associated with increased IL-6 expression or activity, typically it is desirable that the biologic IL-6a have high productivity. For example, a suitable productivity is greater than or equal to 1 g/L (e.g., greater than or equal to 2 g/L, greater than or equal to 5 g/L, or greater than or equal to 10 g/L).

To effectively administer an IL-6 antagonist, it is necessary that the inhibitor have solubility compatible with the concentration at which it will be administered. For example, in the case of a full-length antibody IL-6a, the solubility is greater than or equal to 20 mg/ml, greater than or equal to 10 mg/ml, greater than or equal to 5 mg/ml, or greater than or equal to 1 mg/ml.

Furthermore, to be a viable treatment, the inhibitor must have high stability at the body temperature of the delivery and activity sites as well as storage stability. In embodiments, the inhibitor has a $T_m$ of greater than or equal to 60° C. (e.g., greater than or equal to 60° C., greater than or equal to 62.5° C., greater than or equal to 65° C., greater than or equal to 70° C., greater than or equal to 73° C., or greater than or equal to 75° C.). In embodiments, the inhibitor has a $T_{onset}$ of greater than or equal to 45° C., e.g., greater than or equal to 50° C., greater than or equal to 51° C., greater than or equal to 55° C., or greater than or equal to 60° C. Methods of determining the $T_m$ and $T_{onset}$ can be determined using methods known in the art.

Antagonists having the desired features can be selected from suitable types of molecules known in the art, for example antibodies, including fragments and derivatives of an IL-6 site II targeted antibody that generally retains or maintains sufficient features of the parent IL-6 antibody (e.g., desired binding properties). Such antagonists include $F_{ab}$ fragments, scFvs, $F_{ab}$ fragments engineered to include an Fc moiety, and full-length antibodies engineered to have a framework different from the parent IL-6 site II targeted antibody.

In some aspects, the IL-6a disclosed herein comprises a human antibody antigen-binding site that can compete or cross-compete with an antibody or fragment thereof that can bind to site II of IL-6. For example, the antibody or fragment thereof can be composed of a VH domain and a VL domain disclosed herein, and the VH and VL domains comprise a set of CDRs of an IL-6/site II binding antibody disclosed herein.

Any suitable method may be used to determine the domain and/or epitope bound by an IL-6a, for example, by mutating various sites on an IL-6. Those sites in which mutations prevent or decrease binding of the IL-6a and the IL-6 ligand are involved either directly in binding to the IL-6a or indirectly affect the binding site, e.g., by affecting conformation of the IL-6. Other methods can be used to determine the amino acids bound by an IL-6a. For example, a peptide-binding scan can be used, such as a PEPSCAN-based enzyme linked immuno assay (ELISA). In a peptide-binding scan of this type, short overlapping peptides derived from the antigen are systematically screened for binding to a binding member. The peptides can be covalently coupled to a support surface to form an array of peptides. Peptides can be in a linear or constrained conformation. A constrained conformation can be produced using peptides having a terminal cysteine (cys) residue at each end of the peptide sequence. The cys residues can be covalently coupled directly or indirectly to a support surface such that the peptide is held in a looped conformation. Accordingly, a peptide used in the method may have a cys residue added to each end of a peptide sequence corresponding to a fragment of the antigen. Double looped peptides can also be used, in which a cys residue is additionally located at or near the middle of the peptide sequence. The cys residues can be covalently coupled directly or indirectly to a support surface such that the peptides form a double-looped conformation, with one loop on each side of the central cys residue. Peptides can be synthetically generated, and cys residues can therefore be engineered at desired locations, despite not occurring naturally in the IL-6 site II sequence. Optionally, linear and constrained peptides can both be screened in a peptide-binding assay. A peptide-binding scan may involve identifying (e.g., using an ELISA) a set of peptides to which the binding member binds, wherein the peptides have amino acid sequences corresponding to fragments of an IL-6a (e.g., peptides that include about 5, 10, or 15 contiguous residues of an IL-6a), and aligning the peptides in order to determine a footprint of residues bound by the binding member, where the footprint comprises residues common to overlapping peptides. Alternatively or additionally the peptide-binding scan method can be used to identify peptides to which the IL-6a binds with at least a selected signal:noise ratio.

Other methods known in the art can be used to determine the residues bound by an antibody, and/or to confirm peptide-binding scan results, including for example, site directed mutagenesis (e.g., as described herein), hydrogen deuterium exchange, mass spectrometry, NMR, and X-ray crystallography.

Typically, an IL-6a useful as described herein is a human antibody molecule, a humanized antibody molecule, or binding fragment thereof. In general, the antibody is a monoclonal antibody. The origin of such an antibody can be human, murine, rat, camelid, rabbit, ovine, porcine, or bovine and can be generated according to methods known to those in the art.

The term "antibody molecule," as used herein, refers to a protein, or polypeptide sequence derived from an immunoglobulin molecule which specifically binds with an antigen. The antibody molecule can be a full-length antibody or a fragment thereof, e.g., an antigen binding fragment thereof. Antibodies can be polyclonal or monoclonal, multiple or single chain, or intact immunoglobulins, and may be derived from natural sources or from recombinant sources. Antibodies can be tetramers of immunoglobulin molecules. Antibody fragments or antigen binding fragments refer to at least one portion of an intact antibody, or recombinant variants thereof, and refers to the antigen binding domain, e.g., an antigenic determining variable region of an intact antibody, that is sufficient to confer recognition and specific binding of the antibody fragment to a target, such as an antigen. Examples of antibody fragments include, but are not limited to, Fab, Fab', F(ab')$_2$, and Fv fragments, scFv antibody fragments, linear antibodies, single domain antibodies such as sdAb (either VL or VH), camelid VHH domains, and multi-specific antibodies formed from antibody fragments such as a bivalent fragment comprising two Fab fragments linked by a disulfide bridge at the hinge region, and an isolated CDR or other epitope binding fragments of an antibody. An antigen binding fragment can also be incorporated into single domain antibodies, maxibodies, minibodies, nanobodies, intrabodies, diabodies, triabodies, tetrabodies, v-NAR and bis-scFv (see, e.g., Hollinger and Hudson, Nature Biotechnology 23:1126-1136, 2005). Antigen binding fragments can also be grafted into scaffolds based on polypeptides such as a fibronectin type III (Fn3) (see U.S. Pat. No. 6,703,199, which describes fibronectin polypeptide minibodies).

Exemplary IL-6 Antibodies

In general, an IL-6a comprises at least the CDRs of an antibody that can specifically bind to an IL-6 (e.g., a human IL-6), e.g., to site II of an IL-6. The structure for carrying a CDR or a set of CDRs of the invention can be an antibody heavy or light chain sequence or substantial portion thereof in which the CDR or set of CDRs is located at a location corresponding to the CDR or set of CDRs of naturally occurring VH and VL antibody variable domains encoded by rearranged immunoglobulin genes. The structures and locations of immunoglobulin variable domains can be determined by reference to Kabat, et al., 1983 (National Institutes of Health), and updates thereof findable under "Kabat" using any internet search engine.

An IL-6a, as disclosed herein, is typically an antibody molecule that generally comprises an antibody VH domain and/or VL domain. A VH domain comprises a set of heavy chain CDRs (VHCDRs), and a VL domain comprises a set of light chain CDRs (VLCDRs). Examples of such CDRS are provided herein in the Examples. An antibody molecule can comprise an antibody VH domain comprising a VHCDR1, VHCDR2 and VHCDR3 and a framework. It can alternatively or also comprise an antibody VL domain comprising a VLCDR1, VLCDR2 and VLCDR3 and a framework.

Disclosed herein are IL-6 antagonists comprising a VHCDR1 and/or VHCDR2 and/or VHCDR3 such as those disclosed herein and/or a VLCDR1 and/or VLCDR2 and/or VLCDR3 such as those disclosed herein. The IL-6a can comprise one or more, e.g., one, two, or three, CDRs of any of the antibodies, fragments or derivatives described herein. The IL-6a can comprise a set of VHCDRs (e.g., VHCDR1, VHCDR2, and/or VHCDR3), and optionally it can also comprise a set of VLCDRs (e.g., VLCDR1, VLCDR2, and/or VLCDR3). The CDRs can be derived from one or more antibodies, fragments, or derivatives described herein. For example, the VLCDRs can be derived from the same or a different antibody as the VHCDRs.

In general, a VH domain is paired with a VL domain to provide an antibody antigen-binding site. For example, the HC domain of SEQ ID NO:1, SEQ ID NO:13 or SEQ NO:25 is paired with the LC domain of SEQ ID NO:3. In some cases, a VH or VL domain alone can be used as an IL-6a.

In one aspect provided herein is an isolated antibody or antigen binding fragment comprising a heavy chain variable region comprising
(i) a VH CDR1 comprising the sequence of GYX$_1$LX$_2$NYLIE (SEQ ID NO:30),
(ii) a VH CDR2 comprising the sequence of VX$_3$TPGX$_4$GTIN (SEQ ID NO:31), and
(ii) a VH CDR3,
wherein one or more (e.g., 1, 2, 3, or all) of the following is true: X$_1$ is not A, X$_2$ is not S, X$_3$ is not I and X$_4$ is not S. In embodiments, X$_1$ is not A, X$_2$ is not S, X$_3$ is not I and X$_4$ is not S.

In embodiments, X$_1$ is V or a conservative substitution for V. In embodiments, X$_2$ is P or a conservative substitution for P. In embodiments, X$_3$ is T or a conservative substitution for T. In embodiments, X$_4$ is G or a conservative substitution for G. In embodiments, one, two, three or all of the following is true: X$_1$ is V or a conservative substitution for V, X$_2$ is P or a conservative substitution for P, X$_3$ is T or a conservative substitution for T, and X$_4$ is G or a conservative substitution for G. In embodiments, X$_1$ is V or a conservative substitution for V, X$_2$ is P or a conservative substitution for P, X$_3$ is T or a conservative substitution for T, and X$_4$ is G or a conservative substitution for G.

In embodiments, X$_1$ is selected from V, I, L and M. In embodiments, X$_1$ is selected from V, I and L. In embodiments, X$_2$ is selected from P, G, and A. In embodiments, X$_2$ is selected from P and G. In embodiments, X$_3$ is selected from T and S. In embodiments, X$_4$ is selected from G and P.

In embodiments, one or more (e.g., 1, 2, 3, or all) of the following is true: X$_1$ is V, X$_2$ is P, X$_3$ is T, and X$_4$ is G. In embodiments, X$_1$ is V, X$_2$ is P, X$_3$ is T, and X$_4$ is G.

In embodiments, the VH CDR3 comprises the sequence of SEQ ID NO:21.

In embodiments, the antibody molecule, e.g., antibody or antigen binding fragment, has increased affinity for human IL-6 and/or increased potency. In embodiments, the antibody or antigen binding fragment has increased affinity for human IL-6 and/or increased potency compared with an antibody or antigen binding fragment (e.g., an otherwise identical antibody or antigen binding fragment) comprising a sequence wherein one or more (e.g., 1, 2, 3, or all) of the following is true: X$_1$ is A, X$_2$ is S, X$_3$ is I and X$_4$ is S.

In some embodiments, the isolated antibody molecule, e.g., antibody or antigen binding fragment thereof, comprises a VH CDR1 comprising the sequence of SEQ ID NO:7, a VH CDR2 comprising the sequence of SEQ ID NO:8, and optionally a VH CDR3 comprising the sequence of SEQ ID NO:9. In an embodiment, the isolated antibody or antibody fragment thereof differs by no more than 3, 2, or 1 amino acids in each of one, two, or all of the CDRs, e.g., SEQ ID NO: 7, SEQ ID NO: 8, or SEQ ID NO: 9.

In some embodiments, the isolated antibody molecule, e.g., antibody or antigen binding fragment thereof, comprises a VH CDR1 comprising the sequence of SEQ ID NO:19, a VH CDR2 comprising the sequence of SEQ ID NO:20, and optionally a VH CDR3 comprising the sequence of SEQ ID NO:21. In an embodiment, the isolated antibody or antibody fragment thereof differs by no more than 3, 2, or 1 amino acids in each of one, two, or all of the CDRs, e.g., SEQ ID NO: 19, SEQ ID NO: 20, or SEQ ID NO: 21.

In some embodiments, the isolated antibody molecule, e.g., antibody or antigen binding fragment thereof, comprises a VL CDR1 comprising the sequence of SEQ ID NO:9 or 22, a VL CDR2 comprising the sequence of SEQ ID NO:10 or 23, and a VL CDR3 comprising the sequence of SEQ ID NO:11 or 24. In an embodiment, the isolated antibody or antibody fragment thereof differs by no more than 3, 2, or 1 amino acids in each of one, two, or all of the CDRs, e.g., SEQ ID NO: 22, SEQ ID NO: 23, or SEQ ID NO: 24.

In embodiments, the heavy chain variable region comprises a sequence that is at least 90, 91, 92, 93, 94, 95, 96, 97, 98, or 99% identical with SEQ ID NO:5. In embodiments, the heavy chain variable region consists of a sequence is at least 90, 91, 92, 93, 94, 95, 96, 97, 98, or 99% identical with SEQ ID NO:5 or differs by no more than 20, 15, 10, 5, 4, 3, 2, or 1 amino acids from SEQ ID NO:5. In embodiments, the heavy chain variable region differs by no more than 20, 15, 10, 5, 4, 3, 2, or 1 amino acids from SEQ ID NO:5, wherein the amino acid changes are not in any of the CDRs. In embodiments, the heavy chain variable region differs by 1-5 amino acids from SEQ ID NO:5.

In embodiments, the heavy chain variable region comprises a sequence that is at least 90, 91, 92, 93, 94, 95, 96, 97, 98, or 99% identical to SEQ ID NO:17. In embodiments, the heavy chain variable region consists of a sequence is at least 90, 91, 92, 93, 94, 95, 96, 97, 98, or 99% identical to SEQ ID NO:17. In embodiments, the heavy chain variable region differs by no more than 20, 15, 10, 5, 4, 3, 2, or 1 amino acids from SEQ ID NO:17. In embodiments, the heavy chain variable region differs by no more than 20, 15, 10, 5, 4, 3, 2, or 1 amino acids from SEQ ID NO:17, wherein the amino acid changes are not in any of the CDRs. In embodiments, the antibody or antigen binding fragment comprises a heavy chain variable region sequence comprising SEQ ID NO:17. In embodiments, the antibody or antigen binding fragment comprises a heavy chain variable region sequence consisting of SEQ ID NO:17.

In embodiments, the light chain variable region comprises a sequence that is at least 90, 91, 92, 93, 94, 95, 96, 97, 98, or 99% identical with SEQ ID NO:18. In embodiments, the light chain variable region consists of a sequence is at least 90, 91, 92, 93, 94, 95, 96, 97, 98, or 99% identical with SEQ ID NO:18 or differs by no more than 20, 15, 10, 5, 4, 3, 2, or 1 amino acids from SEQ ID NO:18. In embodiments, the light chain variable region differs by no more than 20, 15, 10, 5, 4, 3, 2, or 1 amino acids from SEQ ID NO:18, wherein the amino acid changes are not in any of the CDRs. In embodiments, the light chain variable region differs by 1-5 amino acids from SEQ ID NO:18.

In embodiments, the antibody molecule, e.g., antibody or antigen binding fragment, comprises a sequence that is at least 90, 91, 92, 93, 94, 95, 96, 97, 98, or 99% identical to SEQ ID NO:15. In embodiments, the antibody or antigen binding fragment comprises a sequence that differs by no more than 20, 15, 10, 5, 4, 3, 2, or 1 amino acids from SEQ ID NO:15. In embodiments, the antibody or antigen binding fragment differs by no more than 20, 15, 10, 5, 4, 3, 2, or 1 amino acids from SEQ ID NO:15, wherein the amino acid changes are not in any of the CDRs. In embodiments, the antibody or antigen binding fragment comprises SEQ ID NO:15. In embodiments, the antibody or antigen binding fragment is a Fab.

In embodiments, the antibody molecule, e.g., antibody or antigen binding fragment, comprises a sequence that is at least 90, 91, 92, 93, 94, 95, 96, 97, 98, or 99% identical to SEQ ID NO:16. In embodiments, the antibody or antigen binding fragment comprises a sequence that differs by no more than 20, 15, 10, 5, 4, 3, 2, or 1 amino acids from SEQ ID NO:16. In embodiments, the antibody or antigen binding fragment differs by no more than 20, 15, 10, 5, 4, 3, 2, or 1 amino acids from SEQ ID NO:16, wherein the amino acid changes are not in any of the CDRs. In embodiments, the antibody or antigen binding fragment comprises SEQ ID NO:16. In embodiments, the antibody or antigen binding fragment is a Fab.

In embodiments, the antibody molecule, e.g., antibody or antigen binding fragment, is an scFv. In embodiments, the antibody or antigen binding comprises or consists of the scFv sequence provided in SEQ ID NO:26 or SEQ ID NO:27. In embodiments, the antibody or antigen binding fragment comprises a sequence that is at least 90, 91, 92, 93, 94, 95, 96, 97, 98, or 99% identical to SEQ ID NO:26 or SEQ ID NO:27. In embodiments, the antibody or antigen binding fragment differs by no more than 20, 15, 10, 5, 4, 3, 2, or 1 amino acids from SEQ ID NO:26 or 27. In embodiments, the antibody or antigen binding fragment differs by no more than 20, 15, 10, 5, 4, 3, 2, or 1 amino acids from SEQ ID NO:26 or 27, wherein the amino acid changes are not in any of the CDRs. In embodiments, the antibody or antigen binding fragment comprises SEQ ID NO:26 or SEQ ID NO:27. In embodiments, the antibody or antigen binding fragment is an scFv.

In embodiments, the antibody molecule, e.g., antibody or antigen binding fragment, comprises a heavy chain sequence that is at least 90, 91, 92, 93, 94, 95, 96, 97, 98, or 99% identical to SEQ ID NO:13. In embodiments, the antibody or antigen binding fragment comprises a heavy chain sequence that differs by no more than 20, 15, 10, 5, 4, 3, 2, or 1 amino acids from SEQ ID NO:13. In embodiments, the heavy chain sequence differs by no more than 20, 15, 10, 5, 4, 3, 2, or 1 amino acids from SEQ ID NO:13, wherein the amino acid changes are not in any of the CDRs. In embodiments, the antibody or antigen binding fragment comprises a heavy chain sequence comprising SEQ ID NO:13. In embodiments, the antibody or antigen binding fragment comprises a heavy chain sequence consisting of SEQ ID NO:13.

In embodiments, the antibody molecule, e.g., antibody or antigen binding fragment, comprises a light chain sequence that is at least 90, 91, 92, 93, 94, 95, 96, 97, 98, or 99% identical to SEQ ID NO:14. In embodiments, the antibody or antigen binding fragment comprises a light chain sequence that differs by no more than 20, 15, 10, 5, 4, 3, 2, or 1 amino acids from SEQ ID NO:14. In embodiments, the light chain sequence differs by no more than 20, 15, 10, 5, 4, 3, 2, or 1 amino acids from SEQ ID NO:14, wherein the amino acid changes are not in any of the CDRs. In embodiments, the antibody or antigen binding fragment comprises a light chain sequence comprising SEQ ID NO:14. In embodiments, the antibody or antigen binding fragment comprises a light chain sequence consisting of SEQ ID NO:14.

In embodiments, the antibody molecule, e.g., antibody or antigen binding fragment, comprises one or more sequences of EBI-029, EBI-030, or EBI-031 as provided in Table 1. In embodiments, the antibody or antigen binding fragment comprises one or more domains of EBI-030 or EBI-031 as shown in FIG. 1 (e.g., one or more of FR1, CDR1, FR2, CDR2, FR3, CDR3, FR4, CH1, hinge, CH2, and CH3 of the heavy chain sequence and/or FR1, CDR1, FR2, CDR2, FR3, CDR3, FR4, and CK of the light chain sequence). In embodiments, the antibody or antigen binding fragment comprises a heavy chain and a light chain. In embodiments, the heavy and light chains are linked by one or more disulfide bonds. In embodiments, the antibody or antigen binding fragment is a Fab. In embodiments, the antibody or antigen binding fragment is an scFv. In embodiments, the antibody or antigen binding fragment is Fab, Fab', F(ab')2, scFv or Fv fragment.

In embodiments, the antibody molecule, e.g., antibody or antigen binding fragment, has increased affinity for human IL-6 and/or increased potency compared with an antibody or antigen binding fragment comprising one or more corresponding sequences of EBI-029, or sequences of an antibody described in WO2014/074905, hereby incorporated by reference in its entirety. In embodiments, antibody or antigen binding fragment has increased affinity for human IL-6 and/or increased potency compared with tocilizumab.

TABLE 1

Summary overview of sequences of EBI-029, EBI-030, and EBI-031

| Description | SEQ ID NO: | Sequence |
|---|---|---|
| EBI-029 HC (IgG2) aa sequence | SEQ ID NO: 1 | QVQLVQSGAE VKKPGSSVKV SCKASGYALS NYLIEWVRQA PGQGLEWMGV ITPGSGTINY AQKFQGRVTI TADESTSTAY MELSSLRSED TAVYYCARSR WDPLYYYALE YWGQGTTVTV SSASTKGPSV FPLAPCSRST SESTAALGCL VKDYFPEPVT VSWNSGALTS GVHTFPAVLQ SSGLYSLSSV VTVPSSNFGT QTYTCNVDHK PSNTKVDKTV ERKCCVECPP CPAPPVAGPS VFLFPPKPKD TLMISRTPEV TCVVVDVSHE DPEVQFNWYV |

TABLE 1-continued

Summary overview of sequences of EBI-029, EBI-030, and EBI-031

| Description | SEQ ID NO: | Sequence |
|---|---|---|
| | | DGVEVHNAKT KPREEQFNST FRVVSVLTVV HQDWLNGKEY KCKVSNKGLP APIEKTISKT KGQPREPQVY TLPPSREEMT KNQVSLTCLV KGFYPSDIAV EWESNGQPEN NYKTTPPMLD SDGSFFLYSK LTVDKSRWQQ GNVFSCSVMH EALHNHYTQK SLSLSPGK |
| EBI-029 HC-H311A | SEQ ID NO: 2 | QVQLVQSGAE VKKPGSSVKV SCKASGYALS NYLIEWVRQA PGQGLEWMGV ITPGSGTINY AQKFQGRVTI TADESTSTAY MELSSLRSED TAVYYCARSR WDPLYYYALE YWGQGTTVTV SSASTKGPSV FPLAPCSRST SESTAALGCL VKDYFPEPVT VSWNSGALTS GVHTFPAVLQ SSGLYSLSSV VTVPSSNFGT QTYTCNVDHK PSNTKVDKTV ERKCCVECPP CPAPPVAGPS VFLFPPKPKD TLMISRTPEV TCVVVDVSHE DPEVQFNWYV DGVEVHNAKT KPREEQFNST FRVVSVLTVV AQDWLNGKEY KCKVSNKGLP APIEKTISKT KGQPREPQVY TLPPSREEMT KNQVSLTCLV KGFYPSDIAV EWESNGQPEN NYKTTPPMLD SDGSFFLYSK LTVDKSRWQQ GNVFSCSVMH EALHNHYTQK SLSLSPGK |
| EBI-029 LC aa sequence | SEQ ID NO: 3 | DIVMTQSPDS LAVSLGERAT INCRASESVD NYGIPFMNWY QQKPGQPPKL LIYAASNRGS GVPDRFSGSG SGTDFTLTIS SLQAEDVAVY YCQQSEEVPL TFGQGTKLEI KRTVAAPSVF IFPPSDEQLK SGTASVVCLL NNFYPREAKV QWKVDNALQS GNSQESVTEQ DSKDSTYSLS STLTLSKADY EKHKVYACEV THQGLSSPVT KSFNRGEC |
| EBI-029 (IgG1) Fab HC aa sequence | SEQ ID NO: 4 | QVQLVQSGAE VKKPGSSVKV SCKASGYALS NYLIEWVRQA PGQGLEWMGV ITPGSGTINY AQKFQGRVTI TADESTSTAY MELSSLRSED TAVYYCARSR WDPLYYYALE YWGQGTTVTV SSASTKGPSV FPLAPSSKST SGGTAALGCL VKDYFPEPVT VSWNSGALTS GVHTFPAVLQ SSGLYSLSSV VTVPSSSLGT QTYICNVNHK PSNTKVDKKV EPKSCDKTHT |
| EBI-029 VH aa sequence | SEQ ID NO: 5 | QVQLVQSGAEVKKPGSSVKVSCKASGYALSNYLIE WVRQAPGQGLEWMGVITPGSGTINYAQKFQGRVTIT ADESTSTAYMELSSLRSEDTAVYYCARSRWDPLYYYALEY WGQGTTVTVSS |
| EBI-029 VL aa sequence | SEQ ID NO: 6 | DIVMTQSPDSLAVSLGERATINCRASESVDNYGIPFMNWYQQ KPGQPPKLLIYAASNRGSGVPDRFSGSGSGTDFTLTISSLQAE DVAVYYCQQSEEVPLTFGQGTKLEIKRTV |
| EBI-029 HC CDR1 | SEQ ID NO: 7 | GYALSNYLIE |
| EBI-029 HC CDR2 | SEQ ID NO: 8 | VITPGSGTIN |
| EBI-029 HC CDR3 | SEQ ID NO: 9 | SRWDPLYYYALEY |
| EBI-029 LC CDR1 | SEQ ID NO: 10 | RASESVDNYGIPFMN |
| EBI-029 LC CDR2 | SEQ ID NO: 11 | AASNRGS |
| EBI-029 LC CDR3 | SEQ ID NO: 12 | QQSEEVPLT |
| EBI-030 HC (IgG2) aa sequence | SEQ ID NO: 13 | QVQLVQSGAE VKKPGSSVKV SCKASGYVLP NYLIEWVRQA PGQGLEWMGVTTPGGGTINY AQKFQGRVTI TADESTSTAY MELSSLRSED TAVYYCARSR WDPLYYYALE YWGQGTTVTV SSASTKGPSV FPLAPCSRST SESTAALGCL VKDYFPEPVT VSWNSGALTS GVHTFPAVLQ SSGLYSLSSV VTVPSSNFGT QTYTCNVDHK PSNTKVDKTV ERKCCVECPP CPAPPVAGPS VFLFPPKPKD TLMISRTPEV TCVVVDVSHE DPEVQFNWYV DGVEVHNAKT KPREEQFNST FRVVSVLTVV HQDWLNGKEY KCKVSNKGLP APIEKTISKT KGQPREPQVY TLPPSREEMT KNQVSLTCLV KGFYPSDIAV EWESNGQPEN NYKTTPPMLD SDGSFFLYSK LTVDKSRWQQ GNVFSCSVMH EALHNHYTQK SLSLSPGK |

TABLE 1-continued

Summary overview of sequences of EBI-029, EBI-030, and EBI-031

| Description | SEQ ID NO: | Sequence |
|---|---|---|
| EBI-030 LC aa sequence | SEQ ID NO: 14 | DIVMTQSPDS LAVSLGERAT INCRASESVD NYGIPFMNWY QQKPGQPPKL LIYAASNRGS GVPDRFSGSG SGTDFTLTIS SLQAEDVAVY YCQQSEEVPLT FGQGTKLEI KRTVAAPSVF IFPPSDEQLK SGTASVVCLL NNFYPREAKV QWKVDNALQS GNSQESVTEQ DSKDSTYSLS STLTLSKADY EKHKVYACEV THQGLSSPVT KSFNRGEC |
| EBI-030 (IgG1) Fab HC aa sequence | SEQ ID NO: 15 | QVQLVQSGAE VKKPGSSVKV SCKASGYVLP NYLIEWVRQA PGQGLEWMGV TTPGGGTINY AQKFQGRVTI TADESTSTAY MELSSLRSED TAVYYCARSR WDPLYYYALE YWGQGTTVTV SSASTKGPSV FPLAPSSKST SGGTAALGCL VKDYFPEPVT VSWNSGALTS GVHTFPAVLQ SSGLYSLSSV VTVPSSSLGT QTYICNVNHK PSNTKVDKKV EPKSCDKTHT |
| EBI-030 (IgG2) Fab HC aa sequence | SEQ ID NO: 16 | QVQLVQSGAEVKKPGSSVKVSCKASGYVLPNYLIEWVRQAPGQ GLEWMGVTTPGGGTINYAQKFQGRVTITADESTSTAYMELSSL RSEDTAVYYCARSRWDPLYYYALEYWGQGTTVTVSSASTKGPS VFPLAPCSRSTSESTAALGCLVKDYFPEPVTVSWNSGALTSGV HTFPAVLQSSGLYSLSSVVTVPSSNFGTQTYTCNVDHKPSNTK VDKTVERK |
| EBI-030 VH aa sequence | SEQ ID NO: 17 | QVQLVQSGAE VKKPGSSVKV SCKASGYVLP NYLIEWVRQA PGQGLEWMGV TTPGGGTINY AQKFQGRVTI TADESTSTAY MELSSLRSED TAVYYCARSR WDPLYYYALE YWGQGTTVTV SS |
| EBI-030 VL aa sequence | SEQ ID NO: 18 | DIVMTQSPDSLAVSLGERATINCRASESVDNYGIPFMNWYQQK PGQPPKLLIYAASNRGSGVPDRFSGSGSGTDFTLTISSLQAED VAVYYCQQSEEVPLTFG QGTKLEIKRTV |
| EBI-030 HC CDR1 | SEQ ID NO: 19 | GYVLPNYLIE |
| EBI-030 HC CDR2 | SEQ ID NO: 20 | VTTPGGGTIN |
| EBI-030-HC CDR3 | SEQ ID NO: 21 | SRWDPLYYYALEY |
| EBI-030 LC CDR1 | SEQ ID NO: 22 | RASESVDNYGIPFMN |
| EBI-030 LC CDR2 | SEQ ID NO: 23 | AASNRGS |
| EBI-030 LC CDR3 | SEQ ID NO: 24 | QQSEEVPLT |
| EBT-031 IgG2 HC aa sequence | SEQ ID NO: 15 | QVQLVQSGAE VKKPGSSVKV SCKASGYVLP NYLIEWVRQA PGQGLEWMGV TTPGGGTINY AQKFQGRVTI TADESTSTAY MELSSLRSED TAVYYCARSR WDPLYYYALE YWGQGTTVTV SSASTKGPSV FPLAPCSRST SESTAALGCL VKDYFPEPVT VSWNSGALTS GVHTFPAVLQ SSGLYSLSSV VTVPSSNFGT QTYTCNVDHK PSNTKVDKTV ERKCCVECPP CPAPPVAGPS VFLFPPKPKD TLMISRTPEV TCVVVDVSHE DPEVQFNWYV DGVEVHNAKT KPREEQFNST FRVVSVLTVV ADWLNGKEY KCKVSNKGLP APIEKTISKT KGQPREPQVY TLPPSREEMT KNQVSLTCLV KGFYPSDIAV EWESNGQPEN NYKTTPPMLD SDGSFFLYSK LTVDKSRWQQ GNVFSCSVMH EALHNHYTQK SLSLSPGK |
| scFv VH-VL aa sequence | SEQ ID NO: 26 | QVQLVQSGAEVKKPGSSVKVSCKASGYVLPNYLIEWVRQAPGQ GLEWMGVTTPGGGTINYAQKFQGRVTITADESTSTAYMELSSL RSEDTAVYYCARSRWDPLYYYALEYWGQGTTVTVSSGGGGSGG GGSGGGGSDIVMTQSPDSLAVSLGERATINCRASESVDNYGIP FMNWYQQKPGQPPKLLIYAASNRGSGVPDRFSGSGSGTDFTLT ISSLQAEDVAVYYCQQSEEVPLTFGQGTKLEIKRTV |
| scFv VL-VH aa sequence | SEQ ID NO: 27 | DIVMTQSPDSLAVSLGERATINCRASESVDNYGIPFMNWYQQK PGQPPKLLIYAASNRGSGVPDRFSGSGSGTDFTLTISSLQAED VAVYYCQQSEEVPLTFGQGTKLEIKRTVGGGGSGGGGSGGGGS QVQLVQSGAEVKKPGSSVKVSCKASGYVLPNYLIEWVRQAPGQ GLEWMGVTTPGGGTINYAQKFQGRVTITADESTSTAYMELSSL RSEDTAVYYCARSRWDPLYYYALEYWGQGTTVTVSS |

TABLE 1-continued

Summary overview of sequences of EBI-029, EBI-030, and EBI-031

| Description | SEQ ID NO: | Sequence |
| --- | --- | --- |
| 030 IgG2 constant region | SEQ ID NO: 28 | ASTKGPSVFPLAPCSRSTSESTAALGCLVKDYFPEPVTVSWNS GALTSGVHTFPAVLQSSGLYSLSSVVTVPSSNFGTQTYTCNVD HKPSNTKVDKTVERKCCVECPPCPAPPVAGPSVFLFPPKPKDT LMISRTPEVTCVVVDVSHEDPEVQFNWYVDGVEVHNAKTKPRE EQFNSTFRVVSVLTVVHQDWLNGKEYKCKVSNKGLPAPIEKTI SKTKGQPREPQVYTLPPSREEMTKNQVSLTCLVKGFYPSDIAV EWESNGQPENNYKTTPPMLDSDGSFFLYSKLTVDKSRWQQGNV FSCSVMHEALHNHYTQKSLSLSPGK |
| 031 IgG2 constant region | SEQ ID NO: 29 | ASTKGPSV FPLAPCSRST SESTAALGCL VKDYFPEPVT VSWNSGALTS GVHTFPAVLQ SSGLYSLSSV VTVPSSNFGT QTYTCNVDHK PSNTKVDKTV ERKCCVECPP CPAPPVAGPS VFLFPPKPKD TLMISRTPEV TCVVVDVSHE DPEVQFNWYV DGVEVHNAKT KPREEQFNST FRVVSVLTVV AQDWLNGKEY KCKVSNKGLP APIEKTISKT KGQPREPQVY TLPPSREEMT KNQVSLTCLV KGFYPSDIAV EWESNGQPEN NYKTTPPMLD SDGSFFLYSK LTVDKSRWQQ GNVFSCSVMH EALHNHYTQK SLSLSPGK | aa = amino acid; na = nucleic acid; HC = heavy chain; LC = light chain; VH = heavy chain variable region; VL = light chain variable region In some aspects, the IL-6a is an antibody molecule, fragment, or derivative thereof that comprises (i) a VH domain sequence that has at least 60, 70, 80, 85, 90, 95, 98 or 99% amino acid sequence identity with a VH domain described herein (e.g., SEQ ID NO:17), or (ii) a set of VHCDRs (e.g., VHCDR1, VHCDR2, and/or VHCDR3) from the VH domain sequence. In embodiments, the antibody molecule, fragment, or derivative thereof comprises a VHCDR1, VHCDR2, and VHCDR3 of SEQ ID NO:17. In embodiments, the antibody molecule, fragment, or derivative thereof comprises a VHCDR1, VHCDR2, and VHCDR3 that collectively differ from the VHCDR1, VHCDR2, and VHCDR3 of SEQ ID NO:17 by no more than 1, no more than 2, no more than 3, no more than 4, or no more than 5 amino acids.

The antibody molecule, fragment, or derivative thereof can optionally also comprise (i) a VL domain sequence that has at least 60, 70, 80, 85, 90, 95, 98 or 99% amino acid sequence identity with a VL domain described herein, e.g., a VL domain of SEQ ID NO: 18, or (ii) a set of VLCDRs (e.g., VLCDR1, VLCDR2, and/or VLCDR3) from the VL domain. In embodiments, the antibody molecule, fragment or derivative thereof comprises VLCDR1, VLCDR2, and VLCDR3 of SEQ ID NO: 18. In embodiments, the antibody molecule, fragment, or derivative comprises a VLCDR1, VLCDR2, and VLCDR3 that collectively differ from the VLCDR1, VLCDR2, and VLCDR3 of SEQ ID NO:18 by no more than 1, no more than 2, no more than 3, no more than 4, or no more than 5 amino acids. Algorithms that can be used to calculate percent identity of two amino acid sequences include e.g., BLAST, FASTA, or the Smith-Waterman algorithm, e.g., employing default parameters.

An IL-6a as described herein can comprise antibody constant regions or parts thereof, e.g., human antibody constant regions or parts thereof. For example, a VL domain may be attached at its C-terminal end to antibody light chain constant domains including human CK or CL chains. Similarly, an IL-6a based on a VH domain can be attached at its C-terminal end to all or part (e.g., a CH1 domain) of an immunoglobulin heavy chain derived from any antibody isotype, e.g. IgG, IgA, IgE and IgM and any of the isotype sub-classes, particularly IgG1, IgG2, IgG3 and IgG4. In embodiments, the antibody or antigen binding fragment is engineered to reduce or eliminate ADCC activity.

In an embodiment, the antibody of the invention is an IgG2 antibody. In an embodiment, the antibody of the invention comprises an IgG2 framework, IgG2 constant region, or IgG2 Fc region as described herein.

Figure 10:
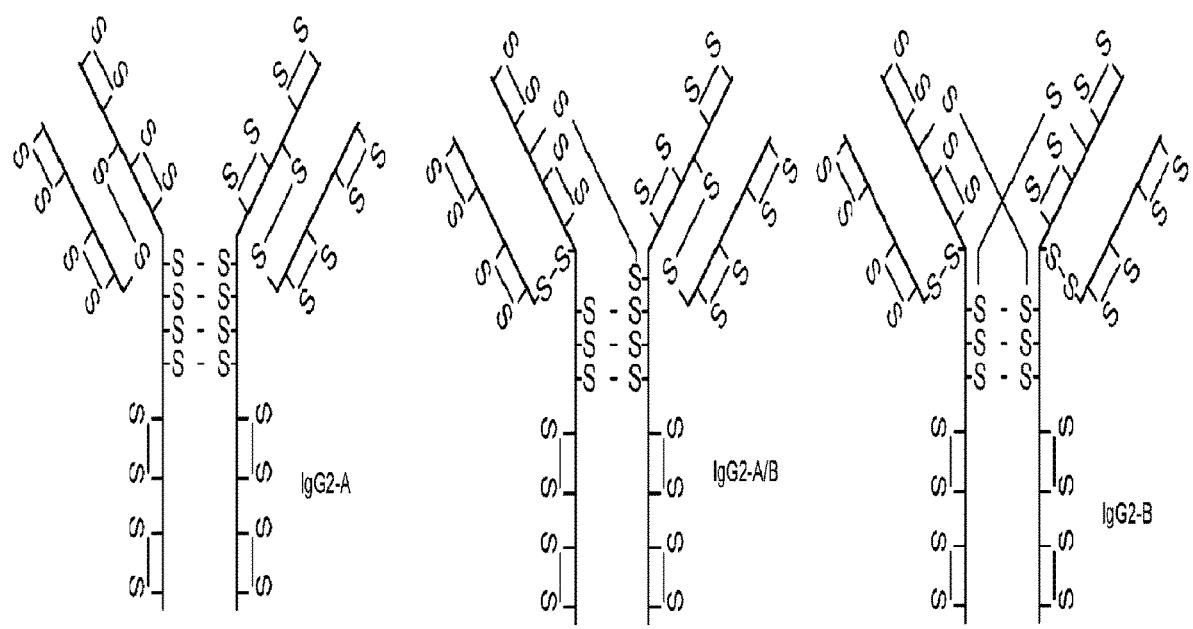
FIG. 10 shows a schematic diagram of the three different structural isoforms of IgG2 antibodies due to disulfide shuffling.

IgG2 antibodies can exist as three major structural isoforms: IgG2-A, IgG2-B, and IgG2-AB (Wypych J. et al. *Journal of Biological Chemistry.* 2008, 283:16194-16205). This structural heterogeneity is due to different configurations of the disulfide bonds that link the Fab arms to the heavy chain hinge region. In the IgG2-A isoform, there are no disulfide bonds linking the Fab arms to the hinge region. In the IgG2-B isoform, both Fab arms have disulfide bonds linking the heavy and light chain to the hinge region. The IgG2-AB isoform is a hybrid between the IgG2-A and IgG2-B isoforms, with only one Fab arm having disulfide bonds linking the heavy and light chain of the one Fab arm to the hinge region. The conversion of an IgG2 antibody between two or all of the different structural isoforms, also referred to as disulfide shuffling, occurs naturally in vivo and in vitro for both naturally-occurring and recombinant antibodies. As a result, formulations of IgG2 antibodies in the art comprise a heterogeneous mixture of IgG2-A, IgG2-B, and IgG2-AB isoforms. The different IgG2 isoforms can have unique and different functional properties, such as differences in stability, aggregation, viscosity, Fc receptor binding, or potency. Presence of multiple isoforms or increased levels of a particular isoform in a IgG2 antibody formulation can negatively affect stability, aggregation, or potency. Some fragments of an IgG2 antibody that can still undergo disulfide shuffling and exist in any of the structural isoforms A, A/B, and/or B can be readily envisioned, e.g., fragments that retain the residues that participate in the shuffling disulfide bonds (e.g., as shown in FIG. 10), e.g., the fragment comprises at least an IgG2 hinge region.

The present invention provides formulations comprising an antibody or a fragment thereof with the advantage of primarily existing in the IgG2-A or IgG2-A/B isoform. The antibody or a fragment thereof does not exist in the IgG2-B isoform, or does not exist in the IgG2-B isoform for a substantial amount of time, thereby resulting in a very low level of IgG2-B isoform in a composition or formulation at a given time. Thus, compositions and formulations comprising the antibody described herein are less heterogeneous than other IgG2 antibodies known in the art, and therefore, more preferred for use in a therapeutic application.

Compositions and formulations comprising the antibody comprise primarily IgG2-A and/or IgG2-A/B isoforms of the antibody. In an embodiment, a composition comprising an antibody described herein comprises at least 50, 60, 70, 80, 90, 95, 96, 97, 98, or 99% of the IgG2-A or IgG2-A/B isoforms of the antibody. In an embodiment, a composition comprising an antibody described herein comprises at least 60, 70, 80, 90, 95, 96, 97, 98, or 99% of the IgG2-A and IgG2-A/B isoforms collectively. In such embodiments, a composition comprising an antibody described herein does not comprise a substantial amount of the IgG2-B isoforms of the antibody. For example, the composition comprises less than 10%, 5%, 2%, 1%, 0.5%, or 0.1% of the IgG2-B isoforms of the antibody.

In some cases, an antibody of the invention is further modified using methods known in the art create a sequence having a specific allotype, for example an allotype that predominates in a population having a particular geographic origin. In some cases, the human heavy chain constant region is modified for this purpose.

An IL-6a can be an antibody molecule, binding fragment thereof, or variant, having one or more CDRs, for example, a set of CDRs, within an antibody framework. For example, one or more CDRs or a set of CDRs of an antibody (e.g., an antibody or fragment or derivative thereof as described herein) may be grafted into a framework (e.g., human framework) to provide an antibody molecule. The framework regions can be derived from human germline gene sequences, or be non-germline in origin.

VH and/or VL framework residues can be modified as discussed and exemplified herein e.g., using site-directed mutagenesis.

Amino acid changes can be made in one or more framework regions and/or one or more CDRs derived from an antibody IL-6a targeted to site II of IL-6 (termed herein a "reference IL-6 antibody") using methods and parameters known in the art. Also included herein is a resulting IL-6 antagonist that retains binding to site II of an IL-6 (e.g., site II of a human IL-6) and typically has at least the same binding or increased affinity compared to the reference IL-6 antibody. In some cases, to improve a parameter such as stability, a change that results in a decrease in binding affinity of the derived IL-6a compared to the reference IL-6a (e.g., the reference antibody) can be introduced to create a useful IL-6a. In some embodiments, e.g., in some cases in which the reference relates to FcRn binding or a pharmacokinetic (PK) parameter such as half-life in the vitreous or systemic half-life (e.g., in blood, plasma, serum, lymph, liver, kidney, other tissue, or body fluid), a reference antibody may be an antibody that does not specifically bind an IL-6.

A change in the amino acid sequence of an IL-6a polypeptide can include substituting one or more amino acid residue(s) with a non-naturally occurring or non-standard amino acid, modifying one or more amino acid residue into a non-naturally occurring or non-standard form, or inserting one or more non-naturally occurring or non-standard amino acid into the sequence. Examples of numbers and locations of alterations in sequences of the invention are described elsewhere herein. Naturally occurring amino acids include the 20 "standard" L-amino acids identified as G, A, V, L, I, M, P, F, W, S, T, N, Q, Y, C, K, R, H, D, E by their standard single-letter codes. Non-standard amino acids include any other residue that may be incorporated into a polypeptide backbone or result from modification of an existing amino acid residue. Non-standard amino acids may be naturally occurring or non-naturally occurring. Several naturally occurring non-standard amino acids are known in the art, such as 4-hydroxyproline, 5-hydroxylysine, 3-methylhistidine, and N-acetylserine. Those amino acid residues that are derivatized at their N-alpha position will only be located at the N-terminus of an amino-acid sequence. The amino acid is typically an L-amino acid. In some cases the amino acid is a D-amino acid. Alteration may therefore comprise modifying an L-amino acid into, or replacing it with, a D-amino acid. Methylated, acetylated and/or phosphorylated forms of amino acids are also known, and amino acids in the present invention may be subject to such modification.

Amino acid sequences in antibody domains and binding members of the invention can comprise non-natural or non-standard amino acids as discussed herein. Non-standard amino acids (e.g., D-amino acids) can be incorporated into an amino acid sequence using methods known in the art, for example in synthesis of the molecule or by post-synthesis modification or replacement of an amino acid. In some cases, a D-amino acid is used to increase PK of an IL-6a.

Novel VH or VL regions carrying CDR-derived sequences of the invention may be generated using random mutagenesis of one or more selected VH and/or VL nucleic acid sequences to generate mutations within the entire variable domain. For example, error-prone PCR can be used (Chao et al., Nature Protocols, 1:755-768 (2006)). In some embodiments one or two amino acid substitutions are made within an entire variable domain or set of CDRs. Other methods know in the art can be used to generate mutations, for example site-directed mutagenesis, typically in one or more CDRs.

One method for producing an antibody IL-6a, is to alter a VH domain such as those disclosed herein by adding, deleting, substituting or inserting one or more amino acids. The altered VH domain can be combined with a VL domain (e.g., a VL domain disclosed herein), which can also be altered as described herein and using methods known in the art. Such altered molecules are tested for their ability to bind to site II of IL-6 and optionally for other desired properties such as increased affinity compared to a reference molecule. In some cases, a variant VH or VL domain can have 1, 2, 3, 4, or 5 such alterations (e.g., 1, 2, 3, 4, or 5 amino acid substitutions).

In embodiments, an IL-6a of the invention is a fragment of an antibody that binds to site II of an IL-6 and comprises an antigen binding site, e.g., can bind to site II of an IL-6. Antibody fragments of the invention are generally obtained starting with a reference (parent) antibody molecule, such as an antibody molecule comprising SEQ ID NO:13 and SEQ ID NO:14. Antibody fragments can be generated using methods known in the art such as recombinant DNA, enzymatic cleavage (for example, using pepsin or papain), chemical cleavage of an antibody (for example, chemical reduction of disulfide bridges). Antibody fragments that comprise an antibody antigen-binding site include, but are not limited to, molecules such as Fab, Fab', Fab'-SH, scFv, Fv, dAb, Fd, and disulfide stabilized variable region (dsFv). Various other antibody molecules including one or more antibody antigen-binding sites can be engineered, including for example F(ab')2, F(ab)3, diabodies, triabodies, tetrabodies, and minibodies. Examples of antibody molecules and methods for their construction and use are described in Holliger and Hudson, 2005, Nat Biotechnol 23:1126-1136.

Non-limiting examples of binding fragments are a Fab fragment composed of VL, VH, constant light chain domain (CL) and constant heavy chain domain 1 (CH1) domains; an Fd fragment composed of VH and CH1 domains; an Fv fragment composed of the VL and VH domains of a single antibody; a dAb fragment composed of a VH or a VL domain; isolated CDR regions; an F(ab')2 fragment, a bivalent fragment comprising two linked Fab fragments; a single chain Fv molecule (scFv), in which a VH domain and a VL domain are linked by a peptide linker which allows the two domains to associate to form an antigen binding site; a bispecific single chain Fv dimer (for example as disclosed in WO 1993/011161) and a diabody, which is a multivalent or multispecific fragment constructed using gene fusion (for example as disclosed in WO94/13804). Fv, scFv, or diabody molecules can be stabilized by the incorporation of disulfide bridges linking the VH and VL domains. Minibodies comprising an scFv joined to a CH3 domain can also be used as an IL-6a. Other fragments and derivatives of an antibody that can be used as an IL-6a include a Fab', which differs from a Fab fragment by the addition of a few amino acid residues at the carboxyl terminus of the heavy chain CH1 domain, including one or more cysteines from the antibody hinge region, and Fab'-SH, which is a Fab' fragment in which the cysteine residue(s) of the constant domains bear a free thiol group.

In some cases, an IL-6a that is an antibody fragment has been chemically modified to improve or introduce a desirable property, for example PEGylation to increase half-life or incorporation.

A dAb (domain antibody) is a small monomeric antigen-binding fragment of an antibody (the variable region of an antibody heavy or light chain. VH dAbs occur naturally in camelids (e.g., camels and llamas) and can be produced by immunizing a camelid with a target antigen, isolating antigen-specific B cells and directly cloning dAb genes from individual B cells. An IL-6a of the present invention can be a dAb comprising a VH or VL domain substantially as set out herein, or a VH or VL domain comprising a set of CDRs substantially as set out herein.

Antibodies of the invention include bispecific antibodies in which two different variable regions are combined in the same molecule. An Il-6a can be incorporated as part of a bispecific antibody prepared using methods known in the art, for example, prepared chemically or from hybrid hybridomas. Such a molecule can be a bispecific antibody fragment of a type discussed above. One non-limiting example of a method for generating a bispecific antibody is BiTE™ technology in which the binding domains of two antibodies with different specificity can be used and directly linked via short flexible peptides. This combines two antibodies on a short single polypeptide chain. Diabodies and scFv can be constructed without an Fc region, using only variable domains, potentially reducing the effects of anti-idiotypic reaction. Bispecific antibodies can be constructed as entire IgG, as bispecific Fab'2, as Fab'PEG, as diabodies or else as bispecific scFv. Further, two bispecific antibodies can be linked using routine methods known in the art to form tetravalent antibodies.

Bispecific diabodies, as opposed to bispecific whole antibodies, are useful, in part because they can be constructed and expressed in *E. coli*. Diabodies (and many other polypeptides, such as antibody fragments) of appropriate binding specificities can be readily selected using phage display (WO 1994/13804) from libraries. If one arm of the diabody is to be kept constant, for example, with a specificity directed against site II of IL-6, then a library can be made where the other arm is varied and an antibody of appropriate specificity selected.

Bispecific whole antibodies may be made by alternative engineering methods as described in described in WO 1996/27011, WO 1998/50431 and WO 2006/028936.

In some cases, an IL-6a of the invention comprises an antigen-binding site within a non-antibody molecule, for example, by incorporating one or more CDRs, e.g. a set of CDRs, in a non-antibody protein scaffold, as discussed further below. In some cases, the CDRs are incorporated into a non-antibody scaffold. An IL-6 site II binding site can be provided by an arrangement of CDRs on non-antibody protein scaffolds, such as fibronectin or cytochrome B, or by randomizing or mutating amino acid residues of a loop within a protein scaffold to confer binding specificity for an IL-6 site II. Scaffolds for engineering novel binding sites in proteins are known in the art. For example, protein scaffolds for antibody mimics are disclosed in WO200034784, which describes proteins (antibody mimics) that include a fibronectin type III domain having at least one randomized loop. A suitable scaffold into which to graft one or more CDRs, e.g., a set of HCDRs, can be provided by any domain member of the immunoglobulin gene superfamily. The scaffold can be a human or non-human protein. An advantage of a non-antibody protein scaffold is that it can provide an antigen-binding site in a scaffold molecule that is smaller and/or easier to manufacture than at least some antibody molecules. Small size of a binding member may confer useful physiological properties, such as an ability to enter cells, penetrate deep into tissues or reach targets within other structures, or to bind within protein cavities of the target antigen. Typical are proteins having a stable backbone and one or more variable loops, in which the amino acid sequence of the loop or loops is specifically or randomly mutated to create an antigen-binding site that binds the target antigen. Such proteins include the IgG-binding domains of protein A from *S. aureus*, transferrin, tetranectin, fibronectin (e.g., using the 10th fibronectin type III domain), lipocalins as well as gamma-crystalline and other Affilin™ scaffolds (Scil Proteins, Halle, Germany). Examples of other approaches include synthetic microbodies based on cyclotides—small proteins having intra-molecular disulfide bonds, microproteins (e.g., Versabodies™, Amunix Inc., Mountain View, CA) and ankyrin repeat proteins (DARPins, e.g., from Molecular Partners AG, Zurich-Schlieren, Switzerland). Such proteins also include small, engineered protein domains such as, for example, immuno-domains (see for example, U.S. Patent Publication Nos. 2003/082630 and 2003/157561). Immuno-domains contain at least one complementarity determining region (CDR) of an antibody.

An IL-6a can comprise additional amino acids, e.g., to impart to the molecule another functional characteristic in addition to ability to bind antigen.

In some cases, an IL-6a carries a detectable label, or is conjugated to a toxin or a targeting moiety or enzyme (e.g., via a peptidyl bond or linker). For example, an IL-6a can comprise a catalytic site (e.g., in an enzyme domain) as well as an antigen binding site (e.g., binding site for site II of an IL-6), such that the antigen binding site binds to the antigen and thus targets the catalytic site to IL-6 or IL-6/IL-6R complex. The catalytic site can, in some cases, further inhibit a biological function of an IL-6, e.g., by cleavage of the IL-6, IL-6R, or other molecule that is associated with the IL-6a/IL-6 complex.

In some aspects, the invention includes an antibody IL-6a that has been modified compared to a reference antibody to alter, for example, increase, decrease, or eliminate, the biological effect function of the IL-6a. In one example, the Fc region is modified or the parental Fc domain is replaced with a modified Fc domain to alter the pharmacokinetics of the modified IL-6a compared to the unmodified parent. In some embodiments, the IL-6a is engineered to have an IgG2 framework. In other embodiments, the IL-6a is in an IgG1 or IgG2 framework and has a modified Fc that increases the binding affinity of the IL-6a at pH 6.0 and does not substantially alter the binding affinity at pH 7.0 compared to a parent or other reference IL-6a. In embodiments, the Fc domain is modified and the IL-6a has reduced systemic accumulation, a decreased half-life, and/or increased systemic clearance compared to a parent or other reference IL-6a.

In some embodiments, an antibody IL-6a is modified to increase complement fixation and complement-dependent cytotoxicity. In other aspects, the antibody IL-6a is modified to increase the ability of the antibody compared to a reference antibody to activate effector cells and participate in antibody-dependent cytotoxicity (ADCC). In some cases, the antibodies as disclosed herein can be modified both to enhance their capability of activating effector cells and participating in antibody-dependent cytotoxicity (ADCC) and to enhance their capability of fixing complement and participating in complement-dependent cytotoxicity (CDC).

In some embodiments, the antibodies disclosed herein are modified to reduce their ability to fix complement and participate in complement-dependent cytotoxicity (CDC). In other embodiments, the antibodies are modified to reduce their ability to activate effector cells and participate in antibody-dependent cytotoxicity (ADCC). In yet other embodiments, an antibody as disclosed herein can be modified both to reduce its ability to activate effector cells and participate in antibody-dependent cytotoxicity (ADCC) and to reduce its ability to fix complement and participate in complement-dependent cytotoxicity (CDC).

Formulation

The formulation described herein includes an IL-6 antagonist, e.g., an IL-6 antibody or fragment thereof, present in the formulation in a concentration of from 0.1 mg/ml to 100 mg/ml, 0.1-80 mg/ml, 0.1 to 50 mg/ml, 0.1 mg/ml to 20 mg/ml, 0.1 mg/ml to 5 mg/ml, 0.1 mg/ml to 1 mg/ml, 1 mg/ml to 100 mg/ml; 5 mg/ml to 100 mg/ml; 5 mg/ml to 30 mg/ml; 10 mg/ml to 100 mg/ml; 10 mg/ml to 30 mg/ml; 20 mg/ml to 100 mg/ml; 30 mg/ml to 100 mg/ml; 40 mg/ml to 100 mg/ml; 50 mg/ml to 100 mg/ml; 60 mg/ml to 100 mg/ml; 1 mg/ml to 80 mg/ml; 5 mg/ml to 80 mg/ml; 10 mg/ml to 80 mg/ml; 20 mg/ml to 80 mg/ml; 40 mg/ml to 80 mg/ml; 50 mg/ml to 80 mg/ml; 60 mg/ml to 80 mg/ml; 1 mg/ml to 60 mg/ml; 5 mg/ml to 60 mg/ml; 10 mg/ml to 60 mg/ml; 20 mg/ml to 60 mg/ml; 30 mg/ml to 60 mg/ml; 40 mg/ml to 60 mg/ml; or 50 mg/l to 60 mg/ml. For example, the formulation contains about 1 mg/ml, 2 mg/ml, 5 mg/ml, 10 mg/ml, 20 mg/ml, 25 mg/ml, 30 mg/ml, 40 mg/ml, 50 mg/ml, or 55 mg/ml of an IL-6 antagonist, e.g., an IL-6 antibody or fragment described herein.

The IL-6 antagonist, e.g., IL-6 antibody or fragment thereof described herein, is formulated with other pharmaceutically effective excipients. In one embodiment, the IL-6 antagonist, e.g., IL-6 antibody or fragment thereof described herein, is formulated with one or more, or all of the following: a buffer, a surfactant, and a tonicity agent (e.g., a sugar and/or a salt). In one embodiment, the formulation comprises an IL-6a, e.g., an IL-6 antibody or fragment thereof as described herein, and one or more buffers (e.g., buffering agents). In one embodiment, the formulation further comprises one or more surfactants. In one embodiment, the formulation further comprises one or more tonicity agents. In one embodiment, the formulation comprises two or more tonicity agents, e.g., a salt and a sugar. In one embodiment, the formulation further comprises one or more of a chelating agent, one or more of a preserving agent, one or more of an antioxidant, and/or one or more of an amino acid. In one embodiment, the formulation further comprises a one or more additional therapeutic agents, e.g., a second therapeutic agent. Exemplary excipients and additional therapeutic agents are described further herein.

Buffers

Different buffers suitable for administration to a subject are known in the art. In general, a suitable buffer is selected by conducting a stability study in which the polypeptide of interest, e.g., an IL-6a, e.g., an IL-6 antagonist or fragment thereof, is exposed to various buffers at various pH's, concentrations, temperatures, and for various times. Buffers can be selected, for example by placing the polypeptide of interest, e.g., an IL-6a, e.g., an IL-6 antibody or fragment thereof, in the buffer and subjecting the samples to elevated temperatures (accelerated stability testing) then test for physical stability (precipitation by visual inspection) or chemical stability, for example, by monitoring deamidation by weak cation exchange chromatography or oxidation by reversed phase chromatography. Additional assays can include monitoring of A280, SDS-PAGE, pH, and osmolality. A buffer that provides the best physical and chemical stability is selected. In embodiments, the buffer provides the liquid composition with the desired pH close also provides enhanced antibody stability and resistance to aggregation, oxidation and fragmentation.

Examples of buffering agents include, but are not limited to, acetate, succinate, gluconate, citrate, histidine, acetic acid, phosphate, phosphoric acid, ascorbate, tartartic acid, maleic acid, glycine, lactate, lactic acid, ascorbic acid, imidazole, bicarbonate and carbonic acid, succinic acid, sodium benzoate, benzoic acid, gluconate, edetate, acetate, malate, imidazole, tris (tricine), phosphate, and mixtures thereof. In one embodiment, the buffering agent is selected from the group consisting of acetate, citrate, histine, phosphate, and tris (tricine).

In some embodiments, the buffering agent is present in an amount of from about 1 mM to about 50 mM, from about 5 mM to about 40 mM, from about 5 mM to about 30 mM, from about 5 mM to about 20 mM, from about 10 mM to about 50 mM, from about 10 mM to about 40 mM, from about 10 mM to about 30 mM, from about 15 mM to about 50 mM, from about 15 mM to about 40 mM, from about 15 mM to about 30 mM, from about 15 mM to about 25 mM, from about 18 mM to about 22 mM. In some embodiments, the buffering agent is present in an amount of about 10 mM, about 15 mM, about 16 mM, about 17 mM, about 18 mM, about 19 mM, about 20 mM, about 21 mM, about 22 mM, about 23 mM, about 24 mM, about 25 mM, about 30 mM, about 35 mM, about 40 mM, about 45 mM or about 50 mM. In one embodiment, the formulation comprises concentration of a buffer, e.g., a histidine buffer, which is between at least 10% less than and at least 10% greater than a concentration of a buffer disclosed herein. By way of example, in one embodiment the formulation comprises 20 mM+/−10% of buffer. In one embodiment, the formulation further comprises 20 mM+/−20% buffer. In one embodiment, the formulation further comprises 20 mM+/−30% buffer.

In one embodiment, the buffering agent is histidine, wherein the histidine can comprise either L-histidine or D-histidine, a solvated form of histidine, a hydrated form (e.g., monohydrate) of histidine, or an anhydrous form of histidine or a mixture thereof. In one embodiment, the buffering agent is histidine hydrochloride (HCl). In one embodiment, the histidine buffer is present at a concentration of about Surfactants In another aspect the formulations provided herein include one or more surfactants. Without wishing to be bound by theory, use of a surfactant can be useful, e.g., for reducing adhesion of a molecule to a container, reducing aggregation of a protein particularly under conditions of agitation. Suitable surfactants and concentrations of such surfactants can be determined by testing whether the surfactant prevents aggregation in agitation studies. Methods of conducting such studies are known in the art. For example, it can be determined whether surfactant is needed to prevent precipitation from agitation stress. In such experiments, typically, a screen is performed using agitation and analysis. Examples of concentrations used for such studies are 0.01%, 0.02%, 0.06%, and 0.1% w/v surfactant, e.g., poloxamer 188. In embodiments, aggregation and/or precipitation are assessed using analysis by spectrophotometry (A280), visual inspection, size exclusion chromatography (SEC), light obscuration (e.g., using a HIAC device), or Micro-Flow Imaging™ (MFI, ProteinSimple, Santa Clara, CA). A surfactant is generally selected for use in a formulation that is associated with the least amount of precipitation, e.g., no visible precipitation, or particle count that meets guidelines for particulate matter in injections (see, e.g., USP <788>) or guidelines for particulate matter in ophthalmic solutions (see, e.g., USP<789>).

Surfactants suitable for use in the disclosed formulations can include, but are not limited to: polysorbates (e.g., polysorbate 20, polysorbate 21, polysorbate 40, polysorbate 60, polysorbate 61, polysorbate 65, polysorbate 80, polysorbate 81, polysorbate 85, and mixtures thereof), poloxamers (e.g., poloxamer P188), tritons (e.g., Triton X100 or Triton X405), sodium dodecyl sulfate, sodium laurel sulfate, sodium octyl glycoside, lauryl-sulfobetaine, myhstyl-sulfobetaine, linoleyl-sulfobetaine, stearyl-sulfobetaine, lauryl-sarcosine, myristyl-sarcosine, linoleyl-sarcosine, stearyl-sarcosine, linoleyl-betaine, myristyl-betaine, cetyl-betaine, lauroamidopropyl-betaine, cocamidopropyl-betaine, linoleamidopropyl-betaine, myristamidopropyl-betaine, palmidopropyl-betaine, isostearamidopropyl-betaine, myristamidopropyl-dimethylamine, palmidopropyl-dimethylamine, isostearamidopropyl-dimethylamine, sodium methyl cocoyl-taurate, disodium methyl oleyl-taurate, dihydroxypropyl PEG 5 linoleammonium chloride, polyethylene glycol, polypropylene glycol, Cremophor® EL, tyloxapol, octoxynol 40, and polyoxyl 40 stearate and mixtures thereof. In one embodiment, the surfactant is selected from the group consisting of polysorbate 20 (also referred to herein as Tween 20), polysorbate 80 (also referred to herein as Tween 80), and poloxamer P188.

In certain embodiments, a formulation contains a surfactant (e.g., polysorbate 20 or Tween 20) in a concentration ranging from about 0.001% to about 10%, from about 0.005% to about 5%, from about 0.01% to about 1%, from about 0.05% to about 0.5%, from about 0.05% to about 0.1%, from about 0.01% to about 0.8%, from about 0.01% to about 0.05%, from about 0.02% to about 0.08%, from about 0.02% to about 0.05%, or from about 0.02% to about 0.05% w/v. In one embodiment, the formulation contains a surfactant at a concentration of about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5% or about 1% w/v. In one embodiment, the formulation comprises concentration of a surfactant, which is between at least 10% less than and at least 10% greater than a concentration of a surfactant disclosed herein. By way of example, in one embodiment the formulation comprises 0.03%+/−0.003% of surfactant. In one embodiment, the formulation further comprises 0.03%+/−0.006% of surfactant. In one embodiment, the formulation further comprises 0.03%+/−0.01% of surfactant.

In embodiments, the surfactant is polysorbate 20 (e.g., Tween 20), polysorbate 80 (Tween 80), or poloaxamer 188. In such embodiments, polysorbate 20, polysorbate-80, or poloxamer 188 is present in the formulation at a concentration ranging from about 0.01% to about 0.2%, about 0.01% to about 0.1%, 0.01% to about 0.05%, 0.01% to about 0.03%, 0.02% to about 0.8%, 0.02%, to about 0.05%, 0.02% to about 0.04% w/v. In one embodiment, polysorbate 20, polysorbate-80, or poloxamer 188 is present in the formulation at a concentration of about 0.01%, 0.02%, 0.03%, 0.04%, or 0.05% w/v, e.g., at a concentration of 0.03% w/v. In any of the formulations described herein, polysorbate-20 (Tween-20), polysorbate-80 (Tween-80), and poloxamer 188 are interchangeable.

Tonicity Agents

In another aspect, the formulations described herein include one or more tonicity agents. For example, a formulation described herein may contain two tonicity agents. Tonicity agents refers to an excipient that can adjust the osmotic pressure of a formulation to isotonic to that the formulation is physiologically compatible with the cells of the of the body tissue or organ of the subject. In embodiments, a tonicity agent can be a polyol such as a sugar (e.g., a saccharide), a carbohydrate, a salt, or mixtures thereof. Without committing to any theory, such agents may contribute to the stability of an IL-6 antagonist, e.g., an IL-6 antibody or fragment thereof as described herein.

In one embodiment, the tonicity agent is a polyol. Polyols, as used herein, refers to an excipient with multiple hydroxyl groups, and includes sugars (reducing and non-reducing sugars, sugar alcohols, and sugar acids. In an embodiment, the polyol has a molecular weight that is less than about 600 kD (e.g., in the range from about 120 to about 400 kD). Suitable polyols include, but are not limited to, mannitol, trehalose, sorbitol, erythritol, isomalt, lactitol, maltitol, xylitol, glycerol, lactitol, propylene glycol, polyethylene glycol, inositol, or mixtures thereof. In embodiments, suitable sugars and carbohydrates include monosaccharides, disaccharides and polysaccharides or mixtures thereof. Suitable sugars (e.g., saccharides) or carbohydrates include, but are not limited to, fructose, glucose, mannose, sucrose, sorbose, xylose, lactose, maltose, sucrose, dextran, pullulan, dextrin, cyclodextrins, soluble starch, hydroxyethyl starch, water-soluble glucans, and mixtures thereof.

In embodiments, the formulation includes a polyol, a sugar, or a carbohydrate as described herein at a concentration ranging from between about 0.1% to about 20%, from about 1% to about 10%, from about 1% to about 8%, from about 1% to about 5%, from about 2% to about 10%, from about 2% to about 8%, from about 2% to about 5%, from about 3% to about 10%, from about 3 to about 8%, from about 3% to about 5%. In an embodiment, the formulation contains a polyol, a sugar, or a carbohydrate at a concentration of about 1%, about 2%, about 3%, about 4%, about 5%, about 6%, about 7%, about 8%, about 9%, or about 10%. In one embodiment, the formulation comprises concentration of polyol, which is between at least 10% less than and at least 10% greater than a concentration of a polyol disclosed herein. By way of example, in one embodiment the formulation comprises 4%+/−0.4% polyol. In one embodiment, the formulation further comprises 4%+/−0.8% sorbitol. In one embodiment, the formulation further comprises 4%+/−1.2% polyol.

In one embodiment, the formulation includes a tonicity agent, wherein the tonicity agent is selected from sorbitol or trehalose. In one embodiment, the formulation contains sorbital. In one embodiment, the concentration of sorbitol in the formulation is between about 1% to about 10%, between about 1% to about 5%, between about 2% to about 5%, or about 4%.

In certain embodiments, the tonicity agent is a salt. Without wishing to be bound by any theory, inclusion of salts, e.g., sodium chloride, may also improve antibody stability by protecting the protein from deamidation. Suitable salts include, but are not limited to, sodium chloride, sodium succinate, sodium sulfate, potassium chloride, magnesium chloride, magnesium sulfate, and calcium chloride.

In embodiments, the formulation includes a salt at a concentration ranging from about 1 mM to about 200 mM, from about 10 mM to about 150 mM, from about 20 mM to about 150 mM, from about 50 mM to about 150 mM, from about 100 mM to about 150 mM, from about 10 mM to about 100 mM, from about 10 mM to about 50 mM, from about 10 mM to about 40 mM, from about 10 mM to about 30 mM, from about 15 mM to about 50 mM, from about 15 mM to about 30 mM, or from about 15 mM to about 25 mM. In one embodiment, the formulation contains a salt at a concentration of about 10 mM, 15 mM, 20 mM, 25 mM, 50 mM, or 150 mM, e.g., 20 mM. In one embodiment, the formulation comprises concentration of salt, which is between at least 10% less than and at least 10% greater than a concentration of a salt disclosed herein. By way of example, in one embodiment the formulation comprises 20 mM+/−10% of salt. In one embodiment, the formulation further comprises 20 mM+/−20% salt. In one embodiment, the formulation further comprises 20 mM+/−30% salt.

In one embodiment, the formulation contains a salt, wherein the salt is sodium chloride. In one embodiment, the formulation comprises sodium chloride at a concentration of from about 10 mM to about 150 mM, from about 10 mM to about 50 mM, from about 10 mM to about 30 mM, from about 15 mM to about 25 mM, or about 10 mM to about 15 mM, about 20 mM, or about 25 mM.

In certain embodiments, the formulation includes two tonicity agents, e.g., a polyol (a sugar) and a salt. In one embodiment, the formulation includes sorbitol and sodium chloride.

In certain embodiments, the formulations provided herein are isotonic for the eye (e.g., having an osmolality of about 270-330 mOsm per kg). In some embodiments, the formulation has an osmolality of from about 250 to about 450 mOsm per kg, 300 to 400 mOsm per kg, 350 to 400 mOsm per kg, 200 to 375 mOsm per kg, or 350 to 375 mOsm per kg. In embodiments, the formulation has an osmolality of 270-330 mOsm per kg, e.g., about 320 mOsm per kg.

Other Excipients

The formulations featured in the invention may also contain other pharmaceutically acceptable excipients. See e.g., Gennaro (ed.), Remington: The Science and Practice of Pharmacy, 20th ed., Lippincott, Williams & Wilkins (2000) (ISBN: 0683306472); Ansel et al., Pharmaceutical Dosage Forms and Drug Delivery Systems, 7th Ed., Lippincott Williams & Wilkins Publishers (1999) (ISBN: 0683305727); Kibbe (ed.), Handbook of Pharmaceutical Excipients, 3rd ed. (2000) (ISBN: 091733096X); Protein Formulation and Delivery, McNally and Hastedt (eds.), Informa Health Care (ISBN: 0849379490) (2007). Among the excipients that can be added are chelating agents, amino acids, preservatives (e.g., preserving agents), penetration enhancers, bioadhesives, stabilizers, antioxidants, and viscosity agents.

The formulation can include one or more penetration enhancer and/or bioadhesive. Penetration enhancers and bioadhesives may include, for example, chitosan, cytochalasin B, aminated gelatin, poly-ε-caprolectone (carbopol 941P); poly(butylcyanoacrylate); poly-L-arginine; cyclodextrins; gellan; poly(acrylic acid); hyaluronic acid; mucin; alginate; a carbophil, and poloxamers (e.g., see Nagarwal et al., J Controlled Release, 136:2-13 (2009); Ding, PSTT 1:328-35 (1998); and Sahoo et al., Drug Discovery Today, 13:144-51(2008). Other excipients may be useful as stabilizers, and can include, for example, glycerin, potassium chloride, potassium phosphate, propylene glycol, sodium acetate, sodium bisulfite, sodium borate, sodium borate decahydrate, sodium chloride, sodium citrate, sodium phosphate, sodium phosphate (including sodium phosphate monobasic and dibasic); zinc chloride, phenol, benzoate, derivatives of castor oil and ethylene oxides, and Cremophor® (BASF Corp., Germany).

The formulation can include one or more chelating agents. Chelating agents can lower the formation of reduced oxygen species, reduce acidic species (e.g., deamidation) formation, reduce antibody aggregation, and/or reduce antibody fragmentation, and/or reduce antibody oxidation in the compositions of the present invention. Such chelating agents can reduce or prevent degradation of an antibody that is formulated in comparison to the antibody without the protection of a chelating agent.

Suitable chelating agent include, but are not limited to aminopolycarboxylic acids, hydroxyaminocarboxylic acids, N-substituted glycines, 2-(2-amino-2-oxocthyl) aminoethane sulfonic acid (BES), deferoxamine (DEF), citric acid, niacinamide, and desoxycholates and mixtures thereof. Further preferably the chelating agent is selected from the group consisting of ethylenediaminetetraacetic acid (EDTA), diethylenetriamine pentaacetic acid 5 (DTPA), nithlothacetic acid (NTA), N-2-acetamido-2-iminodiacetic acid (ADA), bis(aminoethyl)glycolether, N, N, 1ST, IST-tetraacetic acid (EGTA), trans-diaminocyclohexane tetraacetic acid (DCTA), glutamic acid, and aspartic acid, N-hydroxyethyliminodiacetic acid (HIMDA), N, N-bis-hydroxyethylglycine (bicine) and N-(thshydroxymethylmethyl) 10 glycine (tricine), glycylglycine, sodium desoxycholate, ethylenediamine; propylenediamine; diethylenetriamine; triethylenetetraamine (trien), ethylenediaminetetraaceto EDTA; disodium EDTA, calcium EDTA oxalic acid, malate, citric acid, citric acid monohydrate, and trisodium citratedihydrate, 8-hydroxyquinolate, amino acids, histidine, cysteine, methionine, peptides, polypeptides, and proteins and mixtures thereof. Further preferably the chelating agent is selected from the group consisting of salts of EDTA including dipotassium edetate, disodium edetate, edetate calcium disodium, sodium edetate, trisodium edetate, and potassium edetate; and a suitable salt of deferoxamine (DEF) is deferoxamine mesylate (DFM), or mixtures thereof. Chelating agents used in the invention can be present, where possible, as the free acid or free base form or salt form of the compound, also as an anhydrous, solvated or hydrated form of the compound or corresponding salt.

The formulation can include one or more amino acids. Suitable amino acids include, but are not limited to: arginine, glutamic acid, histidine, or methionine. The amino acid is typically selected to enhance the stability and/or the solubility of the protein. Methods of identifying such amino acids are known in the art. In some embodiments, a formulation contains arginine.

The formulation can include one or more viscosity agents. Viscosity agents are generally included in ophthalmic formulations to increase the residence time of an ophthalmic treatment that would otherwise be rapidly cleared by blinking and drainage through the conjunctival sac.

Suitable viscosity agents include, but are not limited to, methylcelluloses, including sodium carboxymethyl cellulose (also referred to herein as carboxymethyl cellulose or CMC); hydroxy celluloses, including ethyl cellulose; hydroxypropyl methylcellulose (hypromellose); carbomers, such as 934P, 971P and 974P; polyvinyl alcohol; xanthan gum; guar gum; gellan gum; and glycerin.

The formulation can include one or more antioxidants. Suitable antioxidants include, but are not limited to, methionine, sodium thiosulfate, catalase, and platinum.

The formulation can include one or more preservatives, e.g., to prevent microbial and fungal contamination during use, and/or one or more detergents, or surfactants, e.g., to solubilize proteins. Suitable preservatives include, but are not limited to: benzalkonium chloride, benzalthonium chloride, benzyl alcohol, chlorobutanol, benzododecinium bromide, methyl paraben, propyl paraben, phenylethyl alcohol, phenoxyethanol, phenol, m-cresol, edetate disodium, sorbic acid, and polyquaternium-1, and can be included at a concentration of from 0.001 w/v to 1.0% w/v. Typically, a formulation containing a therapeutic protein as described herein is sterile yet free of preservatives.

The formulation can also include other compounds that act as a lubricant or wetting agent. These include viscosity agents such as: monomeric polyols, such as, glycerol, propylene glycol, ethylene glycol; polymeric polyols, such as polyethylene glycol, various polymers of the cellulose family: hydroxypropylmethyl cellulose ("HPMC"), sodium carboxymethyl cellulose, hydroxy propylcellulose ("HPC"), dextrans, such as dextran 70; water soluble proteins, such as gelatin; and vinyl polymers, such as polyvinyl alcohol, polyvinylpyrrolidone, povidone and carbomers, such as carbomer 934P, carbomer 941; carbomer 940, carbomer 974P. Still additional examples include polysaccharides, such as hyaluronic acid and its salts and chondroitin sulfate and its salts, and acrylic acid polymers. In certain embodiments, the formulation has a viscosity between 1 cP to 400 cP.

pH

In another aspect, the formulations provided herein has a pH between about 5.0 to about 7.5, about 5.5 to about 7.5, about 6.0 to about 7.5, about 6.5 to about 7.5, about 5.0 to about 7.0, about 5.5 to about 7.0, about 6.0 to about 7.0, or about 6.2 to about 6.8. In an embodiment, the formulations provided herein have a pH of less than 7.5, less than 7.0, less than 6.9, less than 6.8, less than 6.6, less than 6.5, less than 6.4, less than 6.3, less than 6.2, or less than 6.0. In an embodiment, the formulation provided herein has a pH of about 6.5, or 6.5.

The pH levels of a composition or formulation described herein can be adjusted during the formulation process in any of the methods known in the art. In one embodiment, highly concentrated acid, e.g., hydrogen chloride (HCl) or highly concentrated base, e.g., sodium hydroxide (NaOH), is added until the desired pH is reached.

Stability

As is known in the art, proteins, e.g., antibodies, are more sensitive to agitation and temperature than small molecules. Agitation stress can lead to precipitation and heat stress can lead to precipitation and to chemical degradation. In addition, during loading of a compound into a delivery device, there can be exposure to heat stress. Applicants have achieved a formulation that successfully provides excellent stability when exposed to agitation stress and heat.

In embodiments, a formulation described herein is stable. In embodiments, the formulation exhibits stability under conditions (e.g., storage at particular temperatures, or agitation stress) described herein. In embodiments, stability is assessed using one or more methods described herein (e.g., based on visual appearance, content by spectrophotometry (A280), SDS-PAGE non-reduced, SDS-PAGE reduced; size exclusion HPLC (SE HPLC) or SE-UPLC; reverse phase HPLC (RP-HPLC); weak anion exchange HPLC (WAEX-HPLC); potency; a light obscuration particle count test (e.g., a light obscuration particle count test as described in USP <789>); or a microscopic particle count test (e.g., a microscopic particle count test as described in USP <789>)) and/or methods known in the art.

Stability can be assessed based on visual appearance. In embodiments, a formulation is stable if it is a clear to slightly opalescent colorless solution essentially free from visible particulates.

In embodiments, the formulation is stable at about 25° C. to about 40° C., for example, about 27° C., about 28° C., about 29° C., about 30° C., about 31° C., about 32° C., about 33° C., about 34° C., about 35° C., about 36° C., about 37° C., about 38° C., about 39° C., or about 40° C. for a period of at least two days; three days; five days; one week; ten days, two weeks, three weeks, four weeks, five weeks, six weeks, eight weeks, 16 weeks, 20 weeks, 25 weeks, 30 weeks, 35 weeks, 40 weeks, 45 weeks, one month, two months, three months, four months, five months, six months, seven months, eight months, or more.

In embodiments, the formulations are stable for long periods of time during storage at temperatures of from about 2° C. to about 8° C., such as at about 4° C., about 5° C., about 6° C., from 2° C. to 8° C., at 4° C., at 5° C., or at 6° C. For example, the formulations are stable at such storage temperatures for a period of at least two weeks; four weeks; six weeks; two months; three months; six months, one year, two years, three years, or four years.

Stability of a formulation can be assessed, e.g., after storage for at least 2, 4, 6, 8, 12, or 18 months, e.g., at 2-8° C., or after storage under ambient conditions, e.g., at room temperature (RT), e.g. at about 25° C. for, e.g., at least 2 weeks, 1 month, 2 months, 3 months 5 months, 6 months, 12 months, or 18 months. In embodiments, the formulation is stable after storage at 2-8° C. for at least 8 months. In embodiments, the formulation is stable after exposure to room temperature for at least 5 months. In some such embodiments, the formulation is stable after storage, e.g., for at least 5 months, in a BFS container.

Stability can be assessed, e.g., based on methods and criteria described herein or known in the art. For example, stability can be assessed based on physical purity (e.g., lack of aggregation, e.g., as assessed using size exclusion HPLC, also referred to herein as size exclusion, SE HPLC, or SEC HPLC), chemical purity (e.g., as assessed using weak anion exchange HPLC, reverse phase HPLC, and/or SDS PAGE (e.g., reduced or nonreduced SDS PAGE)), and/or the levels of particulates (e.g., as assessed visually or by particle count using an HIAC liquid particle counter (Beckman Coulter, Brea, CA)).

In embodiments, stability is demonstrated based on compliance with guidelines for particulate matter in ophthalmic solutions, e.g., as set forth in USP <789> (U.S. Pharmacopeia, Particulate Matter in Opthalmic Solutions).

In embodiments, the formulation has less than or equal to 50 particles per ml for particles ≥10 μm and/or less than or equal to 5 particles per ml for particles ≥25 μm, e.g., as assessed using a light obscuration particle count test (e.g., a light obscuration particle count test as described in USP <789>).

In embodiments, the formulation has less than or equal to 50 particles per ml for particles ≥10 μm, less than or equal to 5 particles per ml for particles ≥25 μm, and/or less than or equal to 2 particles per ml for particles ≥50 μm, e.g., as assessed using a microscopic particle count test (e.g., a microscopic particle count test as described in USP <789>).

In embodiments, stability is demonstrated based on compliance with guidelines for particulate matter in injections, e.g., as set forth in USP <789> (U.S. Pharmacopeia, Particulate Matter in Injections).

In embodiments, the formulation has less than or equal to 6000 particles per container (for containers with a volume of 100 ml or less) for particles ≥10 μm, and/or less than or equal to 600 particles per container (for containers with a volume of 100 ml or lower) for particles ≥25 urn, e.g., as assessed using a light obscuration particle count test (e.g., a light obscuration particle count test as described in USP <789>).

In embodiments, the formulation has less than or equal to 3000 particles per 5 ml for particles ≥10 μm and/or less than or equal to 300 particles per 5 ml for particles ≥25 μm, e.g., as assessed using a microscopic particle count test (e.g., a microscopic particle count test as described in USP <789>).

In embodiments, the protein in a formulation is protected from agitation stress as demonstrated, e.g., by lack of aggregation (lack of aggregation may be demonstrated, e.g., if the formulation contains contains >90%, >91%, >92%, >93%, >94%, >95%, >96%, >97%, >98%, or >99% of the monomeric form of the protein relative to aggregated form) after vortexing the protein solution, e.g., for 1-8 hours at room temperature (RT), e.g., for 4 hours at RT. Aggregation can be assessed, e.g., using methods described herein or methods known in the art. For example, aggregation can be assessed using ultracentrifugation, size-exclusion chromatography, gel electrophoresis, dynamic light scattering, and/or turbidity measurements.

In some aspects, stability is assayed by physical or chemical methods known in the art. For example, physical purity or lack of aggregation can be determined using size exclusion HPLC or other methods that determine the relative amount of monomeric polypeptide in a formulation. Typically, a formulation with acceptable stability contains >90% of the monomeric form of therapeutic protein (e.g., an IL-6a, e.g., an IL-6 antibody or fragment thereof described herein) relative to aggregated forms of the protein. In embodiments, the formulation contains >90% (e.g., >91%, >92%, >93%, >94%, >95%, >96%, >97%, >98%, or >99%) of the monomeric form of the therapeutic protein (e.g., an IL-6a, e.g., an IL-6 antibody or fragment thereof described herein), relative to aggregated forms of the protein.

Chemical purity can be determined, for example, using weak cation exchange HPLC or reverse phase HPLC. Typically, a formulation with acceptable stability contains >80% of the native molecule, relative to chemically modified forms of the molecule, e.g., as assessed using weak cation exchange HPLC. In embodiments, the formulation contains >80% (e.g., >85%, >87%, >90%, or >95%) of the native molecule, relative to chemically modified forms of the molecule (e.g., oxidized or acetylated forms).

Particulates may be identified visually. In embodiments, the formulation is one that is essentially free of particulates that can be identified visually.

Biologic treatments can be problematic to administer because they can have a relatively short shelf life or require special storage conditions that can create obstacles for storage, transport, and patient use as well as assuring a sufficient supply of the biologic. An advantage of certain formulations provided herein is that the formulations are surprisingly stable not only under conditions of refrigeration, but also at temperatures that are in accord with room temperature (e.g., 25° C.) and above (e.g., 40° C.). Accordingly, the cytokine protein or polypeptide formulations (e.g. heterologous cytokine protein or polypeptide formulations), e.g., formulations described herein are, in some embodiments, provided in a liquid form that is stable at RT (e.g., at 25° C.) for a period of at least three days, five days, one week, ten days, two weeks, three weeks, six weeks, eight weeks, 16 weeks, 20 weeks, 25 weeks, 30 weeks, 35 weeks, 40 weeks, 45 weeks, one month, two months, three months, four months, five months, six months, seven months, eight months, twelve months, or more. In embodiments, a month is determined on date to date basis, e.g., from the first of the month to the first of the second month.

In other aspects the formulations are stable at about 25° C. to about 40° C., for example, about 27° C., about 28° C., about 29° C., about 30° C., about 31° C., about 32° C., about 33° C., about 34° C., about 35° C., about 36° C., about 37° C., about 38° C., about 39° C., or about 40° C. for a period of at least two days; three days; five days; one week; ten days, two weeks, three weeks, four weeks, five weeks, six weeks, eight weeks, 16 weeks, 20 weeks, 25 weeks, 30 weeks, 35 weeks, 40 weeks, 45 weeks, one month, two months, three months, four months, five months, six months, seven months, eight months, or more.

Administration

Forms

Pharmaceutical compositions and formulations described herein be formulated in a variety of forms. These include, for example, liquid, semi-solid, and solid dosage forms, such as liquid solutions (e.g., injectable and infusible solutions), dispersions or suspensions, including nanoparticles and liposomes. The form will generally depend on the intended mode of administration and therapeutic application. Compositions for the agents described herein are typically in the form of injectable or infusible solutions, or are formulated for topical delivery, e.g., topical ocular delivery.

In some embodiments, a pharmaceutical composition described herein is sterile and stable under the conditions of manufacture and storage. A pharmaceutical composition can also be tested to ensure it meets regulatory and industry standards for administration. The composition can be formulated as a solution, microemulsion, dispersion, liposome, or other ordered structure suitable to high drug (e.g., a biologic) concentration. Sterile injectable solutions can be prepared by incorporating an agent described herein in the required amount in an appropriate solvent with one or a combination of ingredients enumerated above, as required, followed by filtered sterilization. Generally, dispersions are prepared by incorporating an agent described herein into a sterile vehicle that contains a basic dispersion medium and the required other ingredients from those enumerated above. In the case of sterile powders for the preparation of sterile injectable solutions, exemplary methods of preparation include vacuum drying and freeze-drying that yields a powder of an agent described herein plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be engineered by inclusion of an agent that delays absorption, for example, monostearate salts and gelatin. Such an agent may be particularly useful in a low-dose formulation. In embodiment, the formulation comprises ≤1 mg/ml of a therapeutic protein (e.g., a an IL-6a, e.g., an IL-6 antibody or fragment thereof described herein) and gelatin is included in the formulation.

In certain embodiments, a formulation is prepared with a carrier. In such embodiments, the formulation can be delivered, for example, as a controlled release formulation, delivered by an implant or a microencapsulated delivery system. Biodegradable, biocompatible polymers can be used, such as ethylene vinyl acetate, polyanhydrides, polyglycolic acid, collagen, polyorthoesters, and polylactic acid. See e.g., Sustained and Controlled Release Drug Delivery Systems, J. R. Robinson, ed., Marcel Dekker, Inc., New York, 1978.

Ophthalmic packs may be used to give prolonged contact of an ophthalmic formulation with the eye. A cotton pledget is saturated with the formulation and then inserted into the superior or inferior fornix. The formulation may also be administered by the way of iontophoresis. This procedure keeps the solution in contact with the cornea in an eyecup bearing an electrode. Diffusion of the drug is effected by difference of electrical potential. Iontophoretic systems which have been used include Ocuphor®1 (Iomed Inc., USA); Eyegate® II Delivery Systeml (EyeGate Pharma, USA); and Visulex®1 (Acient Inc., USA). See Amo and Urtti, Drug Discovery Today, 13:143 (2008).

Another strategy for sustained ocular delivery is the use of gelifying agents. These materials can be delivered in a liquid form, as an eye drop or intraocular injection. After instillation the polymer undergoes a phase change and forms a semi-solid or solid matrix that releases the drug over prolonged period. The phase transition can be induced by changes in the temperature, ion concentration, or pH.

For topical ocular use, the gel forming solutions, such as Timoptic®-XE1 (Merck and Co. Inc., USA), which contains Gelrite® (purified anionic heteropolysaccharide from gellan gum); Pilogel®1 (Alcon, Inc., Switzerland) eye drops contain poly(acrylic acid); and Azasite®1 (Insite Vision, USA) have been tested clinically. These materials enhance the drug retention relative to the conventional eye drops and lead to increased drug absorption into the eye and reduced dosing frequency. See Amo and Urtti, Drug Discovery Today, 13:135-143 (2008).

A formulation featured in the invention can be delivered by injection, e.g., intravitreal, periocular, or subconjunctival injection. The formulation can be injected underneath the conjunctiva facilitating passage through the sclera and into the eye by simple diffusion. The formulation can also be injected underneath the conjunctiva and the underlying Tenon's capsule in the more posterior portion of the eye to deliver the agent to the ciliary body, choroid, and retina. The formulation may also be administered by retrobulbar injection.

In general, a formulation described herein can be administered to a subject, by any suitable method, such as intravenous administration as a bolus or by continuous infusion over a period of time, by intramuscular, intramuscular, intraarterial, intrathecal, intracapsular, intraorbital, intracardiac, intradermal, intraperitoneal, intrasynovial, transtracheal, subcutaneous, subcuticular, intraarticular, subcapsular, subarachnoid, intraspinal, epidural injection, intrasternal injection and infusion. Other suitable modes of administration include topical (e.g., dermal or mucosal) or inhalation (e.g., intranasal or intrapulmonary) routes. For certain applications, the route of administration is one of: intravenous injection or infusion, subcutaneous injection, or intramuscular injection. For administration to the eye, in some embodiments, the mode of administration for a formulation featured is topical administration to the eye, e.g., in the form of drops. Examples of devices that may contain the formulation and/or be used for administration of the formulation include simple eye droppers, squeeze bottles with or without metering function, and blow/fill/seal (BFS) devices such as those manufactured by Catalent (Somerset, NJ), multiuse devices using, for example tip-seal technology, silver/oligodynamic technology, sterile filters, collapsing primary containers, and the like.

An additional consideration for a container is that it provide an acceptable shelf-life once it is filled, e.g., there is an acceptably low level of evaporation and/or the formulation meets release assay specifications, e.g., specifications as described herein. In embodiments, the container is suitable to provide a shelf-life of at least two years, e.g., at least 3 years, at least 4 years, or at least 5 years, e.g., at 5° C. In embodiments, the container is suitable to provide a shelf-life of at least 3 years at 5° C. In embodiments, the container is suitable to provide a shelf-life of at least 2 months, 3 months, 4 months, 5 months, 6 months, 8 months, 10 months, or 12 months at RT. In embodiments, the the container is suitable to provide a shelf-life of at least 5 months at RT. Various suitable container materials are known in the art, for example certain plastics, for example, low density polyethylene (LDPE), high density polyethylene (HDPE), or polypropylene.

The formulation can be prepared for single use application in a container or can be prepared for use in a multiuse container.

A formulation featured herein can be delivered intravitreally, e.g., to treat disorders that are associated with, for example, the posterior segment of the eye. Methods of intravitreal administration are known in the art and include, for example, intraocular injection, implantable devices.

In embodiments, the formulation is administered intravitreally using an implantable device. In embodiments, the formulation comprises a thermal stabilizer, e.g., sorbitol. In embodiments, the sorbitol is present at a concentration of ≥5% w/v.

Implantable devices can be, for example, nonbiodegradable devices such as polyvinyl alcohol-ethylene vinyl acetate polymers and polysulfone capillary fibers, biodegradable devices such as polylactic acid, polyglycolic acid, and polylactic-co-glycolic acid, polycaprolactones, and polyanhydrides. Devices can be delivered in forms such as nanoparticles, liposomes, or microspheres.

Dosing

A formulation featured in the invention can be administered as a fixed dose, as weight determined dose (e.g., mg/kg), or as an age determined dose. The formulations described herein can be administered, for example, four times a day; three times a day; twice a day; once every day; every other day; every third, fourth or fifth day; every week; every two weeks; every three weeks; every four weeks; every five weeks; monthly; every two months; every three months; every four months; every six months; or as needed (ad libitum).

A pharmaceutical composition can include a "therapeutically effective amount" of an agent described herein. A therapeutically effective amount of an agent can vary according to factors such as the disease state, age, sex, and weight of the individual, and the ability of the compound to elicit a desired response in the individual, e.g., amelioration of at least one disorder parameter (e.g., sign), or amelioration of at least one symptom of the disorder (and optionally the effect of any additional agents being administered). A therapeutically effective amount is also one in which any toxic or detrimental effects of the composition are outweighed by the therapeutically beneficial effects. In some embodiments, a "therapeutically effective amount" is determined in a population of individuals and the amount is effective in ameliorating at least one symptom or indication of a cytokine-related disorder, e.g., an IL-6-related disorder in at least 5%, 10%, 25%, 50%, 70%, 75%, 80%, 85%, 90%, 95%, or 100% of an affected population. A formulation is typically administered in a therapeutically effective amount. In some cases, a therapeutically effective formulation is a vehicle formulation. In some cases, a therapeutically effective formulation comprises a therapeutic protein.

Pharmaceutical compositions can be administered using medical devices as described herein and as known in the art, e.g., implants, infusion pumps, hypodermic needles, and needleless hypodermic injection devices. A device can include, e.g., one or more housings for storing pharmaceutical compositions, and can be configured to deliver unit doses of the IL-6a, e.g., IL-6 antibody or fragment thereof described herein, and optionally a second therapeutic agent. The doses can be fixed doses, i.e., physically discrete units suited as unitary dosages for the subjects to be treated; each unit can contain a predetermined quantity of an IL-6a, e.g., an IL-6 antibody or fragment thereof described herein, calculated to produce the desired therapeutic effect in association with a pharmaceutical carrier and optionally in association with another agent, e.g., such as those available as over the counter or prescribed products.

In some embodiments, to treat a disorder described herein such as an IL-6-related disorder, the formulation is administered to a subject having the disorder in an amount and for a time sufficient to induce a sustained improvement in at least one sign or symptom of the disorder. An improvement is considered "sustained" if the subject exhibits the improvement over a prolonged period, e.g., on at least two occasions separated by one to four weeks. The degree of improvement can be determined based on signs or symptoms, and can also employ questionnaires that are administered to the subject, such as quality-of-life questionnaires.

Improvement can be induced by repeatedly administering a dose of the formulation until the subject manifests an improvement over baseline for selected signs and/or symptoms. In treating chronic conditions, the amount of improvement can be evaluated by repeated administration over a period of at least a month or more, e.g., for one, two, or three months or longer, or indefinitely. In treating an acute condition, the agent can be administered for a period of one to six weeks or even as a single dose.

Although the extent of the disorder after an initial or intermittent treatment can appear improved according to one or more signs or symptoms, treatment can be continued indefinitely at the same level or at a reduced dose or frequency. Treatment can also be discontinued, e.g., upon improvement or disappearance of signs or symptoms. Once treatment has been reduced or discontinued, it may be resumed if symptoms should reappear.

Treatment

Diseases that can be treated with an IL-6a of the invention include those diseases in which IL-6 expression, e.g., elevated IL-6 expression, is associated with the disease state or as a prerequisite to the disease state. Such diseases include those in which angiogenesis and inflammation driven by IL-6 contribute to disease pathology. This includes diseases in which IL-6 is elevated compared to normal levels, e.g., diseases in which IL-6 is elevated in the vitreous (such as, e.g., diabetic macular edema, diabetic retinopathy, and uveitis) or tissues of the eye. As described in WO2014/074905, incorporated herein by reference in its entirety, it has been previously shown that blocking the IL-6 pathway by administration of an IL-6 antibody in mouse and rat choroidal neovascularization models, which reproduce the pathologic processes underlying many IL-6 related diseases, e.g., DME, results in reduction of neovascularization to similar levels as an anti-VEGF positive control. These in vivo results demonstrate that local inhibition of IL-6 can be useful for treating ocular diseases associated with IL-6 expression and ocular diseases involving vascular leakage, e.g., macular edema.

Examples of IL-6 related diseases include certain eye diseases including, without limitation, dry eye (e.g., dry eye disease or dry eye syndrome), allergic conjunctivitis, uveitis, age-related macular degeneration (AMD) (wet (exudative) AMD or dry (atrophic) AMD), proliferative diabetic retinopathy (PDR), diabetic macular edema (DME), Rhegmatogenous retinal detachment (RRD), retinal vein occlusion (RVO), neuromyelitis optica (NMO), or myopic choroidal neovascularization. Other ocular disorders that can be treated include those caused by trauma such as corneal transplant, corneal abrasion, or other such physical injury to the eye. Other ocular disorders that can be treated include ocular cancers, e.g., cancers that affect the eye and the vicinity of the eye, e.g., the eye socket or the eyelids. Accordingly, the invention includes treating a subject having an IL-6 related disease with an IL-6a described herein.

As used herein, the term "treat" refers to the administration of an agent described herein to a subject, e.g., a patient, in an amount, manner, and/or mode effective to improve a condition, symptom, or parameter associated with a disorder, e.g., a disorder described herein, or to prevent the onset or progression of a disorder, to either a statistically significant degree or to a degree detectable to one skilled in the art. The treatment can be to cure, heal, alleviate, relieve, alter, remedy, ameliorate, palliate, improve or affect the disorder, the symptoms of the disorder or the predisposition toward the disorder. An effective amount, manner, or mode can vary depending on the subject and may be tailored to the subject. Exemplary subjects include humans, primates, and other non-human mammals. A formulation featured in the invention can also be given prophylactically to reduce the risk of the occurrence of a disorder or symptom or sign thereof.

In some embodiments, the IL-6 related disease is an inflammatory disease. In some embodiments, the disease is glaucoma.

In some embodiments, the disease is ocular pain, e.g., pain associated with an ocular disease or disorder.

In some embodiments, treatment of a subject also includes determining whether the subject has an IL-6 associated disease, and optionally, whether the subject is resistant to other non-IL-6 inhibitory treatments such as steroids or anti-VEGF agents.

The formulations described herein can be administered to a subject having or at risk for such IL-6 related diseases. The IL-6 related disease or disorder can be an inflammatory disorder such as described below. The formulations described herein can be administered to a subject having or at risk for such IL-6 mediated inflammatory disorders.

The formulations featured in the invention are particularly suited for use in ocular disorders, e.g. ocular disorders in which it is desired to administer the IL-6 antagonist, e.g., IL-6 antibody or fragment thereof described herein, directly to the eye, or locally to the area of the eye.

Subjects having a dry eye disorder can exhibit inflammation of the eye, and can experience scratchy, stingy, itchy, burning or pressured sensations, irritation, pain, and redness. Dry eye disorders can be associated with excessive eye watering and insufficient tear production. A formulation featured in the invention can be administered to such a subject to ameliorate or prevent the onset or worsening of one or more such symptoms. A formulation featured in the invention can also be used to mitigate pain, e.g., ocular pain, such as pain due to neuroinflammation, in a subject.

The embodiments described herein include methods of treating animals having IL-6-related disorders, for example, dry eye disorders. Dry eye can be a serious disorder in, for example canines. Non-limiting examples of disorders in dogs associated with dry eye include congenital disorders, infections (e.g., canine distemper virus), drug induction (e.g., by sulfa antibiotics), and removal of the tear gland of the third eyelid ("cherry eye"). Dry eye disorders are also commonly seen in certain dog breeds, for example, Cocker Spaniel, Shih Tzu, Lhasa Apso, Bulldog, Schnauzer, and West Highland White Terrier. Other non-limiting examples of animals that can be treated include cats and horses.

The formulations of the present invention can be administered to a subject having an allergic reaction affecting the eye, e.g., a subject experiencing severe allergic (atopic) eye disease such as, e.g., allergic conjunctivitis. For example, the formulation can be administered topically. See also, e.g., Keane-Myers et al. (1999) Invest Ophthalmol Vis Sci, 40(12): 3041-6.

The formulations featured in the invention can be administered to a subject who has or is at risk for diabetic retinopathy. See, e.g., Demircan et al. (2006) Eye 20:1366-1369 and Doganay et al. (2006) Eye, 16:163-170

Uveitis. Uveitis includes acute and chronic forms and includes inflammation of one or more of the iris, the ciliary body, and the choroid. Chronic forms may be associated with systemic autoimmune disease, e.g., Behçet's syndrome, ankylosing spondylitis, juvenile rheumatoid arthritis, Reiter's syndrome, and inflammatory bowel disease. In anterior uveitis, inflammation is primarily in the iris (also iritis). Anterior uveitis can affect subjects who have systemic autoimmune disease, but also subjects who do not have systemic autoimmune disease. Intermediate uveitis involves inflammation of the anterior vitreous, peripheral retina, and ciliary body, often with little anterior or chorioretinal inflammation. Pan planitis results from inflammation of the pars plana between the iris and the choroid. Posterior uveitis involves the uveal tract and primarily the choroid, and is also referred to as choroiditis. Posterior uveitis can be associated with a systemic infection or an autoimmune disease. It can persist for months and even years. The formulations featured in the invention can be administered to a subject to treat any of the foregoing forms of uveitis. See also e.g., Tsai et al. (2009) Mol Vis 15:1542-1552 and Trittibach et al. (2008) Gene Ther. 15(22): 1478-88.

In some embodiments, the formulations featured in the invention are used to treat a subject having or at risk for age-related macular degeneration (AMID), e.g., wet (exudative) AMD or dry (atrophic) AMD. The formulations can be applied topically to the eye, injected (e.g., intravitreally) or provided systemically. See, e.g., Olson et al. (2009) Ocul Immunol Inflamm 17(3):195-200.

Diabetic macular edema (DME). Diabetic macular edema (DME) involves occlusion and leakage of retinal blood vessels, causing reduced visual acuity and potentially blindness. Standard treatments for DME include local administration of steroids or anti-VEGF antibodies. However, many patients are refractory to these therapies. The pathogenesis of diabetic macular edema involves components of angiogenesis, inflammation, and oxidative stress. IL-6 is induced by hypoxia and hyperglycemia and can increase vascular inflammation, vascular permeability, and pathologic angiogenesis. IL-6 can directly induce VEGF expression and can promote choroidal neovascularization in animal models. In DME patients, ocular IL-6 levels are positively correlated with macular thickness and disease severity. IL-6 levels are reportedly elevated in patients who fail anti-VEGF therapy while decreasing in anti-VEGF responsive patients. Accordingly, administration of an IL-6a as described herein is useful for treatment of diabetics in combination with an anti-VEGF therapeutic or as an alternative to anti-VEGF treatment, including for patients who do not respond to anti-VEGF therapy. Treatment of macular edema with an IL-6a may also improve safety by removing the need to completely inhibit either mechanism to inhibit the pathology, thus preserving some of the desired, physiological roles of each cytokine. Accordingly, local IL-6a treatment in combination with VEGF inhibition can decrease the dose frequency and reduce adverse effects of treatment.

In DME there are positive correlations between vitreal IL-6 levels and both disease severity and VEGF refractory subjects. Accordingly, an IL-6a as described herein can be used to treat DME subjects who are refractive to steroid therapy, anti-VEGF therapy, or both. Subjects that are refractive to a given therapy, e.g., steroid therapy or anti-VEGF therapy, or both, do not exhibit an improvement, reduction, or amelioration of a selected symptom. In some cases, an IL-6a, e.g., an IL-6 antibody or fragment thereof as described herein, is used in combination with anti-VEGF therapy or steroid therapy, e.g., to treat DME. Accordingly, in an embodiment, the formulations provided herein comprise an anti-VEGF agent or a steroid.

A formulation described herein can be administered by any mode to treat an ocular disease. The agent can be delivered by a parenteral mode. Alternatively or in addition, the formulation can be delivered directly to the eye or in the vicinity of the eye. For example, the formulation can be administered topically, intraocularly, intravitreally, e.g., by intravitreal injection, or subconjuntivally.

The formulations described herein, e.g., comprising an IL-6 antibody or fragment thereof as described herein, can also be used to treat disorders such as cancer, e.g., an ocular cancer (a cancer in the eye or in the vicinity of the eye), prostate cancer, leukemia, multiple myeloma, inflammatory (such as chronic inflammatory proliferative diseases) and autoimmune disease, e.g., rheumatoid arthritis, Castleman's disease (giant or angiofollicular lymph node hyperplasia, lymphoid hamartoma, angiofollicular lymph node hyperplasia), juvenile idiopathic arthritis (including polyarticular juvenile idiopathic arthritis and systemic juvenile idiopathic arthritis), Still's disease (encompassing juvenile idiopathic arthritis and adult onset Still's disease), adult onset Still's disease, amyloid A amyloidosis, polymyalgia rheumatica, remitting seronegative symmetrical synovitis with pitting edema, spondyloarthritides, Behçet's disease (including treatment of ocular manifestations), atherosclerosis, psoriasis, systemic lupus erythematosis, polymyositis (an inflammatory myopathy), relapsing polychondritis, acquired hemophilia A, multiple sclerosis, anemia of inflammation, and Crohn's disease.

IL-6 antagonists are also useful for treatment of certain neurologic diseases. Accordingly, in some cases, the formulations described herein can be used for treating depression and Alzheimer's disease.

Other diseases that can be treated with a formulation as described herein include, without limitation, systemic sclerosis, Takayasu arteritis, giant cell arteritis, graft versus host disease, and TNF-receptor-associated periodic syndrome (TRAPS).

Equivalents

All technical features can be individually combined in all possible combinations of such features.

The invention may be embodied in other specific forms without departing from the spirit or essential characteristics thereof. The foregoing embodiments are therefore to be considered in all respects illustrative rather than limiting on the invention described herein.

The entire content of all references cited herein is hereby incorporated in its entirety.

The following non-limiting examples further illustrate embodiments of the inventions described herein.

EXAMPLES

Example 1: Formulation Study by kD

An initial screen was performed to identify promising excipients and formulations for an IL-6 antibody, EBI-031, by assessing the kD of the antibody in each formulation. Diffusion interaction parameter, kD, was determined using a Wyatt DyanPro plate reader, which measures the diffusion coefficient of nano-particles in free solution. Concentrated EBI-031 was serially diluted in formulation buffer to achieve the desired concentration. The diffusion coefficient for EBI-031 monomer was measured using multiple replicates. The average diffusion coefficient was plotted versus EBI-031 concentration. Diffusion coefficient, kD, was obtained by dividing the slope of the graph by the y-value.

The tested formulations contained 20 mM of a buffer selected from citrate, histidine, or phosphate, and one of the following: 5% sucrose, 5% trehalose, 5% sorbitol, or 150 mM NaCl. The tested formulations containing citrate buffer had a pH of 6.0 or 6.5, and the formulations containing histidine or phosphate buffer had a pH of 6.0, 6.5, or 7.0. Table 2 shown below summarizes the results from the kD formulation screen.

Based on the results from this screen, the solubility was good at pH 6.5, but not as good at pH 6.0 or pH 7.0, suggesting that the best pH is at 6.5. A summary of the results are shown in Table 2. This screen also showed that a salt, such as sodium chloride, was good for all formulations.

TABLE 2

Summary of kD fomulation screen

| Buffer | pH | Excipient | Form# | Line equation | kD |
|--------|-----|-----------|-------|---------------|-----|
| citrate | 6 | NaCl | 1 | $-6E-09x + 4E-07$ | $-0.015$ |
|  |  | Sucrose | 2 | $-1E-08x + 4E-07$ | $-0.025$ |
|  |  | Trehalose | 3 | $-2E-09x + 3E-07$ | $-0.00667$ |
|  |  | Sorbitol | 4 | $-4E-09x + 3E-07$ | $-0.01333$ |
| citrate | 6.5 | NaCl | 5 | $-2E-09x + 4E-07$ | $-0.005$ |
|  |  | Sucrose | 6 | $-4E-09x + 4E-07$ | $-0.01$ |
|  |  | Trehalose | 7 | $-1E-09x + 3E-07$ | $-0.00333$ |
|  |  | Sorbitol | 8 | $-1E-09x + 3E-07$ | $-0.0033$ |
| his | 6 | NaCl | 9 | $-5E-09x + 4E-07$ | $-0.0125$ |
|  |  | Sucrose | 10 | $-8E-09x + 4E-07$ | $-0.02$ |
|  |  | Trehalose | 11 | $-8E-09x + 4E-07$ | $-0.02$ |
|  |  | Sorbitol | 12 | $-1E-08x + 4E-07$ | $-0.025$ |
| His | 6.5 | NaCl | 13 | $-4E-09x + 4E-07$ | $-0.01$ |
|  |  | Sucrose | 14 | $-4E-09x + 4E-07$ | $-0.01$ |
|  |  | Trehalose | 15 | $-5E-09x + 4E-07$ | $-0.0125$ |
|  |  | Sorbitol | 16 | $-5E-09x + 4E-07$ | $-0.0125$ |
| His | 7 | NaCl | 17 | $-6E-09x + 5E-07$ | $-0.012$ |
|  |  | Sucrose | 18 | $-9E-09x + 4E-07$ | $-0.0225$ |
|  |  | Trehalose | 19 | $-5E-09x + 4E-07$ | $-0.0125$ |
|  |  | Sorbitol | 20 | $-3E-09x + 4E-07$ | $-0.0075$ |
| Pi | 6 | NaCl | 21 | $-1E-08x + 5E-07$ | $-0.02$ |
|  |  | Sucrose | 22 | $-2E-09x + 3E-07$ | $-0.00667$ |
|  |  | Trehalose | 23 | $-1E-08x + 4E-07$ | $-0.025$ |
|  |  | Sorbitol | 24 | $-7E-09x + 4E-07$ | $-0.0175$ |
| Pi | 6.5 | NaCl | 25 | $-3E-09x + 4E-07$ | $-0.0075$ |
|  |  | Sucrose | 26 | $-1E-09x + 3E-07$ | $-0.00333$ |
|  |  | Trehalose | 27 | $-2E-09x + 3E-07$ | $-0.00667$ |
|  |  | Sorbitol | 28 | $-1E-09x + 3E-07$ | $-0.00333$ |
| Pi | 7 | NaCl | 29 | $-5E-09x + 4E-07$ | $-0.0125$ |
|  |  | Sucrose | 30 | $-9E-09x + 4E-07$ | $-0.0225$ |
|  |  | Trehalose | 31 | $-1E-09x + 3E-07$ | $-0.00333$ |
|  |  | Sorbitol | 32 | $-7E-10x + 3E-07$ | $-0.00233$ |

Example 2: Dynamic Light Scattering (DLS) Screen of Different Buffers and Excipients An accelerated stability study was performed to screen different buffers and excipients for EBI-031. The formulations tested contained EBI-031 at 1 mg/ml, 20 mM of a buffer, and a tested excipient (such as a tonicity agent or an amino acid). The buffers used were selected from: Tris buffer at pH 7.5, phosphate buffer at pH 6.5 or pH 7.5, histidine buffer at pH 6.5, citrate buffer at pH 5.5, or acetate buffer at pH 5.5. The tested excipients were selected from: 5% sorbitol, 10% sucrose, 5% trehalose, 5% xylitol, 150 mM sodium chloride, 0.2M arginine, or 0.2M glycine. The particular formulations tested are shown in the Table 3 below. The samples were incubated at 38° C. and stability was assessed after 1 and 6 weeks.

Dynamic light scattering (DLS) is utilized as a measurement of aggregate formation by protein molecules in solution. The samples are placed in a Wyatt miniDAWN TREOS where the instrument measures the diffusion coefficient (Dt) based on brownian motion. The hydrodynamic radius (Rh) is inversely proportional to the diffusion coefficient and an increased hydrodynamic radius indicates aggregation. The results for the DLS screen are summarized in Table 3 below.

TABLE 3

Accelerated Stability Study for EBI-031 by DLS.
Measurement of Rh for Stressed EBI-031 at 1 mg/mL

| | | Weeks at 38° C. | | |
|---|---|---|---|---|
| | | 0 | 1 | 6 |
| Tris pH 7.5 | Sorbitol | 7 | 5.7 | 5.6 |
| | Xylitol | 6.6 | 5.7 | 5.6 |
| | Arginine | 5.6 | 5.4 | 6.5 |
| Phosphate pH 7.5 | Arginine | 5.3 | 5.5 | 5.2 |
| | Glycine | 6.8 | 5.6 | 5.6 |
| | NaCl | 6.3 | 5.6 | 5.6 |
| Phosphate pH 6.5 | NaCl | 6.1 | 5.6 | 5.6 |
| | Arginine/NaCl | 6 | 5.5 | 5.4 |
| Histidine pH 6.5 | Glycine | 6.3 | 5.5 | 6 |
| | NaCl | 7 | 6.1 | 235.3 |
| | Arginine/NaCl | 5.6 | 5.4 | 163.3 |
| | Gly/NaCl | 6.3 | 5.9 | 5.8 |
| Citrate pH 5.5 | Sucrose | 8.3 | 7.6 | 7.1 |
| | Tehalose | 6.7 | 5.6 | 5.6 |
| | Sorbitol | 6.6 | 5.9 | 19.2 |
| | Xylitol | 6.9 | 6.2 | 73.2 |
| | Arginine | 4.9 | 4.7 | 4.7 |
| | Glycine | 6.2 | 5.7 | 8.9 |
| Acetate pH 5.5 | Sorbitol | 5.8 | 5.6 | 5.6 |
| | Xylitol | 6.2 | 5.5 | 42.2 |
| | Arginine | 5.5 | 5.5 | 19.6 |
| | Glycine | 6.2 | 5.7 | 9.3 |

Example 3: Product Purity Formulation Study at 0 and 7 Days

Various excipients were tested in different formulations containing the EBI-031 antibody. The different formulations were tested for at day 0 and day 7 for sample recovery, product purity, and appearance. The tested formulations contained 20 mM of a base buffer, where the buffer was acetate (pH 5.5), citrate (pH 6.0 or pH 6.5), histidine (pH 6.5), phosphate (pH 6.5, pH 7.0, or pH 7.5), and tricine (pH 8.5); sodium chloride at either 20 mM and 150 mM; and one of the following excipients: 10% sucrose, 5% sorbitol, 0.1% polysorbate-20, 0.1% polysorbate-80, 0.1% poloxamer P188, and 0.2M arginine.

Tested formulations were prepared in a 96 well microdialysis plate. Microdialysis plate wells were filled with stock buffer (20 mM of buffer) and excipient solutions at 2× final concentration (e.g., 900 µl 2× Buffer+900 µL 2× excipient solution). The plate was mixed on a plate shaker to ensure mixing prior to sample addition. Protein samples were added to the appropriate wells. The organization of the formulations on the plate is shown in Table 4. Samples were dialyzed on a plate shaker at room temperature for 2 hours. Sample well inserts were transferred to a second buffer/excipient plate for overnight dialysis in fresh solutions.

Following overnight dialysis, each sample was recovered and transferred into clear 300 µL glass vials. All samples were clear and colorless. The volumes recovered from each dialysis cassette varied in certain buffer conditions (particularly in the 10% sucrose buffers).

The concentration of each sample was then analyzed using a NANODROP® Spectrophotomer (Thermo Scientific); however the measurements were variable, possibly due to high viscosity/high protein concentration. An aliquot of each sample was then diluted to 100-fold in size exclusion-UPLC (SE-UPLC) mobile phase buffer to approximately 0.994 mg/mL (based on starting concentration) and analyzed on the NANODROP® Spectrophotomer. Results of the recovery are shown in Table 4.

TABLE 4

| | | 20 mM Sodium Chloride | | | | | | 150 mM Sodium Chloride | | | | | |
|---|---|---|---|---|---|---|---|---|---|---|---|---|---|
| | | 1 - 10% Sucrose | | | | | | 7 - 10% Sucrose | | | | | |
| | | 2 - 5% Sorbitol | | | | | | 8 - 5% Sorbitol | | | | | |
| | | 3 - 0.1% Polysorbate-20 | | | | | | 9 - 0.1% Polysorbate-20 | | | | | |
| | | 4 - 0.1% Polysorbate-80 | | | | | | 10 - 0.1% Polysorbate-80 | | | | | |
| | | 5 - 0.1% Poloxamer P188 | | | | | | 11 - 0.1% Poloxamer P188 | | | | | |
| | | 6 - 0.2M Arginine | | | | | | 12 - 0.2M Arginine | | | | | |
| Day 0 | | 1 | 2 | 3 | 4 | 5 | 6 | 7 | 8 | 9 | 10 | 11 | 12 |
| Acetate pH 5.5 | A | 0.97 | 1.49 | 1.04 | 0.98 | 0.98 | 1.08 | X | 1.05 | 1.08 | 1.10 | 1.01 | 1.10 |
| Citrate pH 6.0 | B | 1.40 | 1.20 | 1.13 | 1.06 | 1.19 | 0.46 | 1.38 | 1.34 | 1.10 | 1.06 | 0.99 | 1.10 |
| Citrate pH 6.5 | C | 1.32 | 1.09 | 1.03 | 1.06 | 1.03 | 1.18 | 1.29 | 1.15 | 1.07 | 0.98 | 1.06 | 1.05 |
| Histidine pH 6.5 | D | 1.40 | 1.09 | 0.95 | 0.98 | 1.01 | 0.97 | 1.48 | 1.06 | 1.11 | 0.97 | 0.98 | 1.01 |
| Phosphate pH 6.5 | E | 1.44 | 1.11 | 1.06 | 0.93 | 1.00 | 1.05 | 1.25 | 1.04 | 1.04 | 0.96 | 0.99 | 1.07 |
| Phosphate pH 7.0 | F | 1.39 | 0.99 | 1.07 | 0.25 | 0.97 | 1.02 | 1.46 | 1.04 | 1.19 | 0.94 | 0.99 | 1.04 |
| Phosphate pH 7.5 | G | 1.55 | 1.02 | 1.08 | 0.90 | 1.01 | 1.05 | 1.29 | 1.14 | 1.10 | 1.03 | 1.02 | 1.04 |
| Tricine pH 8.5 | H | 0.58 | 1.05 | 0.97 | 0.99 | 0.95 | 1.04 | 1.31 | 0.93 | 0.99 | 1.02 | 1.02 | 1.02 |

An increased protein concentration was observed in all conditions containing 10% sucrose, most likely due to the reduction in recovery volume. There were no substantial differences between the samples by analysis by chromatogram overlay of the chromatograms obtained by SE-UPLC. Comparison of the protein concentration determined using the NANODROP® Spectrophotomer and as predicted from SE-UPLC peak area was in good accordance as shown in Table 5.

TABLE 5

Concentration determinations are compatible between NANODROP ® and SE-UPLC predictions

| Base Buffer | Salt Level | Excipient | Code | NANODROP ® (mg/ml) | Conc (mg/mL) (Based on Reference Standard) | Conc (mg/mL) (Based on A280 Conversion) |
|---|---|---|---|---|---|---|
| | | Start Material | | 0.96 | 1.06 | 1.02 |
| Acetate pH 5.5 | 20 mM Sodium Chloride | 10% Sucrose | 1A | 0.97 | 0.97 | 0.94 |
| | | 5% Sorbitol | 2A | 1.49 | 1.50 | 1.45 |
| | | 0.1% Polysorbate-20 | 3A | 1.04 | 1.04 | 1.01 |
| | | 0.1% Polysorbate-80 | 4A | 0.98 | 0.99 | 0.95 |
| | | 0.1% Poloxamer P188 | 5A | 0.98 | 0.96 | 0.93 |
| | | 0.2M Arginine | 6A | 1.08 | 1.08 | 1.04 |
| | 150 mM Sodium Chloride | 10% Sucrose | 7A | | | |
| | | 5% Sorbitol | 8A | 1.05 | 1.05 | 1.02 |
| | | 0.1% Polysorbate-20 | 9A | 1.08 | 1.07 | 1.04 |
| | | 0.1% Polysorbate-80 | 10A | 1.10 | 1.10 | 1.07 |
| | | 0.1% Poloxamer P188 | 11A | 1.01 | 1.01 | 0.97 |
| | | 0.2M Arginine | 12A | 1.10 | 1.10 | 1.07 |
| Citrate pH 6.0 | 20 mM Sodium Chloride | 10% Sucrose | 1B | 1.40 | 1.36 | 1.32 |
| | | 5% Sorbitol | 2B | 1.20 | 1.19 | 1.15 |
| | | 0.1% Polysorbate-20 | 3B | 1.13 | 1.11 | 1.07 |
| | | 0.1% Polysorbate-80 | 4B | 1.06 | 1.06 | 1.03 |
| | | 0.1% Poloxamer P188 | 5B | 1.19 | 1.20 | 1.16 |
| | | 0.2M Arginine | 6B | 0.46 | 0.45 | 0.44 |
| | 150 mM Sodium Chloride | 10% Sucrose | 7B | 1.38 | 1.38 | 1.34 |
| | | 5% Sorbitol | 8B | 1.34 | 1.33 | 1.29 |
| | | 0.1% Polysorbate-20 | 9B | 1.10 | 1.07 | 1.04 |
| | | 0.1% Polysorbate-80 | 10B | 1.06 | 1.08 | 1.04 |
| | | 0.1% Poloxamer P188 | 11B | 0.99 | 1.01 | 0.98 |
| | | 0.2M Arginine | 12B | 1.10 | 1.08 | 1.05 |
| Citrate pH 6.5 | 20 mM Sodium Chloride | 10% Sucrose | 1C | 1.32 | 1.31 | 1.26 |
| | | 5% Sorbitol | 2C | 1.09 | 1.08 | 1.05 |
| | | 0.1% Polysorbate-20 | 3C | 1.03 | 1.03 | 1.00 |
| | | 0.1% Polysorbate-80 | 4C | 1.06 | 1.07 | 1.03 |
| | | 0.1% Poloxamer P188 | 5C | 1.03 | 1.03 | 0.99 |
| | | 0.2M Arginine | 6C | 1.18 | 1.19 | 1.15 |
| | 150 mM Sodium Chloride | 10% Sucrose | 7C | 1.29 | 1.28 | 1.24 |
| | | 5% Sorbitol | 8C | 1.15 | 1.15 | 1.11 |
| | | 0.1% Polysorbate-20 | 9C | 1.07 | 1.08 | 1.04 |
| | | 0.1% Polysorbate-80 | 10C | 0.98 | 0.99 | 0.95 |
| | | 0.1% Poloxamer P188 | 11C | 1.06 | 1.06 | 1.02 |
| | | 0.2M Arginine | 12C | 1.05 | 1.06 | 1.03 |

TABLE 5-continued

Concentration determinations are compatible between NANODROP ® and SE-UPLC predictions

| Base Buffer | Salt Level | Excipient | Code | NANODROP ® (mg/ml) | Conc (mg/mL) (Based on Reference Standard) | Conc (mg/mL) (Based on A280 Conversion) |
|---|---|---|---|---|---|---|
| Histidine pH 6.5 | 20 mM Sodium Chloride | 10% Sucrose | 1D | 1.40 | 1.40 | 1.36 |
| | | 5% Sorbitol | 2D | 1.09 | 1.07 | 1.04 |
| | | 0.1% Polysorbate-20 | 3D | 0.95 | 0.94 | 0.91 |
| | | 0.1% Polysorbate-80 | 4D | 0.98 | 0.98 | 0.95 |
| | | 0.1% Poloxamer P188 | 5D | 1.01 | 1.00 | 0.97 |
| | | 0.2M Arginine | 6D | 0.97 | 0.98 | 0.95 |
| | 150 mM Sodium Chloride | 10% Sucrose | 7D | 1.48 | 1.47 | 1.42 |
| | | 5% Sorbitol | 8D | 1.06 | 1.04 | 1.01 |
| | | 0.1% Polysorbate-20 | 9D | 1.11 | 1.11 | 1.07 |
| | | 0.1% Polysorbate-80 | 10D | 0.97 | 0.98 | 0.95 |
| | | 0.1% Poloxamer P188 | 11D | 0.98 | 0.97 | 0.94 |
| | | 0.2M Arginine | 12D | 1.01 | 1.01 | 0.98 |
| Phosphate pH 6.5 | 20 mM Sodium Chloride | 10% Sucrose | 1E | 1.44 | 1.47 | 1.42 |
| | | 5% Sorbitol | 2E | 1.11 | 1.12 | 1.09 |
| | | 0.1% Polysorbate-20 | 3E | 1.06 | 1.07 | 1.03 |
| | | 0.1% Polysorbate-80 | 4E | 0.93 | 0.95 | 0.92 |
| | | 0.1% Poloxamer P188 | 5E | 1.00 | 0.99 | 0.96 |
| | | 0.2M Arginine | 6E | 1.05 | 1.04 | 1.01 |
| | 150 mM Sodium Chloride | 10% Sucrose | 7E | 1.25 | 1.26 | 1.22 |
| | | 5% Sorbitol | 8E | 1.04 | 1.05 | 1.02 |
| | | 0.1% Polysorbate-20 | 9E | 1.04 | 1.06 | 1.03 |
| | | 0.1% Polysorbate-80 | 10E | 0.96 | 0.97 | 0.93 |
| | | 0.1% Poloxamer P188 | 11E | 0.99 | 1.00 | 0.96 |
| | | 0.2M Arginine | 12E | 1.07 | 1.08 | 1.04 |
| Phosphate pH 6.5 | 20 mM Sodium Chloride | 10% Sucrose | 1F | 1.39 | 1.39 | 1.34 |
| | | 5% Sorbitol | 2F | 0.99 | 0.99 | 0.96 |
| | | 0.1% Polysorbate-20 | 3F | 1.07 | 1.09 | 1.05 |
| | | 0.1% Polysorbate-80 | 4F | 0.25 | 0.27 | 0.26 |
| | | 0.1% Poloxamer P188 | 5F | 0.97 | 0.98 | 0.95 |
| | | 0.2M Arginine | 6F | 1.02 | 1.01 | 0.98 |
| | 150 mM Sodium Chloride | 10% Sucrose | 7F | 1.46 | 1.46 | 1.41 |
| | | 5% Sorbitol | 8F | 1.04 | 1.03 | 1.00 |
| | | 0.1% Polysorbate-20 | 9F | 1.19 | 1.19 | 1.15 |
| | | 0.1% Polysorbate-80 | 10F | 0.94 | 0.96 | 0.93 |
| | | 0.1% Poloxamer P188 | 11F | 0.99 | 0.99 | 0.96 |
| | | 0.2M Arginine | 12F | 1.04 | 1.04 | 1.00 |
| Phosphate pH 7.5 | 20 mM Sodium Chloride | 10% Sucrose | 1G | 1.55 | 1.58 | 1.53 |
| | | 5% Sorbitol | 2G | 1.02 | 1.04 | 1.01 |
| | | 0.1% Polysorbate-20 | 3G | 1.08 | 1.09 | 1.05 |
| | | 0.1% Polysorbate-80 | 4G | 0.90 | 0.91 | 0.88 |
| | | 0.1% Poloxamer P188 | 5G | 1.01 | 1.04 | 1.01 |
| | | 0.2M Arginine | 6G | 1.05 | 1.04 | 1.00 |

TABLE 5-continued

Concentration determinations are compatible between NANODROP® and SE-UPLC predictions

| Base Buffer | Salt Level | Excipient | Code | NANODROP® (mg/ml) | Conc (mg/mL) (Based on Reference Standard) | Conc (mg/mL) (Based on A280 Conversion) |
|---|---|---|---|---|---|---|
| | 150 mM Sodium Chloride | 10% Sucrose | 7G | 1.29 | 1.28 | 1.24 |
| | | 5% Sorbitol | 8G | 1.14 | 1.14 | 1.11 |
| | | 0.1% Polysorbate-20 | 9G | 1.10 | 1.11 | 1.07 |
| | | 0.1% Polysorbate-80 | 10G | 1.03 | 1.05 | 1.02 |
| | | 0.1% Poloxamer P188 | 11G | 1.02 | 1.01 | 0.98 |
| | | 0.2M Arginine | 12G | 1.04 | 1.04 | 1.01 |
| Tricine pH 8.5 | 20 mM Sodium Chloride | 10% Sucrose | 1H | 0.58 | 0.59 | 0.57 |
| | | 5% Sorbitol | 2H | 1.05 | 1.05 | 1.01 |
| | | 0.1% Polysorbate-20 | 3H | 0.97 | 0.97 | 0.94 |
| | | 0.1% Polysorbate-80 | 4H | 0.99 | 0.99 | 0.96 |
| | | 0.1% Poloxamer P188 | 5H | 0.95 | 0.92 | 0.89 |
| | | 0.2M Arginine | 6H | 1.04 | 1.04 | 1.00 |
| | 150 mM Sodium Chloride | 10% Sucrose | 7H | 1.31 | 1.32 | 1.28 |
| | | 5% Sorbitol | 8H | 0.93 | 0.93 | 0.90 |
| | | 0.1% Polysorbate-20 | 9H | 0.99 | 1.00 | 0.96 |
| | | 0.1% Polysorbate-80 | 10H | 1.02 | 1.02 | 0.99 |
| | | 0.1% Poloxamer P188 | 11H | 1.02 | 1.02 | 0.99 |
| | | 0.2M Arginine | 12H | 1.02 | 1.02 | 0.99 |

Figure 2A:
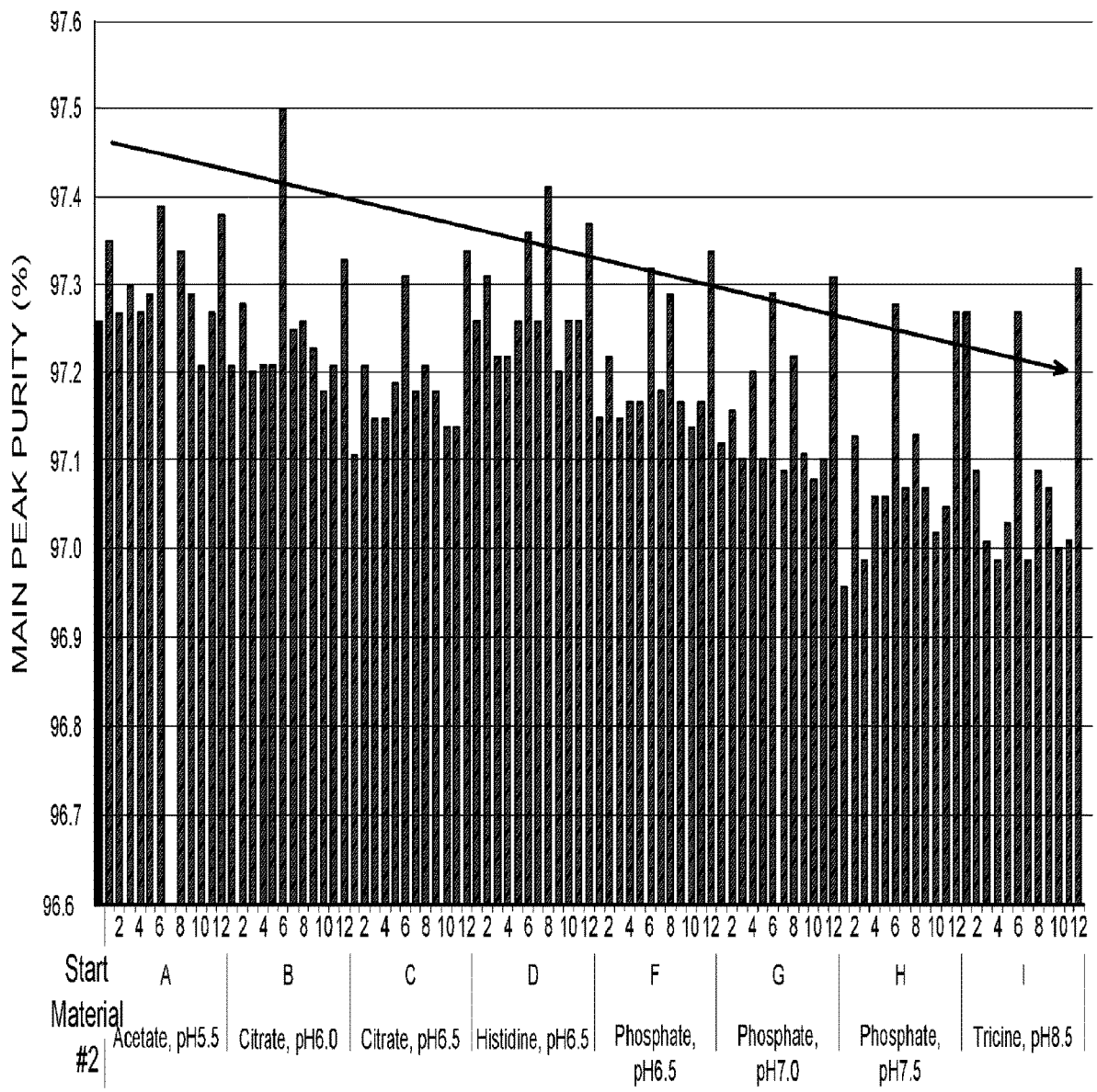
FIGS. 2A and 2B are graphs showing the relationship between main peak purity (%), as determined by SE-UPLC analysis, with increasing pH according to the different buffers tested (FIG. 2A) or with the different excipients tested (FIG. 2B).
Figure 2B:
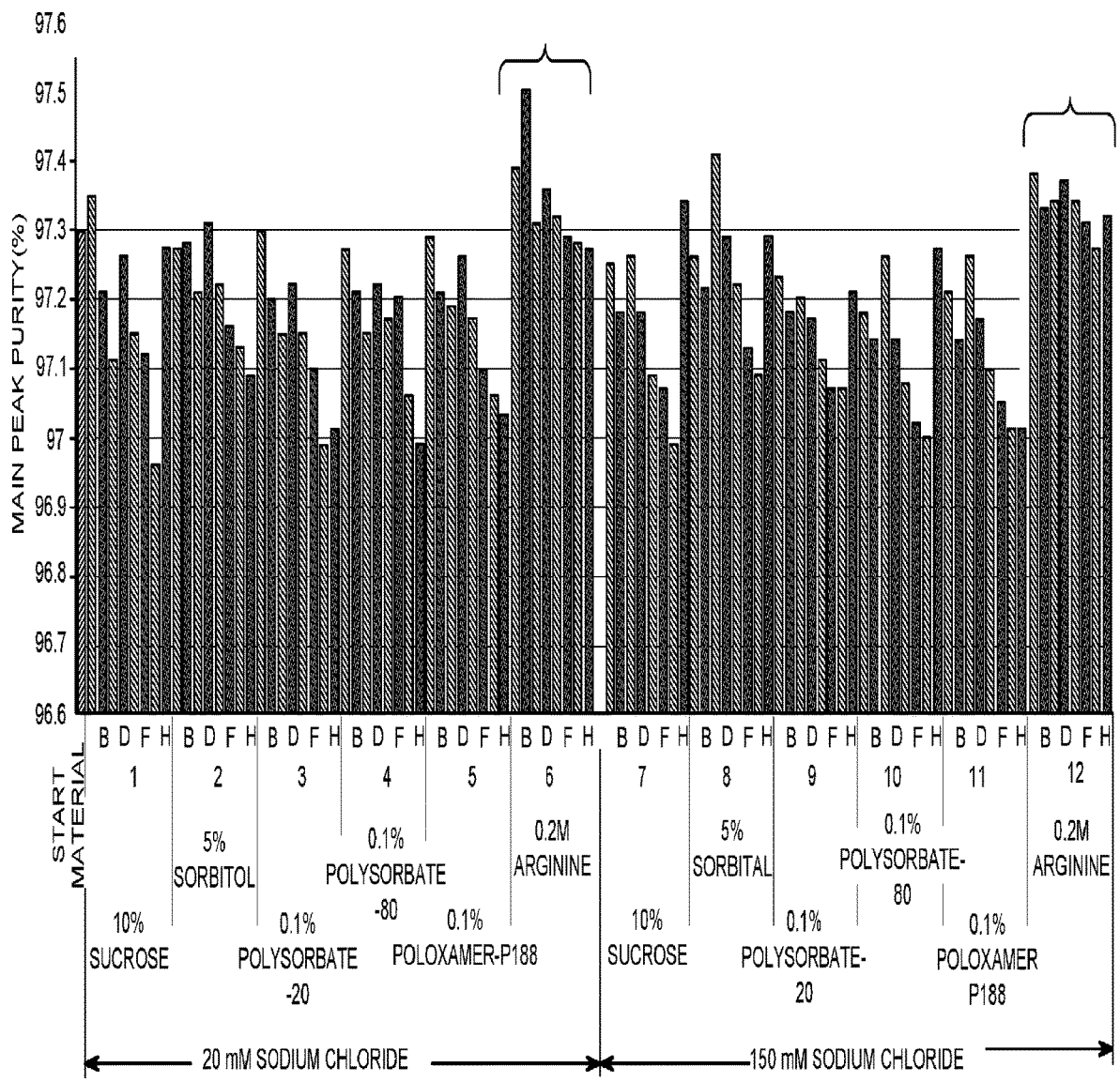

The main IgG peak purity was determined by SE-UPLC. When analyzing the main IgG peak purity with respect to pH, the main IgG peak appeared to reduce slightly as the pH of the base buffer increased (FIG. 2A). These results indicate that EBI-031 remains more stable at lower pH, e.g., more stable towards pH 5.5 than pH 8.5. When analyzing the main IgG peak purity with respect to each excipient, the excipient arginine had a positive impact on product purity (FIG. 2B). This effect was observed at both high and low salt concentrations. The other excipients may have longer term impact on product stability.

After 7 days of incubation at 40 degrees C., samples were analyzed for appearance, recovery, UV content (by NANODROP® Spectrophotomer determination), SE-UPLC, and SDS-PAGE. Analysis by appearance showed that most samples appeared clear and colorless. Approximate volumes varied between 15 and 100 μl, with most samples recovered in volumes close to expected value (25-40 μl) (adequate volume recovery for most samples, allowing analysis at ×100 dilution), and a few of the samples were too viscous for further analysis.

The concentration of the samples at day 7 was analyzed at 100-fold dilution by SEC Mobile phase A (NANODROP® Spectrophotomer). The expected protein concentration following 100-fold dilution=0.994 mg/mL Most samples generated content values slightly higher than start concentration, as a result of evaluation. The results of the NANODROP® Spectrophotomer analysis are shown in Table 6.

TABLE 6

| | | | 20 mM Sodium Chloride | | | | | | 150 mM Sodium Chloride | | | | | |
| | | | 1 - 10% Sucrose | | | | | | 7 - 10% Sucrose | | | | | |
| | | | 2 - 5% Sorbitol | | | | | | 8 - 5% Sorbitol | | | | | |
| | | | 3 - 0.1% Polysorbate-20 | | | | | | 9 - 0.1% Polysorbate-20 | | | | | |
| | | | 4 - 0.1% Polysorbate-80 | | | | | | 10 - 0.1% Polysorbate-80 | | | | | |
| | | | 5 - 0.1% Poloxamer P188 | | | | | | 11 - 0.1% Poloxamer P188 | | | | | |
| | | | 6 - 0.2M Arginine | | | | | | 12 - 0.2M Arginine | | | | | |
| Day 7 | | | 1 | 2 | 3 | 4 | 5 | 6 | 7 | 8 | 9 | 10 | 11 | 12 |
| Acetate pH 5.5 | A | | x | x | 1.04 | 1.12 | 1.84 | 1.21 | x | 1.05 | 1.29 | 1.27 | 2.16 | 0.50 |
| Citrate pH 6.0 | B | | x | 1.39 | 1.11 | 1.11 | 1.14 | 0.35 | 1.42 | 1.20 | 1.09 | 1.04 | 1.18 | 1.06 |
| Citrate pH 6.5 | C | | 1.75 | 1.22 | 1.15 | 1.08 | 1.09 | 1.20 | 1.60 | 1.22 | 1.08 | 1.14 | 1.07 | 1.15 |
| Histidine pH 6.5 | D | | 1.59 | 1.28 | 1.10 | 1.06 | 1.12 | 1.02 | 1.58 | 1.33 | 1.13 | 1.06 | 1.09 | 1.04 |
| Phosphate pH 6.5 | E | | 1.81 | 1.43 | 1.15 | 1.06 | 1.07 | 1.15 | 1.71 | 1.23 | 1.15 | 1.11 | 1.13 | 1.13 |
| Phosphate pH 7.0 | F | | 1.66 | 1.14 | 1.10 | 0.25 | 1.09 | 1.20 | 1.63 | 1.14 | 1.13 | 1.08 | 1.13 | 1.19 |
| Phosphate pH 7.5 | G | | 1.75 | 1.17 | 1.11 | 1.09 | 1.11 | 1.18 | 1.56 | 0.78 | 1.13 | 1.06 | 1.09 | 1.14 |
| Tricine pH 8.5 | H | | 0.54 | 1.19 | 0.92 | 0.99 | 1.15 | 1.24 | 1.49 | 0.79 | 1.05 | 0.99 | 1.02 | 1.10 |

Figure 4:
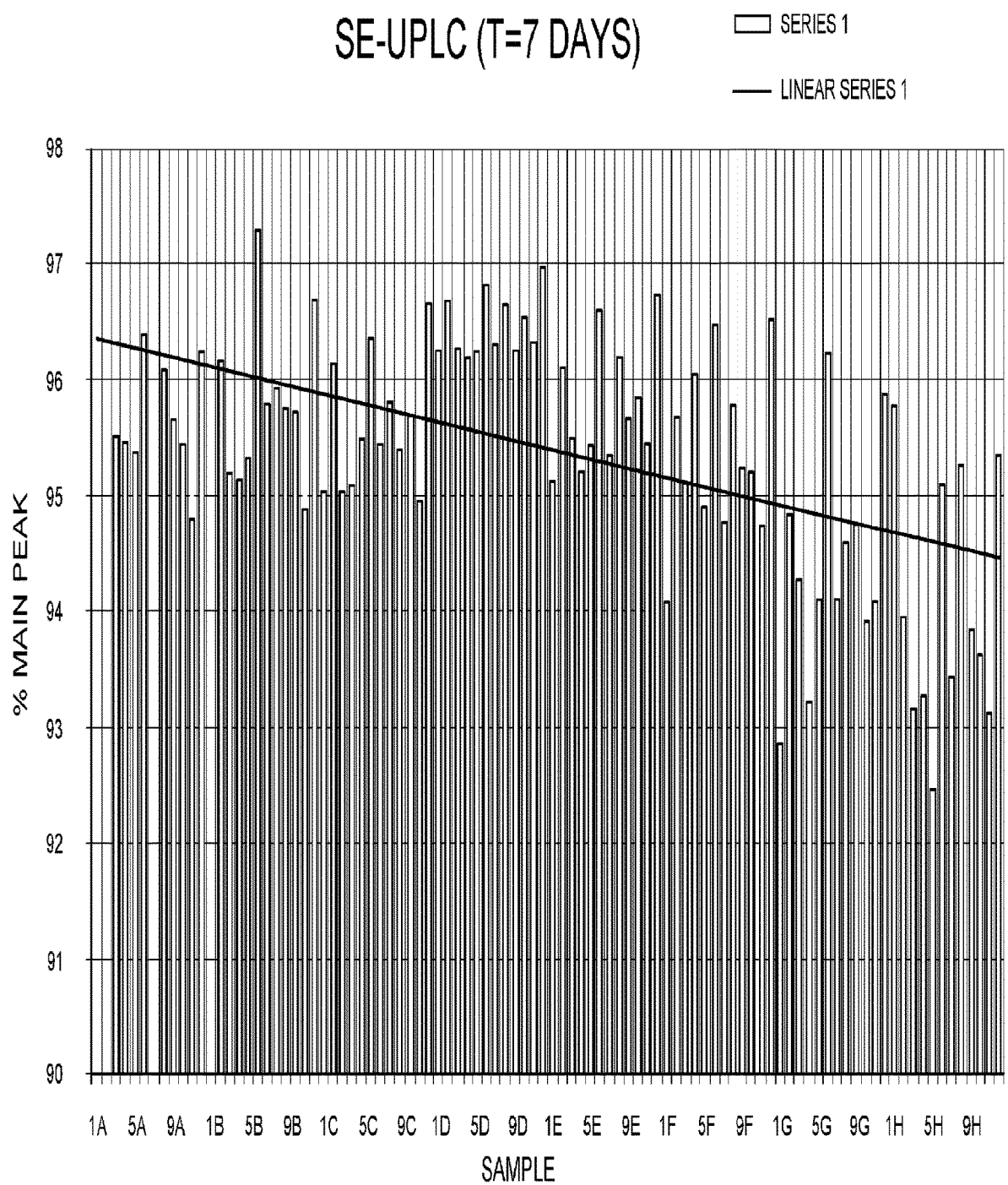
FIG. 4 is a graph showing the relationship between main peak purity (%), as determined by SE-UPLC analysis, with increasing pH according to the different buffers tested. Each buffer tested is represented on the x-axis by the well designation from the 96 well plate layout as shown in FIG. 4.
Figure 5:
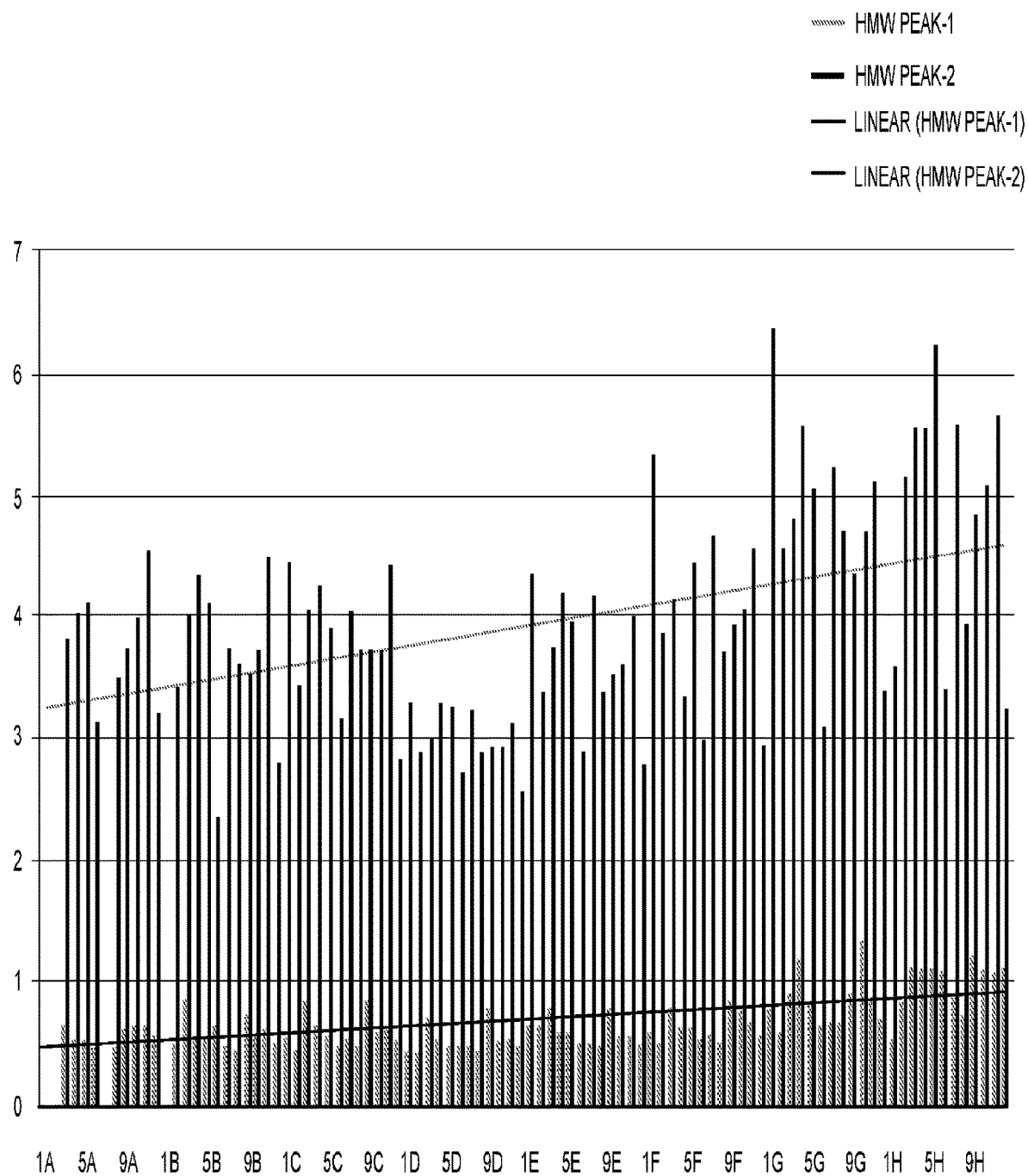
FIG. 5 is a graph showing the relationship between HMW peaks, as determined by SE-UPLC analysis, with increasing pH according to the different buffers tested. Each buffer tested is represented on the x-axis by the well designation from the 96 well plate layout as shown in FIG. 4.

SE-UPLC analysis was also performed at day 7. SE-UPLC chromatograms were overlayed according to buffer to assess the effect of the different salt concentrations and excipients on the purity of the samples. The results from SE-UPLC analysis are summarized in FIGS. 3A-3E. The data also indicates a trend towards decreased main peak percentage and increased HMW peaks with increasing pH. Purity is also reasonably consistent at low pH (FIG. 4). Histidine buffer was shown as being an optimal buffer for all excipients. Sorbitol was also shown as being the second best excipient in formulations with histidine buffer at pH 6.5 (FIG. 5).

Figure 6:
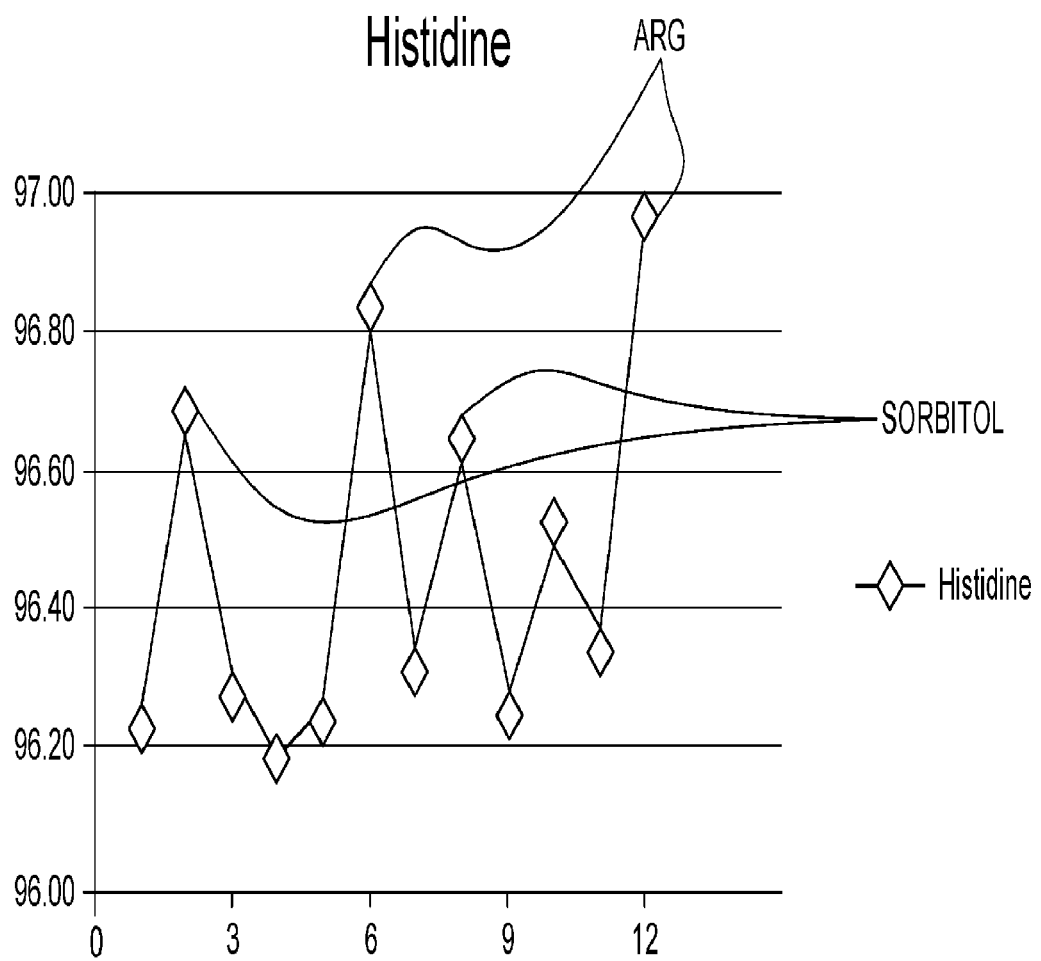
FIG. 6 is a graph showing the main peak purity (%) with respect to the different salt concentrations and excipients for the samples containing histidine buffer. On the X-axis, the numbers 1-12 represent the salt concentration and excipients present in columns 1-12 listed in FIG. 4.

FIG. 6 is a graph showing the main peak purity (%) with respect to the different salt concentrations and excipients for the samples containing histidine buffer. On the X-axis, the numbers 1-12 represent the salt concentration and excipients present in columns 1-12 listed in Table 6.

Example 4: Agitation Study

Agitation studies were performed to identify optimal detergent conditions for a formulation containing EBI-031. In the first study, polysorbate 20, polysorbate 80, and poloxamer 188 was compared (at 0.1%). In the second study, different concentrations of polysorbate 20 and polysorbate 80 were compared (0.1% and 0.03%).

In the first study, 50 and 5 mg/ml of EBI-031 in 20 mM histidine, 20 mM sodium chloride, 4% sorbital, at pH 6.5 with: 0.1% polysorbate-20, 0.1% polysorbate-80, or 0.1% poloxamer 188. Visual inspection of vials at the start and end of the study was conducted. At the beginning of the study, all samples looked clear by visual inspection. Samples were vortexed for 4 hours. NANODROP® Spectrophotometer and SE-HPLC analysis showed that agitation-induced aggregation was effectively prevented by detergents. Results of the first agitation study are summarized in FIG. 7. By SE-UPLC analysis, polysorbates appeared slightly better than poloxamer at low product concentration in the buffer conditions. These results demonstrate that all detergents appear to offer protection from agitation-induced aggregation, as assessed using SE-UPLC. Absence of detergent led to substantial aggregation at lower product concentration.

In the second study, samples were prepared containing 50 and 5 mg/ml of EBI-031 in 20 mM histidine, 20 mM sodium chloride, 4% sorbital, at pH 6.5 with: A) no detergent, B) 0.1% Tween-20, C) 0.1% Tween-80, D) 0.03% Tween-20, or E) 0.03% Tween-80. Visual inspection of vials at the start and end of the study was conducted. At the beginning of the study, all samples looked clear by visual inspection. Controls were non-agitated samples at 2-8° C. (200 µl of sample). The samples (800 µl) were agitated by Thermomixer at 400 rpm at 2-8° C., then aliquots were diluted to 1 mg/ml for analysis using SE-UPLC. The remaining samples (500 µl), following removal of material for SE-UPLC and osmolality, were reagitated by Thermomixer at 1000 rpm at 2-8° C. for 4 hours, then aliquots were diluted to 1 mg/ml for analysis by SE-UPLC. The remaining samples were reagitated by Thermomixer at 1000 rpm at 25° C. for 3 hours, then aliquots diluted to 1 mg/ml for analysis by SE-UPLC. The remaining samples were reagitated by Thermomixer at 1000 rpm at 25° C. overnight.

Figure 9A:
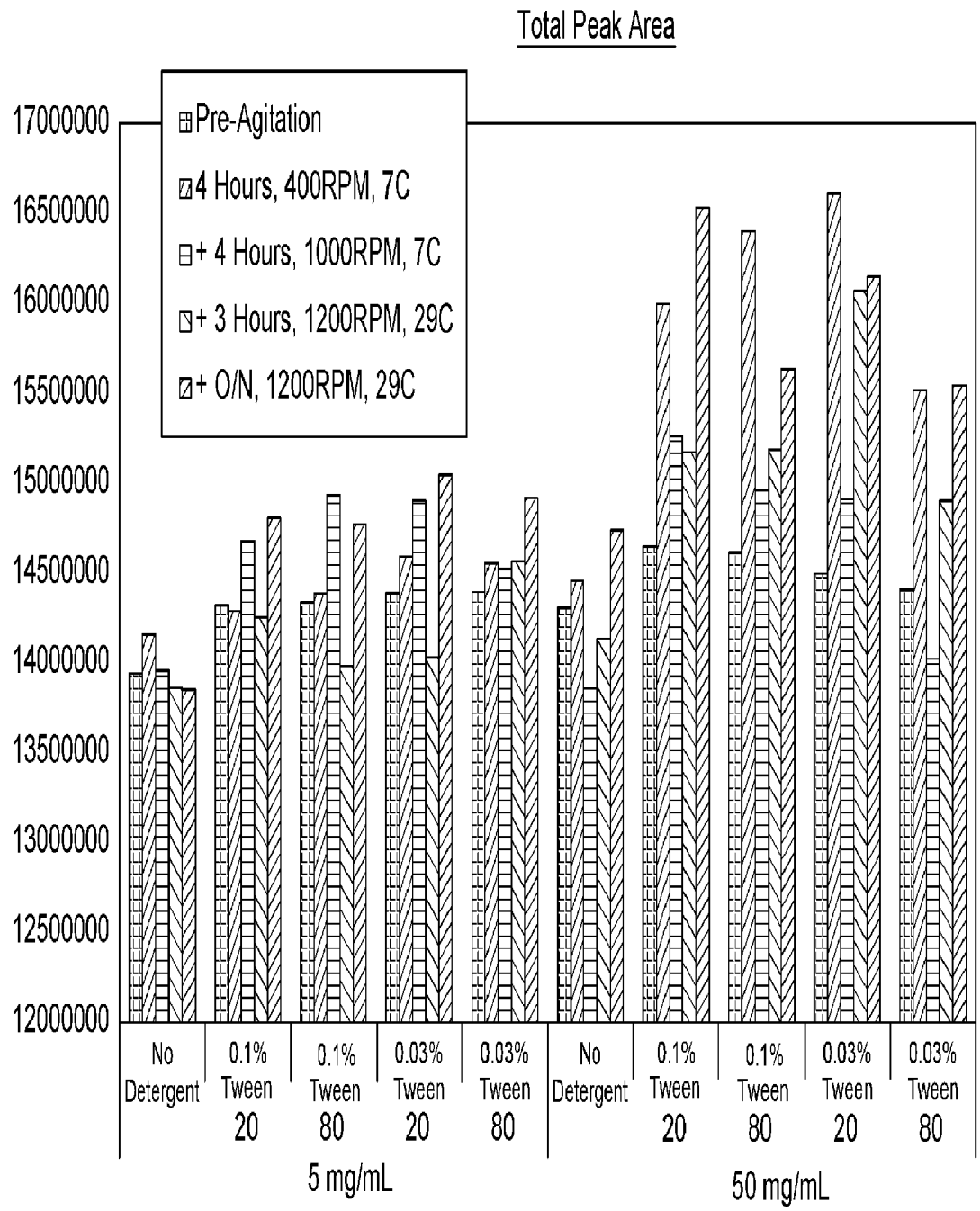
FIGS. 9A, 9B, 9C, and 9D are graphs showing the total peak area (FIG. 9A), IgG main peak purity (FIG. 9B), high molecular weight (HMW) species (FIG. 9C), and low molecular weight (LMW) species (FIG. 9D) with respect to each tested excipient under the different agitation conditions used.
Figure 9B:
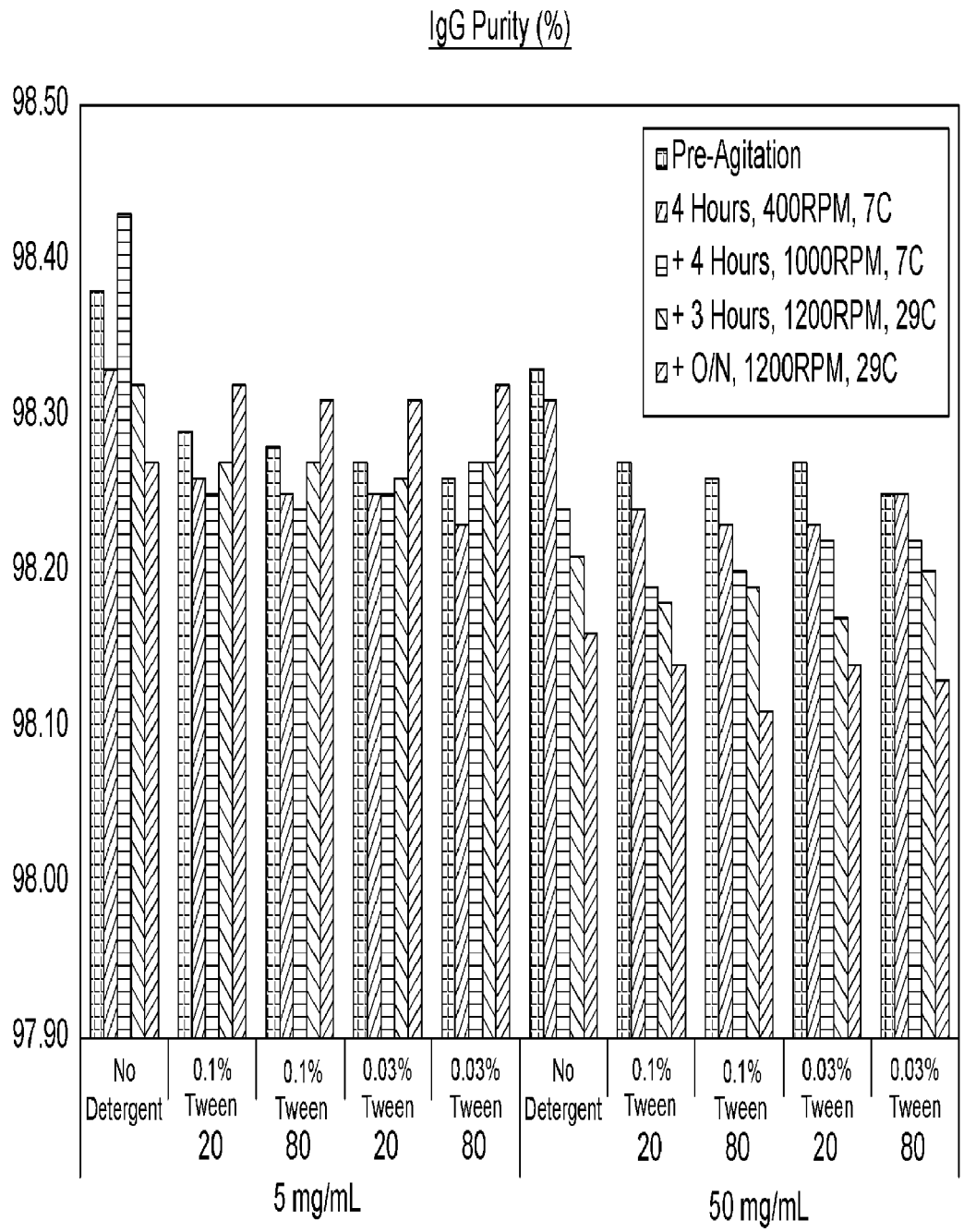
Figure 9C:
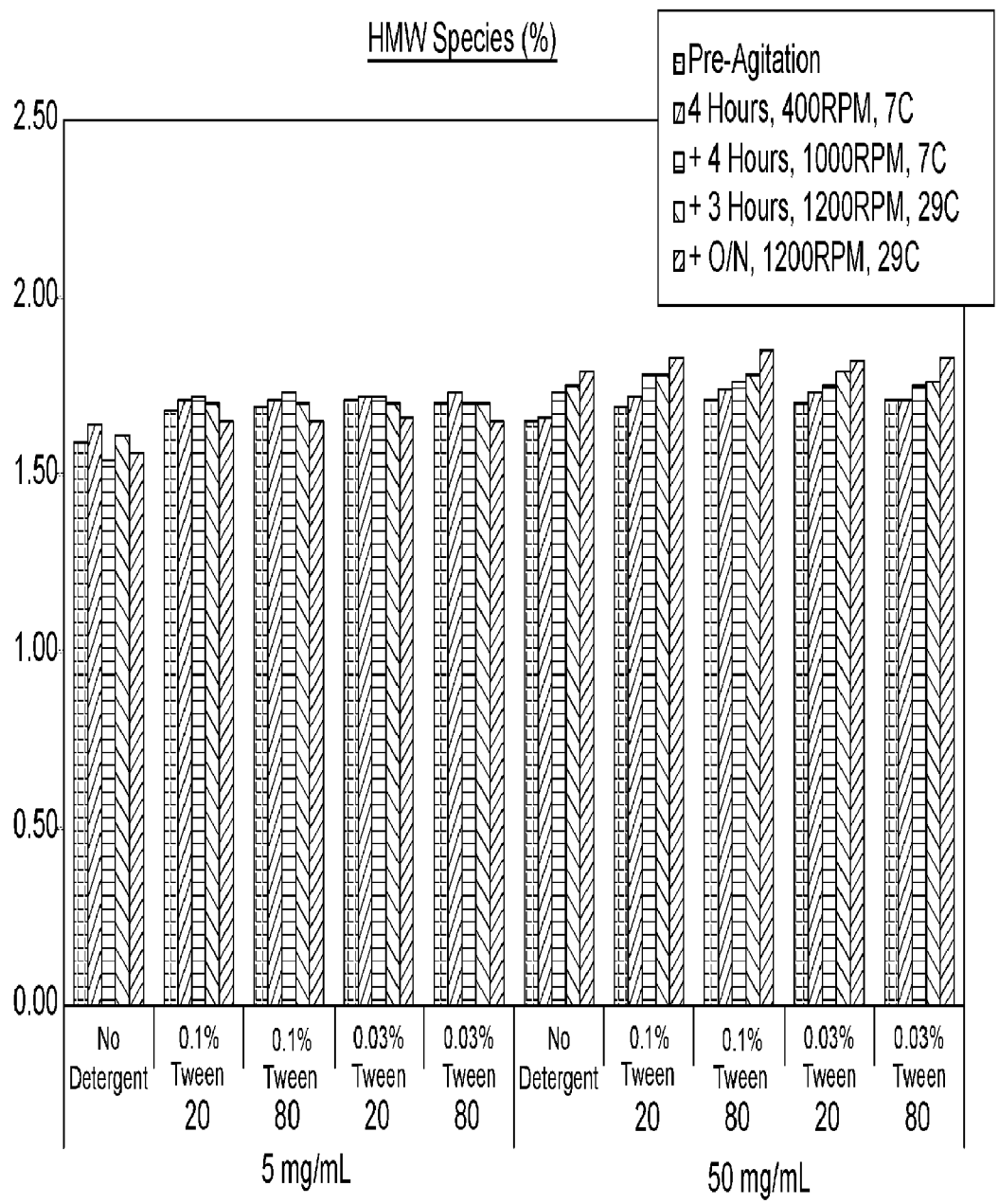
Figure 9D:
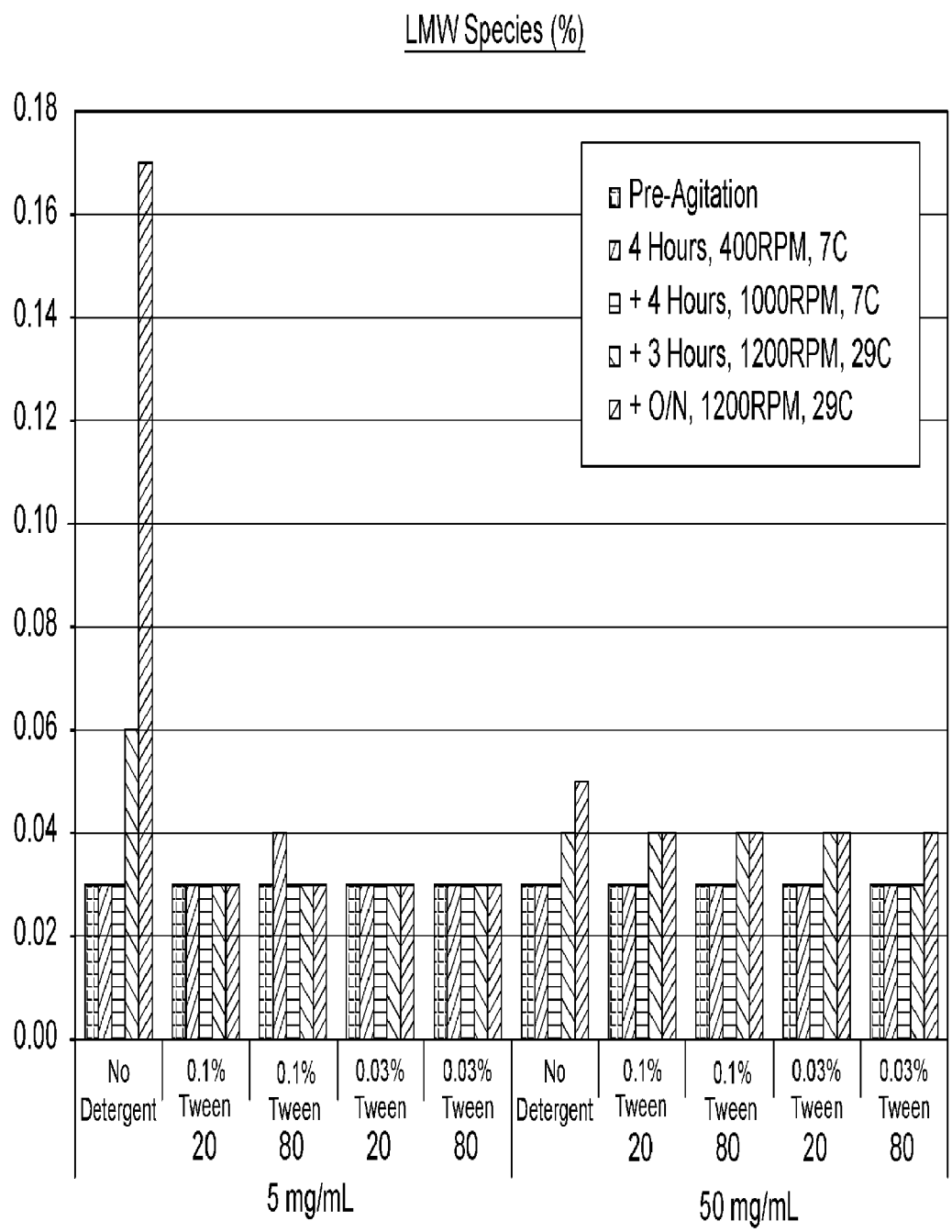

Results from the SE-UPLC analysis in the second agitation study are summarized in FIGS. 8A-8C. The results are represented in graph format by analysis of Total Peak Area (FIG. 9A), IgG Main Peak Purity (FIG. 9B), High Molecular Weight Species (FIG. 9C), and Low Molecular Weight Species (FIG. 9D). Concentration analysis was also performed on the samples by comparing the results from Solo VPE (Table 7B) and NANODROP® Spectrophotomer analysis (Table 7C), with the content estimated from SE-UPLC total peak area. The content estimated from SE-UPLC total peak area was compared to mean Ref Std and multiplied by dilution factor to obtain the content values (mg/ml) as shown in Table 7A. Correlation of the results from SE-UPLC and UV content determination indicates no substantial light scattering at 320 nm or 600 nm and no substantial loss of product content, therefore, implying minimal aggregation. Together, these results from the second agitation study showed that the product antibody demonstrated good stability with minimal changes to content, main peak purity, or HMW species. Use of detergent was not detrimental in the conditions tested. Both Tween-20 and Tween-80 at 0.03% and 0.1% concentrations appeared to be equally suitable for inclusion in formulation.

TABLE 7A

| Content (mg/mL) * |
|---|
| 4.89 |
| 5.23 |
| 5.22 |
| 5.31 |
| 5.27 |
| 52.04 |
| 58.38 |
| 55.21 |
| 57.02 |
| 54.88 |

TABLE 7B

| Treatment | Sample Concentration | Sample | Concentration (mg/mL) |
|---|---|---|---|
| +O/N, 1200 RPM, 29 C. | 5 mg/mL | No Detergent | 4.9 |
| | | 0.1% Tween 20 | 5.1 |
| | | 0.1% Tween 80 | 5.1 |
| | | 0.03% Tween 20 | 5.1 |
| | | 0.03% Tween 80 | 5.0 |
| | 50 mg/mL | No Detergent | 51.8 |
| | | 0.1% Tween 20 | 49.7 |
| | | 0.1% Tween 80 | 48.7 |
| | | 0.03% Tween 20 | 55.3 |
| | | 0.03% Tween 80 | 57.9 |

TABLE 7C

| Treatment | Sample Concentration | Sample | 280 nm | 320 nm | 600 nm | Concentration (mg/mL) |
|---|---|---|---|---|---|---|
| +O/N, 1200 RPM, 29 C. | 5 mg/mL | No Detergent | 0.768 | 0.038 | 0.005 | 5.08 |
| | | 0.1% Tween 20 | 0.764 | 0.015 | 0.003 | 5.22 |
| | | 0.1% Tween 80 | 0.753 | 0.014 | 0.001 | 5.15 |
| | | 0.03% Tween 20 | 0.751 | 0.006 | 0.000 | 5.19 |
| | | 0.03% Tween 80 | 0.787 | 0.049 | 0.009 | 5.14 |

TABLE 7C-continued

| Treatment | Sample Concentration | Sample | 280 nm | 320 nm | 600 nm | Concentration (mg/mL) |
|---|---|---|---|---|---|---|
| | 50 mg/mL | No Detergent | 1.044 | 0.087 | 0.008 | 6.66 |
| | | 0.1% Tween 20 | 1.116 | 0.052 | 0.003 | 7.41 |
| | | 0.1% Tween 80 | 1.121 | 0.058 | 0.010 | 7.40 |
| | | 0.03% Tween 20 | 0.964 | 0.053 | 0.004 | 6.34 |
| | | 0.03% Tween 80 | 1.072 | 0.053 | 0.004 | 7.10 |

Example 5: Preparation of Exemplary Formulations

GMP Manufacture

During the GMP manufacture, the Final Formulation Buffer R (20 mM Histidine, 20 mM Sodium Chloride, 4% Sorbitol, 0.03% Tween-20) will be prepared to flush the final 0.2 μm filter. To do this, 9 L of Buffer R will be made and 1 L of Buffer Q will be added (See Table 8 for details). The materials to be used in the GMP manufacture are detailed in Table 9.

TABLE 8

Buffer Receipe for Formulation Preparation

| Buffer Letter/Title/Fluid | Components | | | | pH (at 18 ± 2° C.) Target | Conductivity (mS/cm at 18 ± 2° C.) Target |
|---|---|---|---|---|---|---|
| | Material/ Conc (g/L) | Material/ Conc (g/L) | Material/ Conc (g/L) | Matrial/ Conc (g/L) | | |
| Q Spike Buffer 20 mM Histidine, 20 mM Sodium Chloride, 4% Sorbitol, 0.3% Polysorbate 20 (Tween 20) pH 6.5 | L-Histidine Hydrochloride 4.19 | Sodium Chloride 1.17 | D-Sorbitol 40 | Polysorbate 20 (Tween 20) 3.33 | 6.5 ± 0.1 | 3.5 ± 0.5 |
| R DF Buffer 20 mM Histidine, 20 mM Sodium Chloride, 4% Sorbitol pH 6.5 | L-Histidine Hydrochloride 4.19 | Sodium Chloride 1.17 | D-Sorbitol 40 | | 6.5 ± 0.1 | 3.5 ± 0.5 |
| U Final Filtration Formulation Buffer Flush 20 mM Histidine, 20 mM Sodium Chloride, 4% Sorbitol, 0.03% Polysorbate 20 (Tween 20) pH 6.5 | Buffer R 910.44 (900 mL) | Buffer Q 101.32 (100 mL) | | | 6.5 ± 0.1 | 3.5 ± 0.5 | pH for Buffer Q and Buffer R is adjusted with sodium hydroxide 25% solution.

The shelf-life at room temperature of the buffers of Table 3 is 3 days.

Buffer Q: Requires 1.7 mL/L of Sodium Hydroxide (25%). Back titration is not allowed. Final Buffer Density=1.0132 kg/L. Osmolality Specification=300-340 mOsm/kg.

Buffer R: Requires 1.7 mL/L of Sodium Hydroxide (25%). Back titration is not allowed. Final Buffer Density=1.01160 kg/L. Osmolality Specification=300-340 mOsm/kg.

Buffer U: This buffer is made by mixing 9 parts Buffer R to 1 part Buffer Q. A specified volume of Buffer R will be made and the required volume of Buffer Q will then be added.

TABLE 9

Raw Material Source

| FFDB Number | Material Description | Molecular Weight | Supplier | Supplier Number |
|---|---|---|---|---|
| 850275 | D-Sorbitol | 182.17 | Merck KGaA | 111597 |
| 812693 | L-Histidine Hydrochloride | 209.63 | Avantor | 2081 |
| 812270 | Polysorbate 20 (Tween 20) | Not Stated | Avantor | 4116 |
| 630261 | Sodium Chloride | 58.44 | Merck KGaA | 116224 |
| 811428 | Sodium Hydroxide 25% Solution | 40.00 | Avantor | 2613 |

Details of Dilutions for Toxicology Study Material.

The starting material was at 70.3 g/L. This material was diluted to a target of 55.5 g/L with Buffer R (20 mM Histidine, 20 mM Sodium Chloride, 4% Sorbitol). The product was then diluted 9 parts product to 1 part Buffer Q (20 mM Histidine, 20 mM Sodium Chloride, 4% Sorbitol, 0.3% Tween-20) to achieve a final EBI-031 concentration of 50.6 g/L and a final Tween-20 concentration of 0.03%.

A portion of the 50.6 g/L sample was diluted 1 part product to 1 part Buffer U (20 mM Histidine, 20 mM Sodium Chloride, 4% Sorbitol, 0.03% Tween-20) to achieve a final concentration of 25.3 g/L.

A portion of the 25.3 g/L material was further diluted 1 part product to 4 parts Buffer U to achieve a final concentration of 5.1 g/L. All concentrations were determined by $A_{280}$ with $A_{320}$ correction.

Example 6: Characterization of the Structural Isoforms of an IgG2 IL-6 Antibody EBI-031 is an IgG2 antibody (sequences are provided in Table 1). As discussed previously, IgG2 antibodies exist in three different structural isoforms, IgG2-A, IgG2-B, and IgG2-AB isoforms (FIG. 10). In this example, experiments were performed to identify the structural isoforms in EBI-031 samples and distribution thereof from different sample sources and in the presence of a reducing agent.

RP-HPLC Analysis

Reversed-phase high-performance liquid chromatograph (RP-HPLC) was used to resolve the various structural isoforms of EBI-031. An enhanced analytical RP-HPLC method that has been used previously for resolving IgG2 disulfide-mediated structural isoforms (see, Dillon et al., Journal of Chromatography A, 2006, 1120:112-120) was optimized for resolving EBI-031.

EBI-031 samples containing approximately 30 μg was loaded onto a Zorbax 300SB-C8 column (150 mm×2.1 mm, 5.0 μm, 300 Å). The column temperature was set at 75° C. Mobile phase A was water containing 0.1% TFA, and mobile phase B was 55% IPA, 40% ACN, 4.9% water and 0.1% TFA. The flow rate was 0.5 mL/min. The column was initially equilibrated with 90% mobile phase A and 10% mobile phase B for 2 min followed by a 2 min step gradient from 10 to 25% B. Elution was achieved with a linear gradient of 25-32% B over 21 min. UV absorbance was monitored at 214 nm and/or 280 nm.

Figure 11:
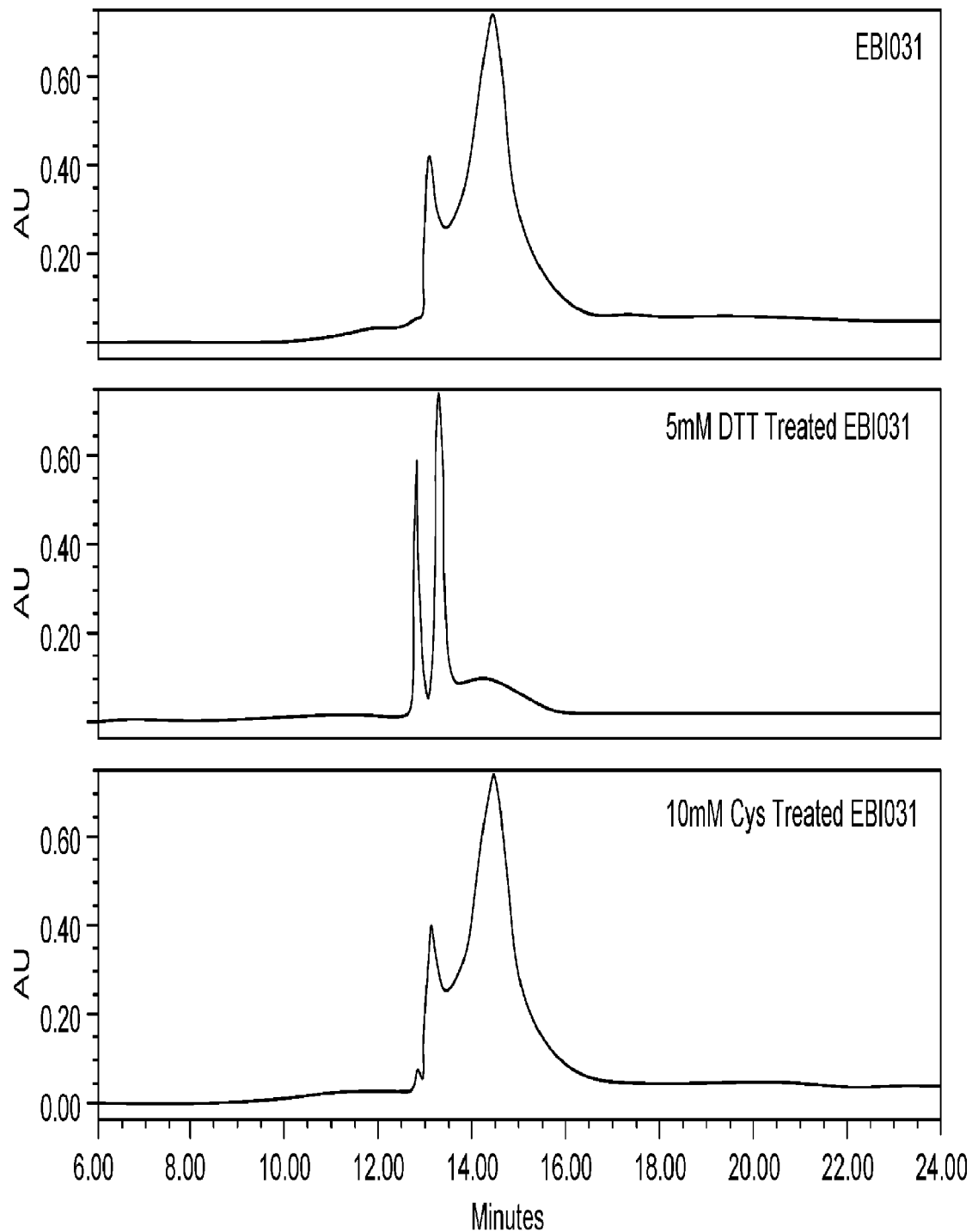
FIG. 11 shows RP-HPLC chromatograms of EBI-031 samples: untreated (top panel), 5 mM DTT (middle panel), 10 mM cysteine (bottom panel).

In order to determine whether the resolution was disulfide-related, the samples were treated with 5 mM DTT and 10 mM cysteine at room temperature for 2 min and then analyzed on the RP-HPLC method (FIG. 11). Treatment with DTT, which is a potent reducing agent, causes reduction of the IgG2 antibody, resulting in elution into early peaks (Peak 0 and Peak 1) (FIG. 11, middle panel). Treatment with cysteine, which is a milder reducing agent compared to DTT, shifts the isoform distribution towards the early peaks (Peak 0 and Peak 1) as well, though not to the extent seen with the DTT-treated sample (FIG. 11, bottom panel).

The data demonstrates that the RP-HPLC method resolved the structural isoforms with different disulfide connectivity. The different disulfide bonding structures were confirmed by non-reduced peptide mapping and mass spectrometry analysis: the early eluting peak (Peak 1) contains the IgG2-A/B isoform and the late eluting peak (Peak 2) contains the IgG2-A isoform. Importantly, there was no IgG2-B isoform B (Peak 0) detected in the EBI-031 sample (FIG. 11, top panel).

Isoform Heterogeneity in Different EBI-031 Samples

Using the RP-HPLC analysis described above, EBI-031 samples collected from different EBI-031-expressing cell lines were analyzed to compare the isoform distribution of the antibodies produced. EBI-031 samples were collected from a 200L scale culture of a clonal cell line, a 10L scale culture from a parental cell line, and a stably transfected pool of cells. EBI-031 was purified using a three-step chromatography method from the clonal and parental EBI-031 expressing cell lines. EBI-031 was purified from the stably transfected pool of cells using Protein A purification. The samples were analyzed by the methods described above.

Figure 12:
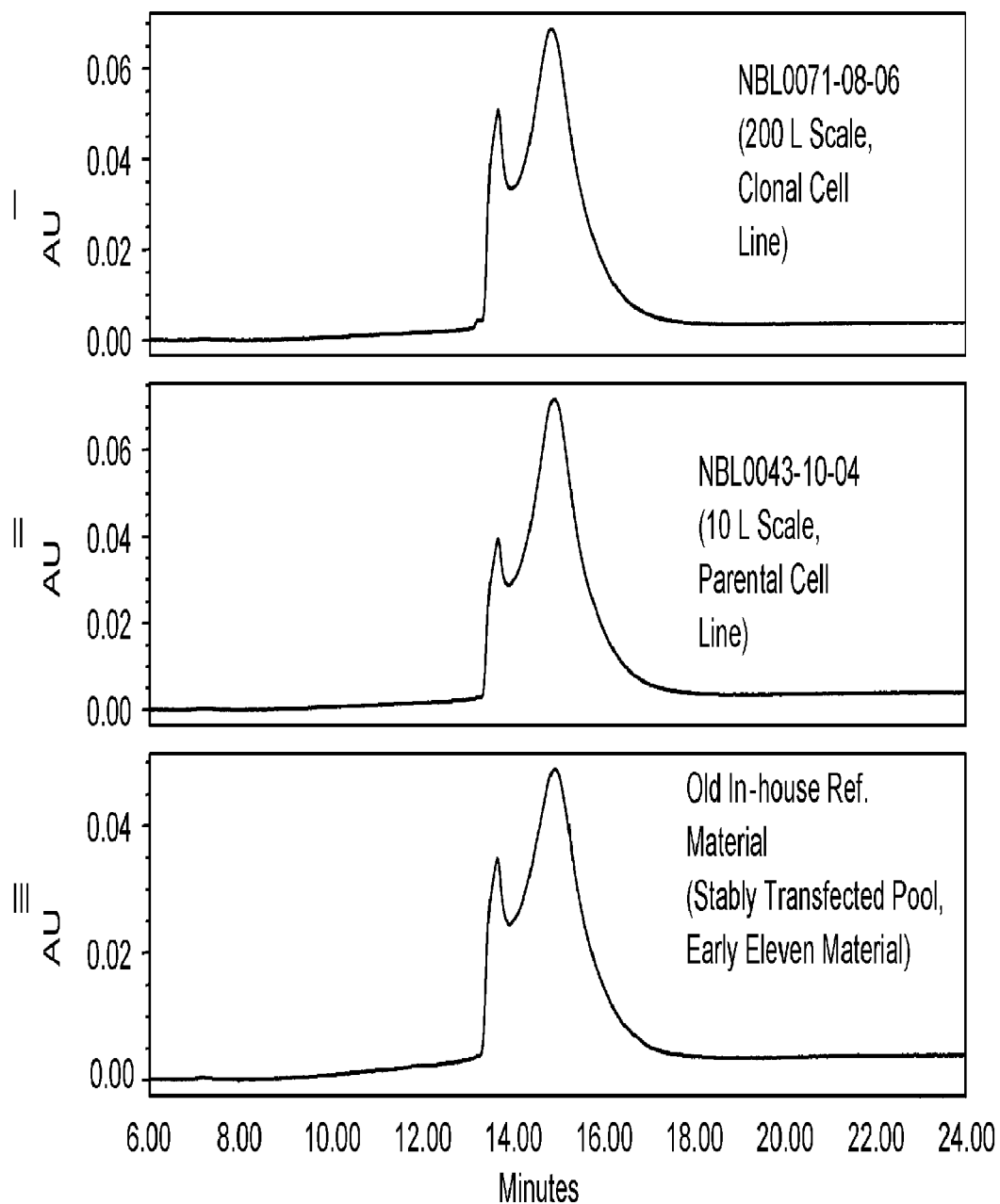
FIG. 12 shows RP-HPLC chromatograms of EBI-031 samples collected from different EBI-031 cell lines: a 200L scale culture of a clonal cell line (top panel), a 10L scale culture from a parental cell line (middle panel), and a stably transfected pool of cells (bottom panel).
Figure 13:
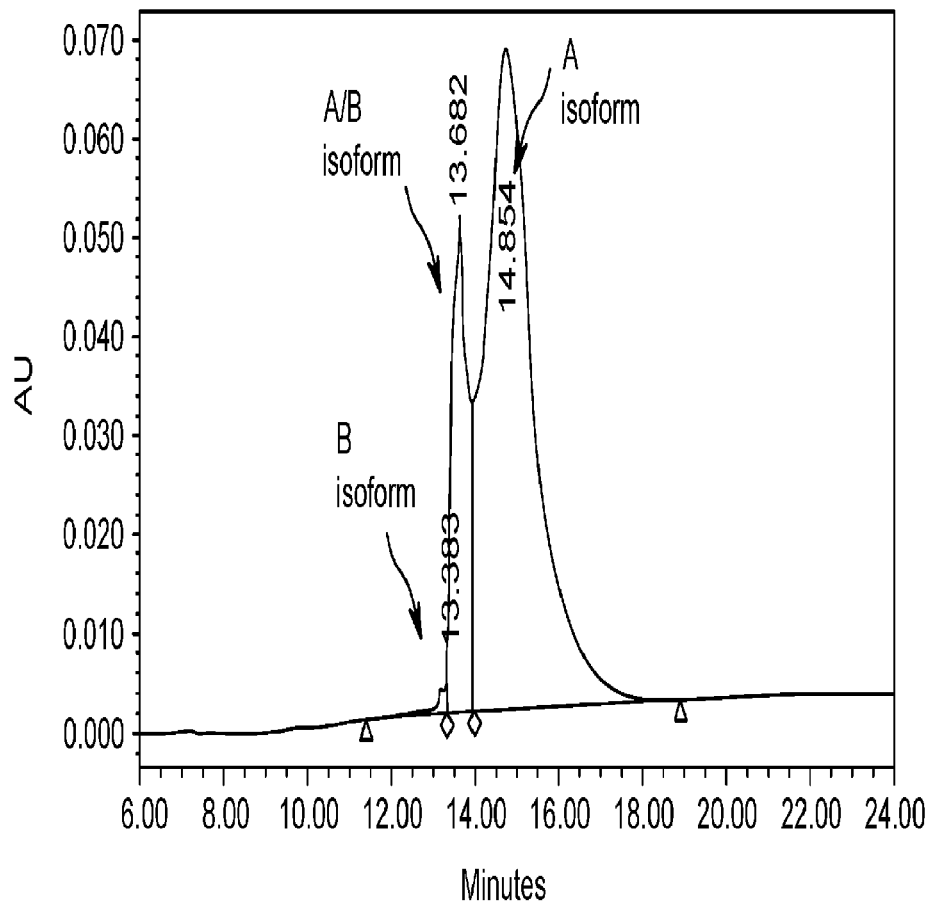
FIG. 13 shows the RP-HPLC chromatogram of EBI-031 collected from a 200L scale culture of a clonal cell line, and designates and quantifies which isoforms are represented by each peak in the chromatogram.

The results shown in FIG. 12 show that all three EBI-031 samples contained isoforms IgG2-A and IgG2-A/B, but no substantial amount of IgG2-B. This data demonstrates that the EBI-031 IgG2 antibody is produced in a less heterogeneous mixture than other IgG2 antibodies, whether the production is from a clonal EBI-031-expressing cell line, a parental EBI-031-expressing cell line, or from a heterogeneous cell population that stably expresses EBI-031. FIG. 13 shows the distribution of the isoforms from the EBI-031 sample from the 200L scale culture of a clonal EBI-031-expressing cell line, e.g., the top panel of FIG. 12. The areas under the curves were also measured, and the distributions among the isoforms are shown in the table below the figure.

Other embodiments are within the scope of the following claims.

---

What is claimed is:

1. A pharmaceutical formulation comprising 1-100 mg/ml of an anti-IL-6 antibody or fragment thereof; 10-50 mM histidine; 0.01%-0.1% polysorbate-20, polysorbate-80, or poloxamer 188; 1-150 mM sodium chloride; and 1-10% sorbitol; wherein the pH of the formulation is between 6 and 7 and the anti-IL-6 antibody comprises a variable heavy (VH) domain comprising a VH CDR1 comprising the sequence of SEQ ID NO: 19, a VH CDR2 comprising the sequence of SEQ ID NO: 10, and a VH CDR3 comprising the sequence of SEQ ID NO: 21, and a variable light (VL) domain comprising a VL CDR1 comprising the sequence of SEQ ID NO: 22, a VL CDR2 comprising the sequence of SEQ ID NO: 23, and a VL CDR3 comprising the sequence of SEQ ID NO:24.

2. The formulation of claim 1, wherein the formulation comprises 5-50 mg/ml of the anti-IL-6 antibody or fragment thereof.

3. The formulation of claim 1, wherein the VH domain comprises SEQ ID NO: 17.

4. The formulation of claim 1, wherein the VL domain comprise SEQ ID NO: 18.

5. The formulation of claim 1, wherein the IL-6 antibody or fragment thereof comprises a heavy chain sequence comprising SEQ ID NO: 25.

6. The formulation of claim 1, wherein the IL-6 antibody or fragment thereof comprises a light chain sequence comprising SEQ ID NO: 14.

7. The formulation of claim 1, wherein the formulation comprises 10-30 mM histidine buffer.

8. The formulation of claim 1, wherein the formulation comprises 0.01%-0.05% polysorbate-20 polysorbate-80, or poloxamer 188.

9. The formulation of claim 1, wherein the formulation comprises 0.03% polysorbate-20, polysorbate-80, or poloxamer 188.

10. The formulation of claim 1, wherein the formulation comprises 10-50 mM sodium chloride.

11. The formulation of claim 1, wherein the formulation comprises 2-6% sorbitol.

12. The formulation of claim 1, wherein the pH of the formulation is of 6.5.

13. A method of treating a subject having an IL-6 associated disease, comprising administering to the subject the pharmaceutical formulation of claim 1, wherein the IL-6 associated disease is selected from the group consisting of diabetic macular edema (DME), diabetic retinopathy, dry eye disease, dry eye syndrome, allergic conjunctivitis, uveitis, age-related macular degeneration (AMD), proliferative diabetic retinopathy (PDR), Rhegmatogenous retinal detachment (RRD), retinal vein occlusion (RVO), neuromyelitis optica (NMO), myopic choroidal neovascularization, an ocular cancer, corneal transplant, corneal abrasion, or physical injury to the eye.

14. The method of claim 13, wherein the formulation is administered to the eye.

15. The method of claim 14, wherein the formulation is administered intravitreally.

16. The method of claim 15, wherein the formulation is administered by intravitreal injection.

17. The method of claim 13, wherein the IL-6 associated disease is diabetic macular edema (DME).

18. The method of claim 13, wherein the AMD is wet AMD.

19. The method of claim 13, wherein the AMD is dry AMD.

* * * * *

SEQUENCE LISTING

```
<160> NUMBER OF SEQ ID NOS: 31

<210> SEQ ID NO 1
<211> LENGTH: 448
<212> TYPE: PRT
<213> ORGANISM: Artificial Sequence
<220> FEATURE:
<223> OTHER INFORMATION: EBI-029 HC (IgG2)

<400> SEQUENCE: 1

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Leu Ser Asn Tyr
            20                  25                  30

Leu Ile Glu Trp Val Arg Gln Ala Pro Gly Gln Gly Leu Glu Trp Met
        35                  40                  45

Gly Val Ile Thr Pro Gly Ser Gly Thr Ile Asn Tyr Ala Gln Lys Phe
```

```
                50                  55                  60
Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                    85                  90                  95

Ala Arg Ser Arg Trp Asp Pro Leu Tyr Tyr Ala Leu Glu Tyr Trp
                100                 105                 110

Gly Gln Gly Thr Thr Val Thr Val Ser Ser Ala Ser Thr Lys Gly Pro
                115                 120                 125

Ser Val Phe Pro Leu Ala Pro Cys Ser Arg Ser Thr Ser Glu Ser Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Asn Phe Gly Thr Gln Thr Tyr Thr Cys Asn Val Asp
                195                 200                 205

His Lys Pro Ser Asn Thr Lys Val Asp Lys Thr Val Glu Arg Lys Cys
210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Gln Phe Asn Trp Tyr Val Asp Gly Val Glu Val His Asn Ala
                275                 280                 285

Lys Thr Lys Pro Arg Glu Glu Gln Phe Asn Ser Thr Phe Arg Val Val
                290                 295                 300

Ser Val Leu Thr Val Val His Gln Asp Trp Leu Asn Gly Lys Glu Tyr
305                 310                 315                 320

Lys Cys Lys Val Ser Asn Lys Gly Leu Pro Ala Pro Ile Glu Lys Thr
                325                 330                 335

Ile Ser Lys Thr Lys Gly Gln Pro Arg Glu Pro Gln Val Tyr Thr Leu
                340                 345                 350

Pro Pro Ser Arg Glu Glu Met Thr Lys Asn Gln Val Ser Leu Thr Cys
                355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Met Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445
```

<210> SEQ ID NO 2
<211> LENGTH: 448
<212> TYPE: PRT
<213> ORGANISM: Artificial Sequence

<220> FEATURE:
<223> OTHER INFORMATION: EBI-029 HC -H311A

<400> SEQUENCE: 2

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Leu Ser Asn Tyr
            20                  25                  30

Leu Ile Glu Trp Val Arg Gln Ala Pro Gly Gln Gly Leu Glu Trp Met
        35                  40                  45

Gly Val Ile Thr Pro Gly Ser Gly Thr Ile Asn Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Arg Trp Asp Pro Leu Tyr Tyr Ala Leu Glu Tyr Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Cys Ser Arg Ser Thr Ser Glu Ser Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Phe Arg Val Val
290                 295                 300

Ser Val Leu Thr Val Val Ala Gln Asp Trp Leu Asn Gly Lys Glu Tyr
305                 310                 315                 320

Lys Cys Lys Val Ser Asn Lys Gly Leu Pro Ala Pro Ile Glu Lys Thr
                325                 330                 335

Ile Ser Lys Thr Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Met Leu Asp
385                 390                 395                 400
```

```
Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 3
<211> LENGTH: 218
<212> TYPE: PRT
<213> ORGANISM: Artificial Sequence
<220> FEATURE:
<223> OTHER INFORMATION: EBI-029 LC

<400> SEQUENCE: 3

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Asp Asn Tyr
            20                  25                  30

Gly Ile Pro Phe Met Asn Trp Tyr Gln Gln Lys Pro Gly Gln Pro Pro
        35                  40                  45

Lys Leu Leu Ile Tyr Ala Ala Ser Asn Arg Gly Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Glu
                85                  90                  95

Glu Val Pro Leu Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 4
<211> LENGTH: 230
<212> TYPE: PRT
<213> ORGANISM: Artificial Sequence
<220> FEATURE:
<223> OTHER INFORMATION: EBI-029 (IgG1) Fab HC

<400> SEQUENCE: 4

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Leu Ser Asn Tyr
            20                  25                  30

Leu Ile Glu Trp Val Arg Gln Ala Pro Gly Gln Gly Leu Glu Trp Met
```

```
            35                  40                  45
Gly Val Ile Thr Pro Gly Ser Gly Thr Ile Asn Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Arg Trp Asp Pro Leu Tyr Tyr Tyr Ala Leu Glu Tyr Trp
                100                 105                 110

Gly Gln Gly Thr Thr Val Thr Val Ser Ser Ala Ser Thr Lys Gly Pro
            115                 120                 125

Ser Val Phe Pro Leu Ala Pro Ser Ser Lys Ser Thr Ser Gly Gly Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
210                 215                 220

Cys Asp Lys Thr His Thr
225                 230

<210> SEQ ID NO 5
<211> LENGTH: 122
<212> TYPE: PRT
<213> ORGANISM: Artificial Sequence
<220> FEATURE:
<223> OTHER INFORMATION: EBI-029 VH

<400> SEQUENCE: 5

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Ala Leu Ser Asn Tyr
             20                  25                  30

Leu Ile Glu Trp Val Arg Gln Ala Pro Gly Gln Gly Leu Glu Trp Met
         35                  40                  45

Gly Val Ile Thr Pro Gly Ser Gly Thr Ile Asn Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Arg Trp Asp Pro Leu Tyr Tyr Tyr Ala Leu Glu Tyr Trp
                100                 105                 110

Gly Gln Gly Thr Thr Val Thr Val Ser Ser
            115                 120

<210> SEQ ID NO 6
<211> LENGTH: 114
<212> TYPE: PRT
<213> ORGANISM: Artificial Sequence
<220> FEATURE:
<223> OTHER INFORMATION: EBI-029 VL
```

```
<400> SEQUENCE: 6

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Asp Asn Tyr
            20                  25                  30

Gly Ile Pro Phe Met Asn Trp Tyr Gln Gln Lys Pro Gly Gln Pro Pro
        35                  40                  45

Lys Leu Leu Ile Tyr Ala Ala Ser Asn Arg Gly Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Glu
                85                  90                  95

Glu Val Pro Leu Thr Phe Gly Gln Gly Thr Lys Leu Glu Ile Lys Arg
            100                 105                 110

Thr Val

<210> SEQ ID NO 7
<211> LENGTH: 10
<212> TYPE: PRT
<213> ORGANISM: Artificial Sequence
<220> FEATURE:
<223> OTHER INFORMATION: EBI-029 HC CDR1

<400> SEQUENCE: 7

Gly Tyr Ala Leu Ser Asn Tyr Leu Ile Glu
1               5                   10

<210> SEQ ID NO 8
<211> LENGTH: 10
<212> TYPE: PRT
<213> ORGANISM: Artificial Sequence
<220> FEATURE:
<223> OTHER INFORMATION: EBI-029 HC CDR2

<400> SEQUENCE: 8

Val Ile Thr Pro Gly Ser Gly Thr Ile Asn
1               5                   10

<210> SEQ ID NO 9
<211> LENGTH: 13
<212> TYPE: PRT
<213> ORGANISM: Artificial Sequence
<220> FEATURE:
<223> OTHER INFORMATION: EBI-029 HC CDR3

<400> SEQUENCE: 9

Ser Arg Trp Asp Pro Leu Tyr Tyr Tyr Ala Leu Glu Tyr
1               5                   10

<210> SEQ ID NO 10
<211> LENGTH: 15
<212> TYPE: PRT
<213> ORGANISM: Artificial Sequence
<220> FEATURE:
<223> OTHER INFORMATION: EBI-029 LC CDR1

<400> SEQUENCE: 10

Arg Ala Ser Glu Ser Val Asp Asn Tyr Gly Ile Pro Phe Met Asn
1               5                   10                  15
```

```
<210> SEQ ID NO 11
<211> LENGTH: 7
<212> TYPE: PRT
<213> ORGANISM: Artificial Sequence
<220> FEATURE:
<223> OTHER INFORMATION: EBI-029 LC CDR2

<400> SEQUENCE: 11

Ala Ala Ser Asn Arg Gly Ser
1               5

<210> SEQ ID NO 12
<211> LENGTH: 9
<212> TYPE: PRT
<213> ORGANISM: Artificial Sequence
<220> FEATURE:
<223> OTHER INFORMATION: EBI-029 LC CDR3

<400> SEQUENCE: 12

Gln Gln Ser Glu Glu Val Pro Leu Thr
1               5

<210> SEQ ID NO 13
<211> LENGTH: 448
<212> TYPE: PRT
<213> ORGANISM: Artificial Sequence
<220> FEATURE:
<223> OTHER INFORMATION: EBI-030 HC (IgG2)

<400> SEQUENCE: 13

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Val Leu Pro Asn Tyr
            20                  25                  30

Leu Ile Glu Trp Val Arg Gln Ala Pro Gly Gln Gly Leu Glu Trp Met
        35                  40                  45

Gly Val Thr Thr Pro Gly Gly Gly Thr Ile Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Arg Trp Asp Pro Leu Tyr Tyr Ala Leu Glu Tyr Trp
            100                 105                 110

Gly Gln Gly Thr Thr Val Thr Val Ser Ser Ala Ser Thr Lys Gly Pro
            115                 120                 125

Ser Val Phe Pro Leu Ala Pro Cys Ser Arg Ser Thr Ser Glu Ser Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
    210                 215                 220

Cys Val Glu Cys Pro Pro Cys Pro Ala Pro Pro Val Ala Gly Pro Ser
225                 230                 235                 240
```

Val Phe Leu Phe Pro Pro Lys Pro Lys Asp Thr Leu Met Ile Ser Arg
             245                 250                 255

Thr Pro Glu Val Thr Cys Val Val Val Asp Val Ser His Glu Asp Pro
         260                 265                 270

Glu Val Gln Phe Asn Trp Tyr Val Asp Gly Val Glu Val His Asn Ala
         275                 280                 285

Lys Thr Lys Pro Arg Glu Glu Gln Phe Asn Ser Thr Phe Arg Val Val
         290                 295                 300

Ser Val Leu Thr Val Val His Gln Asp Trp Leu Asn Gly Lys Glu Tyr
305                 310                 315                 320

Lys Cys Lys Val Ser Asn Lys Gly Leu Pro Ala Pro Ile Glu Lys Thr
                 325                 330                 335

Ile Ser Lys Thr Lys Gly Gln Pro Arg Glu Pro Gln Val Tyr Thr Leu
                 340                 345                 350

Pro Pro Ser Arg Glu Glu Met Thr Lys Asn Gln Val Ser Leu Thr Cys
             355                 360                 365

Leu Val Lys Gly Phe Tyr Pro Ser Asp Ile Ala Val Glu Trp Glu Ser
         370                 375                 380

Asn Gly Gln Pro Glu Asn Asn Tyr Lys Thr Thr Pro Pro Met Leu Asp
385                 390                 395                 400

Ser Asp Gly Ser Phe Phe Leu Tyr Ser Lys Leu Thr Val Asp Lys Ser
                 405                 410                 415

Arg Trp Gln Gln Gly Asn Val Phe Ser Cys Ser Val Met His Glu Ala
             420                 425                 430

Leu His Asn His Tyr Thr Gln Lys Ser Leu Ser Leu Ser Pro Gly Lys
         435                 440                 445

<210> SEQ ID NO 14
<211> LENGTH: 218
<212> TYPE: PRT
<213> ORGANISM: Artificial Sequence
<220> FEATURE:
<223> OTHER INFORMATION: EBI-030 LC

<400> SEQUENCE: 14

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Asp Asn Tyr
             20                  25                  30

Gly Ile Pro Phe Met Asn Trp Tyr Gln Gln Lys Pro Gly Gln Pro Pro
         35                  40                  45

Lys Leu Leu Ile Tyr Ala Ala Ser Asn Arg Gly Ser Gly Val Pro Asp
     50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Glu
                 85                  90                  95

Glu Val Pro Leu Thr Phe Gly Gln Gly Thr Lys Leu Glu Ile Lys Arg
             100                 105                 110

Thr Val Ala Ala Pro Ser Val Phe Ile Phe Pro Pro Ser Asp Glu Gln
         115                 120                 125

Leu Lys Ser Gly Thr Ala Ser Val Val Cys Leu Leu Asn Asn Phe Tyr
     130                 135                 140

Pro Arg Glu Ala Lys Val Gln Trp Lys Val Asp Asn Ala Leu Gln Ser
145                 150                 155                 160

```
Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 15
<211> LENGTH: 230
<212> TYPE: PRT
<213> ORGANISM: Artificial Sequence
<220> FEATURE:
<223> OTHER INFORMATION: EBI-030 (IgG1) Fab HC

<400> SEQUENCE: 15

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Val Leu Pro Asn Tyr
            20                  25                  30

Leu Ile Glu Trp Val Arg Gln Ala Pro Gly Gln Gly Leu Glu Trp Met
        35                  40                  45

Gly Val Thr Thr Pro Gly Gly Gly Thr Ile Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Arg Trp Asp Pro Leu Tyr Tyr Ala Leu Glu Tyr Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr
225                 230

<210> SEQ ID NO 16
<211> LENGTH: 223
<212> TYPE: PRT
<213> ORGANISM: Artificial Sequence
<220> FEATURE:
<223> OTHER INFORMATION: EBI-030 (IgG2) Fab HC

<400> SEQUENCE: 16

Gln Val Gln Leu Val Gln Ser Gly Ala Glu Val Lys Lys Pro Gly Ser
```

```
1               5                   10                  15
Ser Val Lys Val Ser Cys Lys Ala Ser Gly Tyr Val Leu Pro Asn Tyr
            20                  25                  30

Leu Ile Glu Trp Val Arg Gln Ala Pro Gly Gln Gly Leu Glu Trp Met
            35                  40                  45

Gly Val Thr Thr Pro Gly Gly Thr Ile Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Arg Trp Asp Pro Leu Tyr Tyr Tyr Ala Leu Glu Tyr Trp
            100                 105                 110

Gly Gln Gly Thr Thr Val Thr Val Ser Ser Ala Ser Thr Lys Gly Pro
            115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
            195                 200                 205

His Lys Pro Ser Asn Thr Lys Val Asp Lys Thr Val Glu Arg Lys
    210                 215                 220

<210> SEQ ID NO 17
<211> LENGTH: 122
<212> TYPE: PRT
<213> ORGANISM: Artificial Sequence
<220> FEATURE:
<223> OTHER INFORMATION: EBI-030 VH

<400> SEQUENCE: 17

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Val Leu Pro Asn Tyr
            20                  25                  30

Leu Ile Glu Trp Val Arg Gln Ala Pro Gly Gln Gly Leu Glu Trp Met
            35                  40                  45

Gly Val Thr Thr Pro Gly Gly Thr Ile Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Arg Trp Asp Pro Leu Tyr Tyr Tyr Ala Leu Glu Tyr Trp
            100                 105                 110

Gly Gln Gly Thr Thr Val Thr Val Ser Ser
            115                 120

<210> SEQ ID NO 18
<211> LENGTH: 114
<212> TYPE: PRT
```

<213> ORGANISM: Artificial Sequence
<220> FEATURE:
<223> OTHER INFORMATION: EBI-030 VL

<400> SEQUENCE: 18

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Asp Asn Tyr
            20                  25                  30

Gly Ile Pro Phe Met Asn Trp Tyr Gln Gln Lys Pro Gly Gln Pro Pro
        35                  40                  45

Lys Leu Leu Ile Tyr Ala Ala Ser Asn Arg Gly Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Glu
                85                  90                  95

Glu Val Pro Leu Thr Phe Gly Gln Gly Thr Lys Leu Glu Ile Lys Arg
            100                 105                 110

Thr Val

<210> SEQ ID NO 19
<211> LENGTH: 10
<212> TYPE: PRT
<213> ORGANISM: Artificial Sequence
<220> FEATURE:
<223> OTHER INFORMATION: EBI-030 HC CDR1

<400> SEQUENCE: 19

Gly Tyr Val Leu Pro Asn Tyr Leu Ile Glu
1               5                   10

<210> SEQ ID NO 20
<211> LENGTH: 10
<212> TYPE: PRT
<213> ORGANISM: Artificial Sequence
<220> FEATURE:
<223> OTHER INFORMATION: EBI-030 HC CDR2

<400> SEQUENCE: 20

Val Thr Thr Pro Gly Gly Gly Thr Ile Asn
1               5                   10

<210> SEQ ID NO 21
<211> LENGTH: 13
<212> TYPE: PRT
<213> ORGANISM: Artificial Sequence
<220> FEATURE:
<223> OTHER INFORMATION: EBI-030- HC CDR3

<400> SEQUENCE: 21

Ser Arg Trp Asp Pro Leu Tyr Tyr Tyr Ala Leu Glu Tyr
1               5                   10

<210> SEQ ID NO 22
<211> LENGTH: 15
<212> TYPE: PRT
<213> ORGANISM: Artificial Sequence
<220> FEATURE:
<223> OTHER INFORMATION: EBI-030 LC CDR1

<400> SEQUENCE: 22

Arg Ala Ser Glu Ser Val Asp Asn Tyr Gly Ile Pro Phe Met Asn

<210> SEQ ID NO 23
<211> LENGTH: 7
<212> TYPE: PRT
<213> ORGANISM: Artificial Sequence
<220> FEATURE:
<223> OTHER INFORMATION: EBI-030 LC CDR2

<400> SEQUENCE: 23

Ala Ala Ser Asn Arg Gly Ser
1               5

<210> SEQ ID NO 24
<211> LENGTH: 9
<212> TYPE: PRT
<213> ORGANISM: Artificial Sequence
<220> FEATURE:
<223> OTHER INFORMATION: EBI-030 LC CDR3

<400> SEQUENCE: 24

Gln Gln Ser Glu Glu Val Pro Leu Thr
1               5

<210> SEQ ID NO 25
<211> LENGTH: 448
<212> TYPE: PRT
<213> ORGANISM: Artificial Sequence
<220> FEATURE:
<223> OTHER INFORMATION: EBI-031 IgG2 HC

<400> SEQUENCE: 25

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Val Leu Pro Asn Tyr
                20                  25                  30

Leu Ile Glu Trp Val Arg Gln Ala Pro Gly Gln Gly Leu Glu Trp Met
            35                  40                  45

Gly Val Thr Thr Pro Gly Gly Gly Thr Ile Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Arg Trp Asp Pro Leu Tyr Tyr Tyr Ala Leu Glu Tyr Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Cys Ser Arg Ser Thr Ser Glu Ser Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
        210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Phe Arg Val Val
    290                 295                 300

Ser Val Leu Thr Val Val Ala Gln Asp Trp Leu Asn Gly Lys Glu Tyr
305                 310                 315                 320

Lys Cys Lys Val Ser Asn Lys Gly Leu Pro Ala Pro Ile Glu Lys Thr
                325                 330                 335

Ile Ser Lys Thr Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Met Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 26
<211> LENGTH: 251
<212> TYPE: PRT
<213> ORGANISM: Artificial Sequence
<220> FEATURE:
<223> OTHER INFORMATION: scFv VH-VL

<400> SEQUENCE: 26

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Val Leu Pro Asn Tyr
                20                  25                  30

Leu Ile Glu Trp Val Arg Gln Ala Pro Gly Gln Gly Leu Glu Trp Met
            35                  40                  45

Gly Val Thr Thr Pro Gly Gly Gly Thr Ile Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Arg Trp Asp Pro Leu Tyr Tyr Ala Leu Glu Tyr Trp
            100                 105                 110

Gly Gln Gly Thr Thr Val Thr Val Ser Ser Gly Gly Gly Gly Ser Gly
        115                 120                 125

Gly Gly Gly Ser Gly Gly Gly Gly Ser Asp Ile Val Met Thr Gln Ser
    130                 135                 140

Pro Asp Ser Leu Ala Val Ser Leu Gly Glu Arg Ala Thr Ile Asn Cys
145                 150                 155                 160

Arg Ala Ser Glu Ser Val Asp Asn Tyr Gly Ile Pro Phe Met Asn Trp
            165                 170                 175

Tyr Gln Gln Lys Pro Gly Gln Pro Pro Lys Leu Leu Ile Tyr Ala Ala
            180                 185                 190

Ser Asn Arg Gly Ser Gly Val Pro Asp Arg Phe Ser Gly Ser Gly Ser
        195                 200                 205

Gly Thr Asp Phe Thr Leu Thr Ile Ser Ser Leu Gln Ala Glu Asp Val
        210                 215                 220

Ala Val Tyr Tyr Cys Gln Gln Ser Glu Glu Val Pro Leu Thr Phe Gly
225                 230                 235                 240

Gln Gly Thr Lys Leu Glu Ile Lys Arg Thr Val
            245                 250

<210> SEQ ID NO 27
<211> LENGTH: 251
<212> TYPE: PRT
<213> ORGANISM: Artificial Sequence
<220> FEATURE:
<223> OTHER INFORMATION: scFv VL-VH

<400> SEQUENCE: 27

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Asp Asn Tyr
            20                  25                  30

Gly Ile Pro Phe Met Asn Trp Tyr Gln Gln Lys Pro Gly Gln Pro Pro
        35                  40                  45

Lys Leu Leu Ile Tyr Ala Ala Ser Asn Arg Gly Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Glu
                85                  90                  95

Glu Val Pro Leu Thr Phe Gly Gln Gly Thr Lys Leu Glu Ile Lys Arg
            100                 105                 110

Thr Val Gly Gly Gly Gly Ser Gly Gly Gly Ser Gly Gly Gly Gly
        115                 120                 125

Ser Gln Val Gln Leu Val Gln Ser Gly Ala Glu Val Lys Lys Pro Gly
        130                 135                 140

Ser Ser Val Lys Val Ser Cys Lys Ala Ser Gly Tyr Val Leu Pro Asn
145                 150                 155                 160

Tyr Leu Ile Glu Trp Val Arg Gln Ala Pro Gly Gln Gly Leu Glu Trp
            165                 170                 175

Met Gly Val Thr Thr Pro Gly Gly Gly Thr Ile Asn Tyr Ala Gln Lys
            180                 185                 190

Phe Gln Gly Arg Val Thr Ile Thr Ala Asp Glu Ser Thr Ser Thr Ala
        195                 200                 205

Tyr Met Glu Leu Ser Ser Leu Arg Ser Glu Asp Thr Ala Val Tyr Tyr
        210                 215                 220

Cys Ala Arg Ser Arg Trp Asp Pro Leu Tyr Tyr Ala Leu Glu Tyr
225                 230                 235                 240

Trp Gly Gln Gly Thr Thr Val Thr Val Ser Ser
            245                 250

<210> SEQ ID NO 28
<211> LENGTH: 326
<212> TYPE: PRT
<213> ORGANISM: Artificial Sequence
<220> FEATURE:
<223> OTHER INFORMATION: 030 IgG2 constant region

<400> SEQUENCE: 28

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325
```

<210> SEQ ID NO 29
<211> LENGTH: 326
<212> TYPE: PRT
<213> ORGANISM: Artificial Sequence
<220> FEATURE:
<223> OTHER INFORMATION: 031 IgG2 constant region

<400> SEQUENCE: 29

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val Ala Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325
```

<210> SEQ ID NO 30
<211> LENGTH: 10
<212> TYPE: PRT
<213> ORGANISM: Artificial Sequence
<220> FEATURE:
<223> OTHER INFORMATION: VH CDR1
<220> FEATURE:
<221> NAME/KEY: Xaa
<222> LOCATION: (3)..(3)
<223> OTHER INFORMATION: Xaa is not A, Xaa is V or a conservative

```
      substitution for V, Xaa is selected from V, I L, and M, Xaa is
      selected from V, I, and L, Xaa is V, Xaa is A.
<220> FEATURE:
<221> NAME/KEY: Xaa
<222> LOCATION: (5)..(5)
<223> OTHER INFORMATION: Xaa is not S, Xaa is P or a conservative
      substitution for P, Xaa is selected from P, G and A, Xaa is
      selected from G and P, Xaa is V, Xaa is S.

<400> SEQUENCE: 30

Gly Tyr Xaa Leu Xaa Asn Tyr Leu Ile Glu
1               5                   10

<210> SEQ ID NO 31
<211> LENGTH: 10
<212> TYPE: PRT
<213> ORGANISM: Artificial Sequence
<220> FEATURE:
<223> OTHER INFORMATION: VH CDR2
<220> FEATURE:
<221> NAME/KEY: Xaa
<222> LOCATION: (2)..(2)
<223> OTHER INFORMATION: Xaa is not I, Xaa is T or a conservative
      substitution for T, Xaa is selected from T and S, Xaa is T, Xaa is
      I.
<220> FEATURE:
<221> NAME/KEY: Xaa
<222> LOCATION: (6)..(6)
<223> OTHER INFORMATION: Xaa is not S, Xaa is G or a conservative
      substitution for G, Xaa is selected from G and P, Xaa is G, Xaa is
      S.

<400> SEQUENCE: 31

Val Xaa Thr Pro Gly Xaa Gly Thr Ile Asn
1               5                   10
```